(12) United States Patent
Banerjee et al.

(10) Patent No.: US 8,241,573 B2
(45) Date of Patent: Aug. 14, 2012

(54) SYSTEMS AND DEVICES FOR SEQUENCE BY SYNTHESIS ANALYSIS

(75) Inventors: Saibal Banerjee, Hayward, CA (US); Colin Barnes, Essex (GB); Kevin Benson, Essex (GB); Jason Bryant, Essex (GB); Dale Buermann, Los Altos, CA (US); Sergey Etchin, Hayward, CA (US); Johnny Ho, Hayward, CA (US); Xavier Lee, Hayward, CA (US); Peter Lundberg, Los Altos, CA (US); Klaus Maisinger, Cambridge (GB); Bojan Obradovic, Essex (GB); Mark Pratt, Hayward, CA (US); Mark Reed, Menlo Park, CA (US); Chiara Rodighiero, Essex (GB); Subra Sankar, Hayward, CA (US); Harold Swerdlow, Essex (GB); Eric Vermaas, Hayward, CA (US)

(73) Assignee: Illumina, Inc., San Diego, CA (US)

( * ) Notice: Subject to any disclaimer, the term of this patent is extended or adjusted under 35 U.S.C. 154(b) by 407 days.

(21) Appl. No.: 12/295,337

(22) PCT Filed: Mar. 30, 2007

(86) PCT No.: PCT/US2007/007991
§ 371 (c)(1),
(2), (4) Date: Dec. 17, 2009

(87) PCT Pub. No.: WO2007/123744
PCT Pub. Date: Nov. 1, 2007

(65) Prior Publication Data
US 2010/0111768 A1    May 6, 2010

Related U.S. Application Data

(60) Provisional application No. 60/788,248, filed on Mar. 31, 2006, provisional application No. 60/795,368, filed on Apr. 26, 2006.

(51) Int. Cl.
*G01N 21/64* (2006.01)
*G06K 9/00* (2006.01)
*C12M 1/36* (2006.01)

(52) U.S. Cl. .................. 422/82.05; 422/82.08; 435/6.1; 435/91.1; 435/287.2; 382/128; 382/129

(58) Field of Classification Search ....................... None
See application file for complete search history.

(56) References Cited

U.S. PATENT DOCUMENTS
6,136,543 A    10/2000 Anazawa et al.
(Continued)

FOREIGN PATENT DOCUMENTS
WO    WO0157249    8/2001
(Continued)

OTHER PUBLICATIONS

Lehr et al "Real-time detection of nucleic acid interactions by total internal reflection fluorescence" Analytical Chemistry, 2003, 75: 2414-2420.*

(Continued)

*Primary Examiner* — Betty Forman
(74) *Attorney, Agent, or Firm* — The Small Patent Law Group LLC; Dean Small; Jason P. Gross

(57) ABSTRACT

The present invention comprises systems and devices for sequencing of nucleic acid, such as short DNA sequences from clonally amplified single-molecule arrays.

54 Claims, 58 Drawing Sheets

U.S. PATENT DOCUMENTS

| | | | |
|---|---|---|---|
| 6,661,937 B2 * | 12/2003 | Sobiski et al. | 385/11 |
| 2001/0003043 A1 * | 6/2001 | Metspalu et al. | 435/6 |
| 2003/0012531 A1 * | 1/2003 | Nechitailo et al. | 385/114 |
| 2003/0151742 A1 * | 8/2003 | Silvermintz et al. | 356/318 |
| 2005/0019842 A1 * | 1/2005 | Prober et al. | 435/7.9 |
| 2006/0110756 A1 * | 5/2006 | Tang et al. | 435/6 |
| 2007/0160175 A1 * | 7/2007 | Lang | 376/103 |

FOREIGN PATENT DOCUMENTS

| | | |
|---|---|---|
| WO | WO03048387 A2 | 6/2003 |
| WO | WO2004072294 A2 | 8/2004 |
| WO | WO2004076683 A2 | 9/2004 |

OTHER PUBLICATIONS

Mehta et al "Use of optical traps in single-molecule study of nonprocessive biological motors" Methods in Enzymology, 1998, vol. 298: 436-459.*

Adessi et al., "Solid phase DNA amplification: characterisation of primer attachment and amplification mechanisms", Nucleic Acids Research, 2000, 28(20), pp. 108.

International Preliminary Report on Patentability mail date Oct. 14, 2008.

* cited by examiner

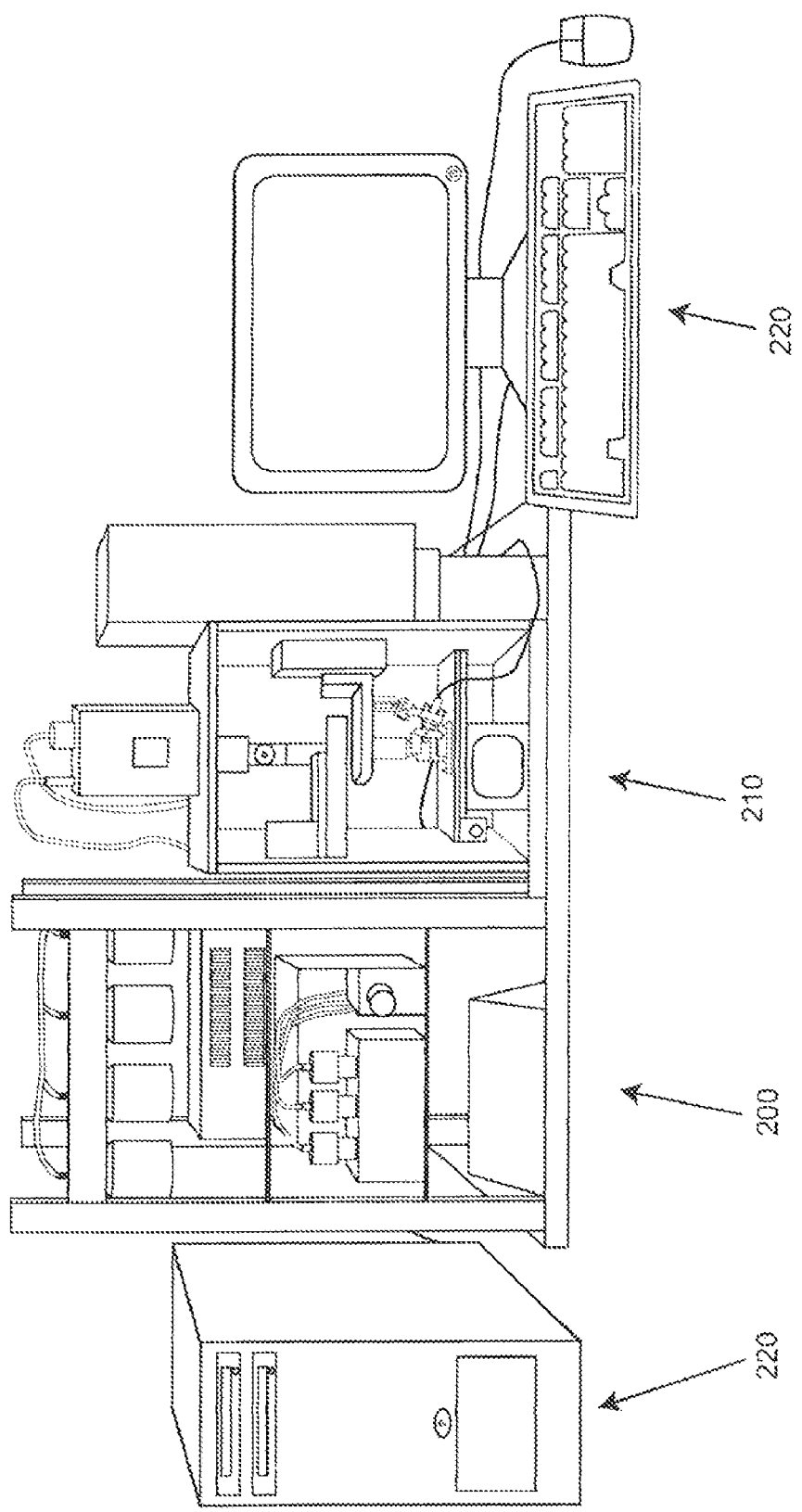

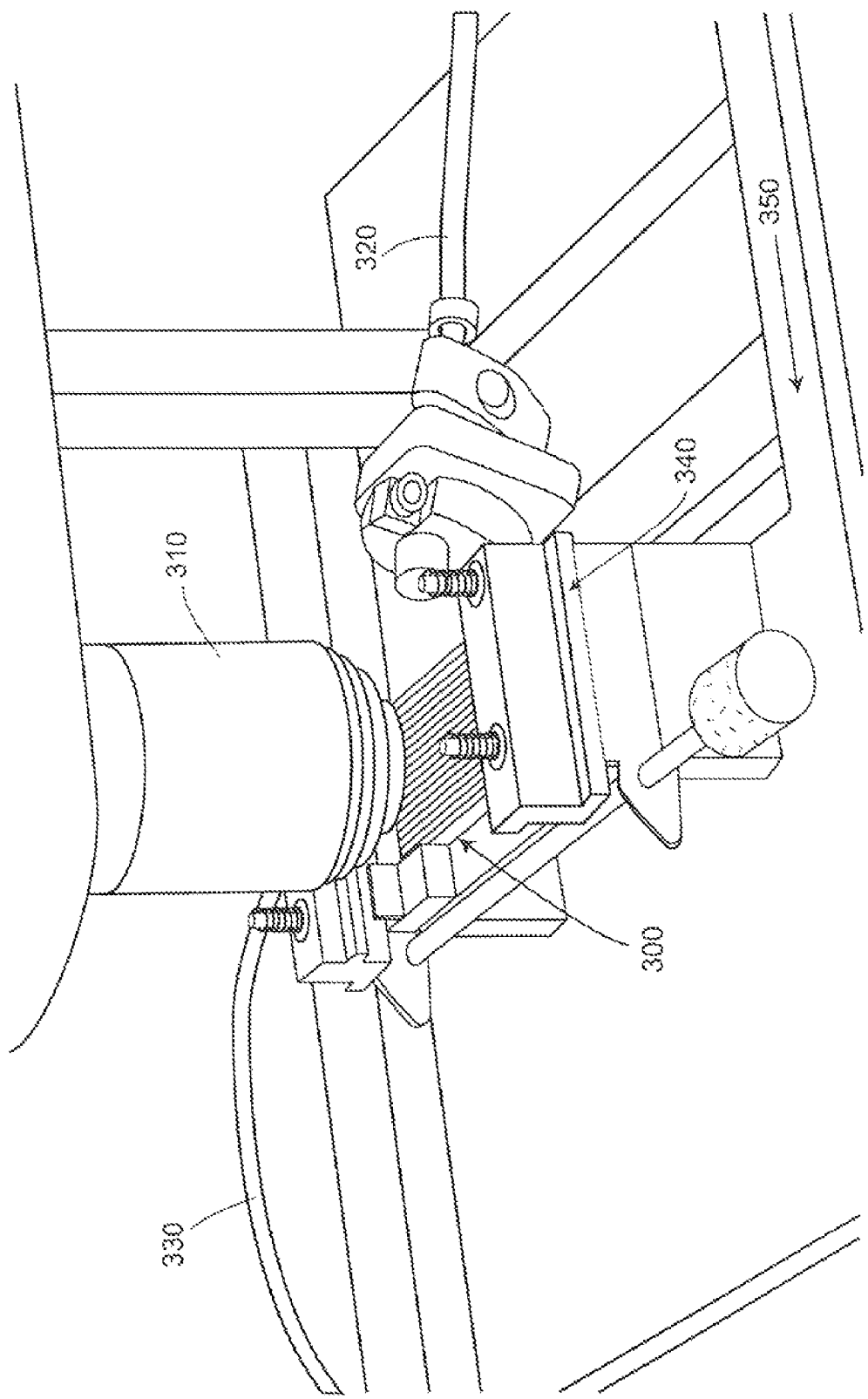

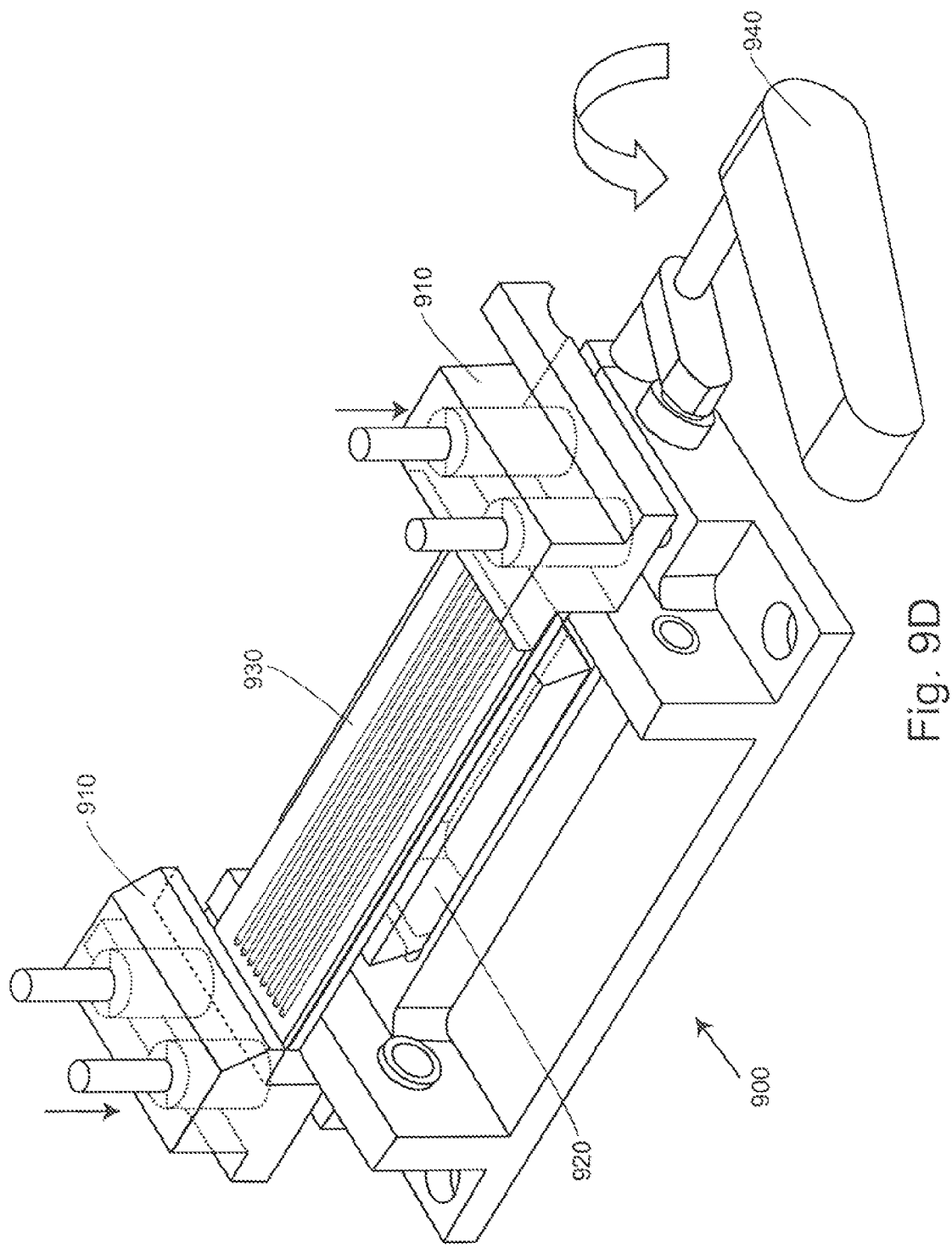

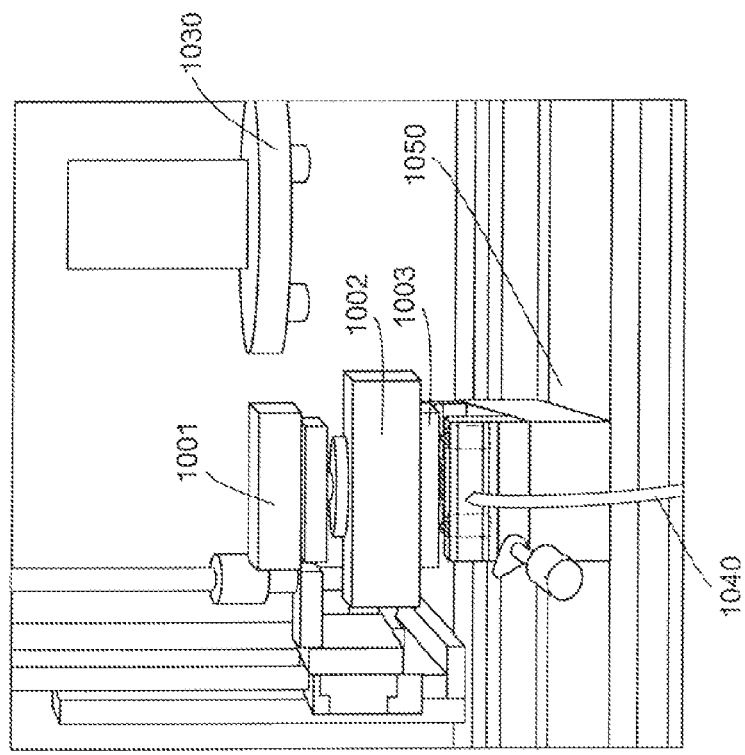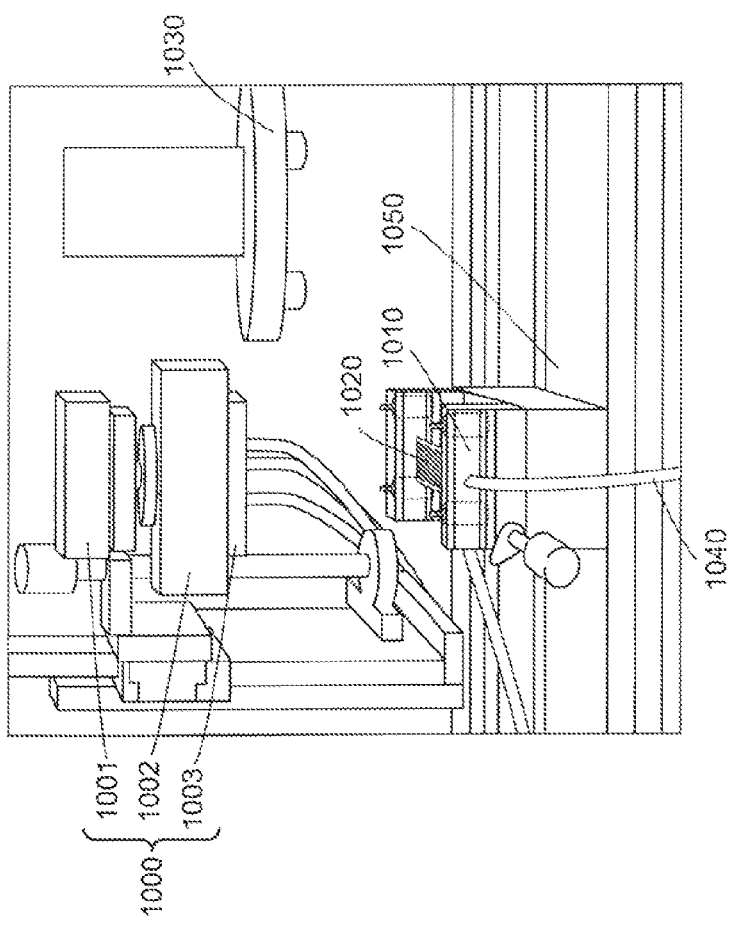
Fig. 10A

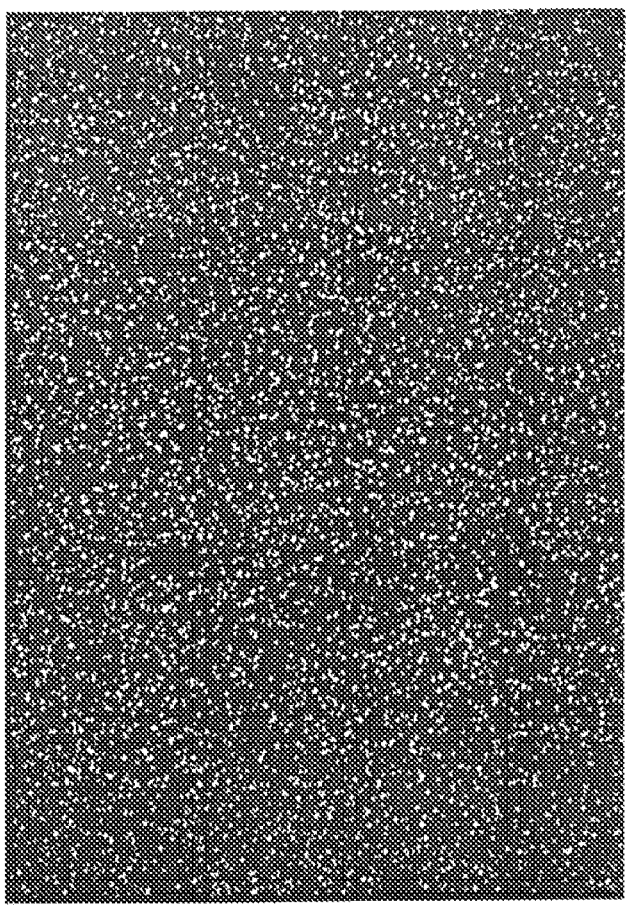
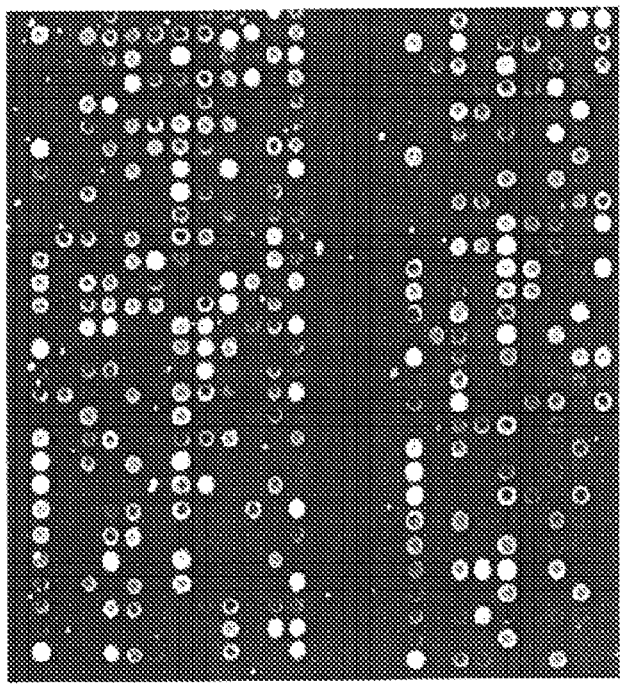
Fig. 31

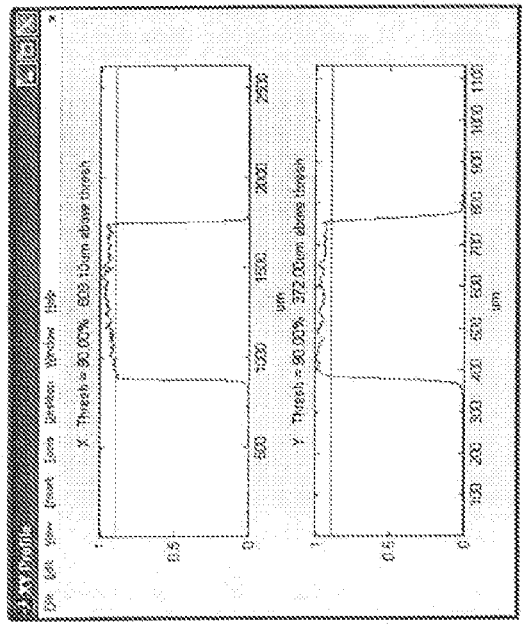
Fig. 35B
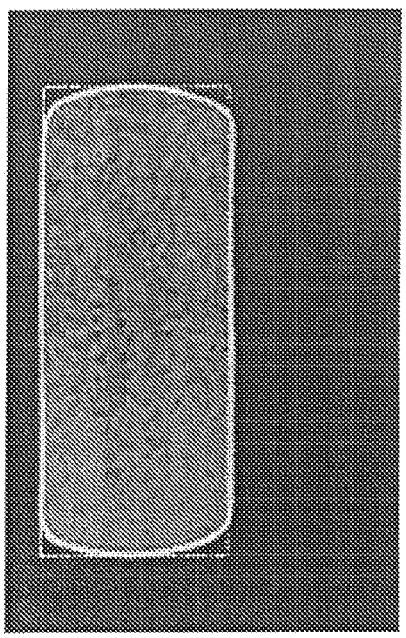
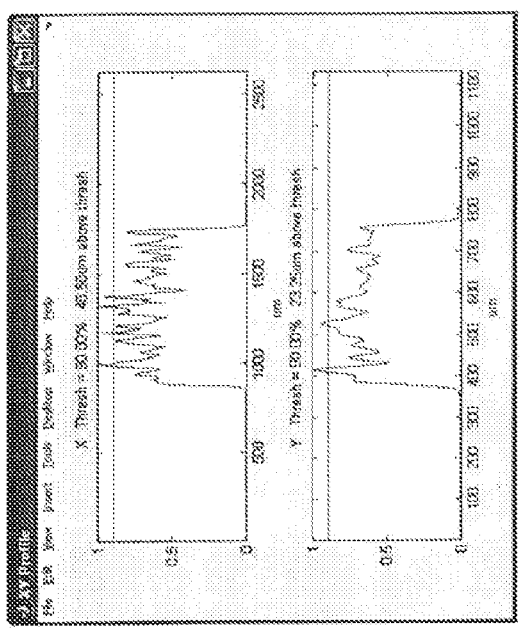
Fig. 35A
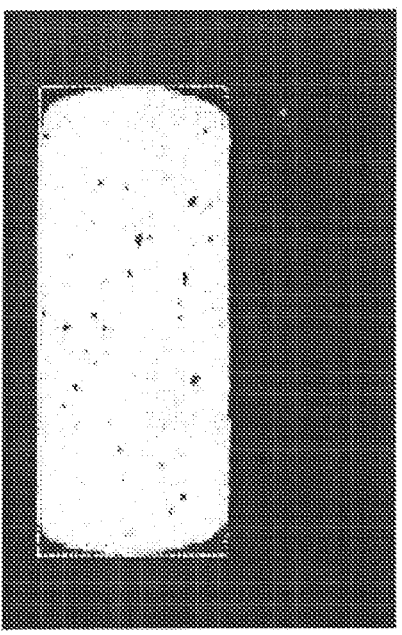

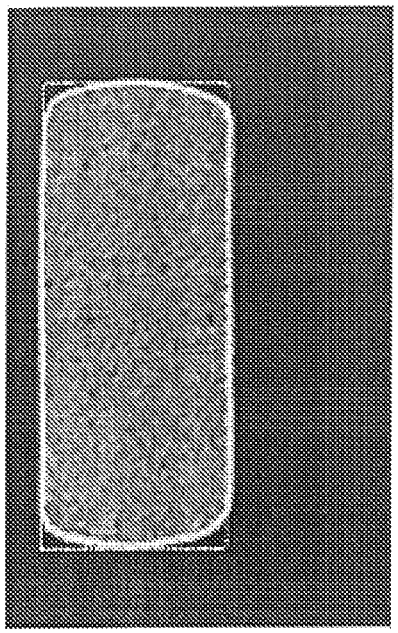
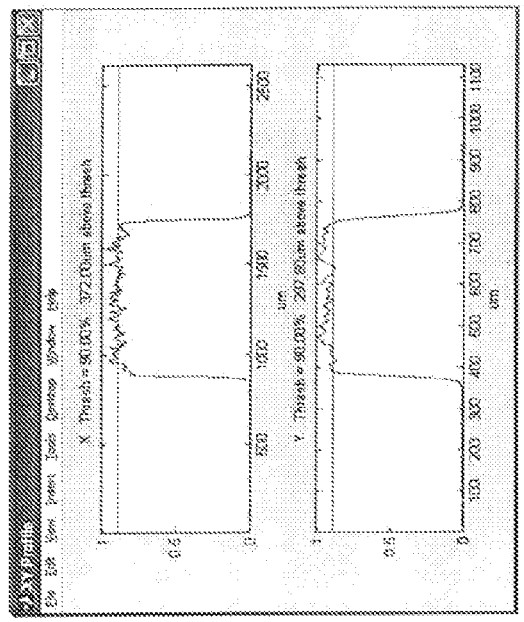
Fig. 35C
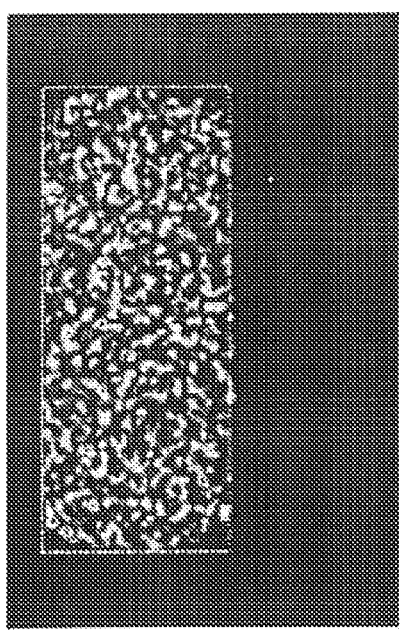
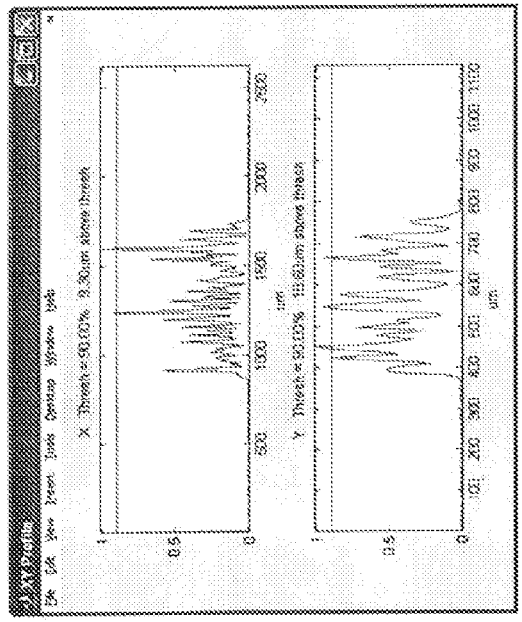
Fig. 35D

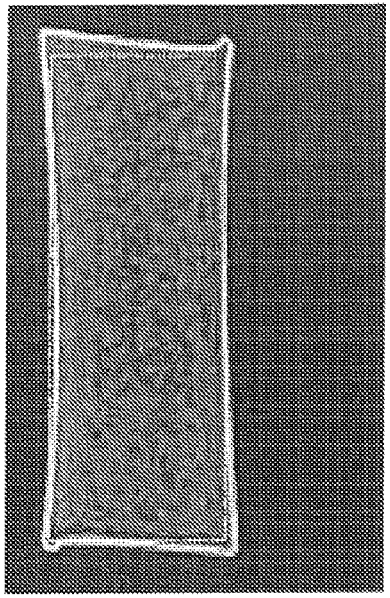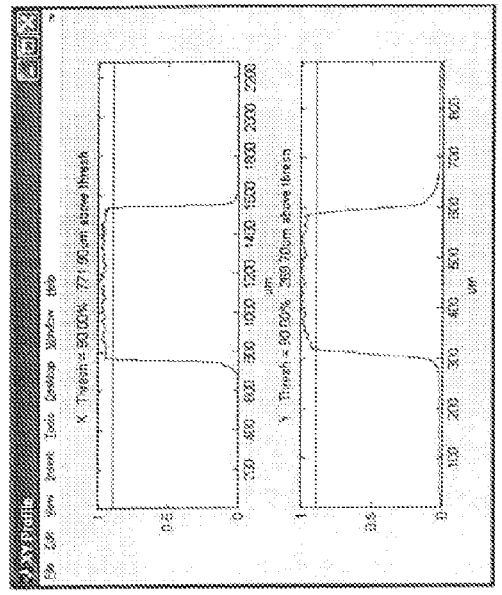
Fig. 35F
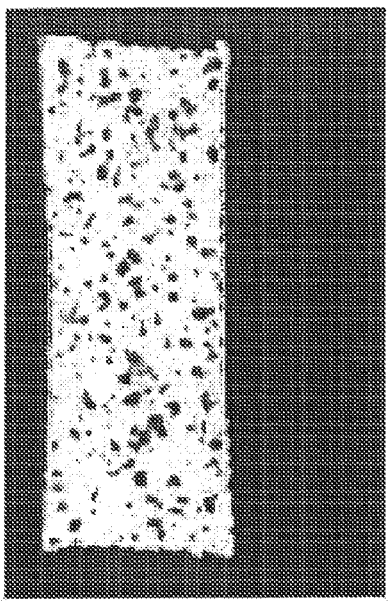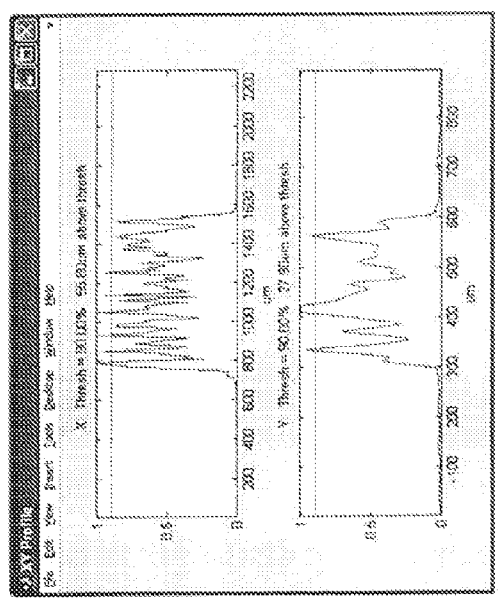
Fig. 35E

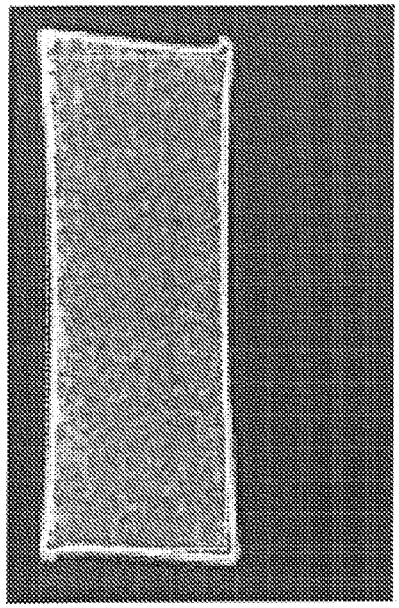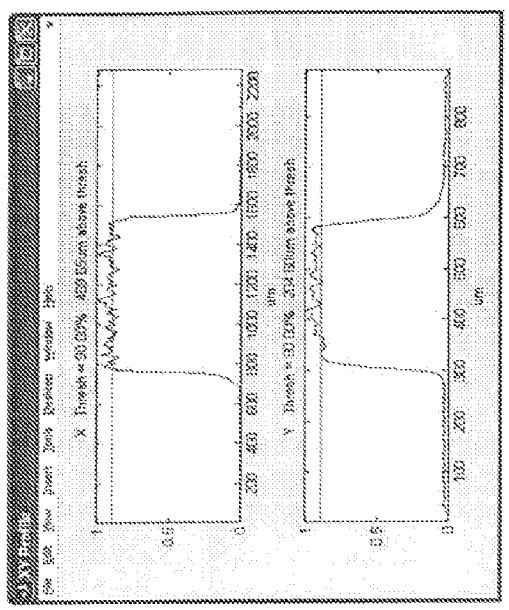
Fig. 35H
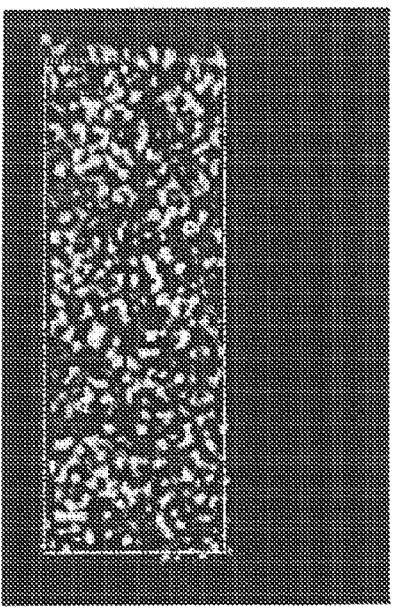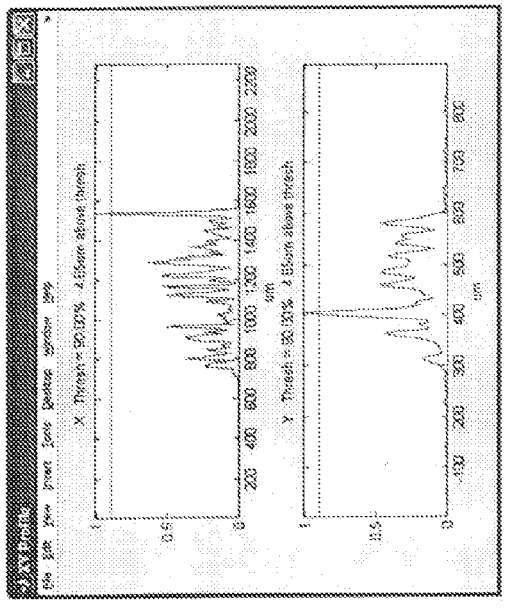
Fig. 35G

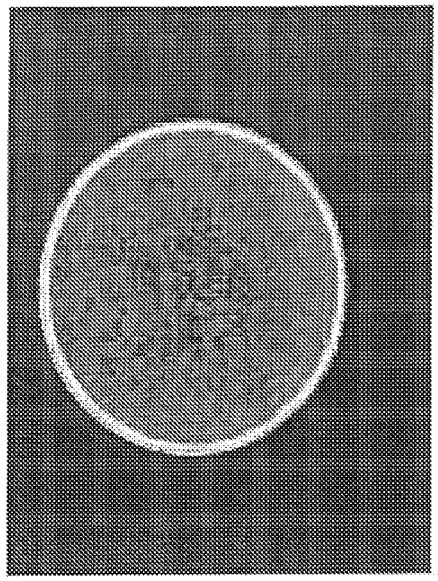
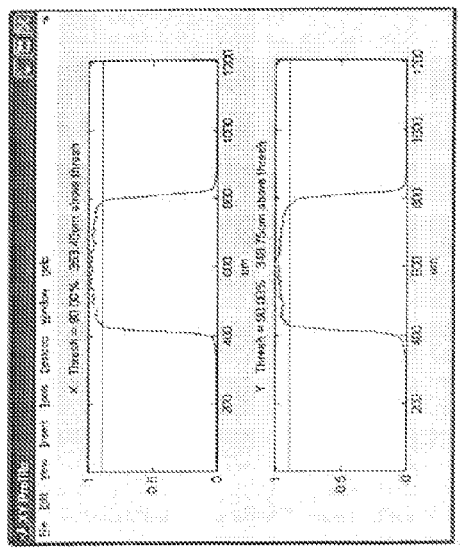
Fig. 35J
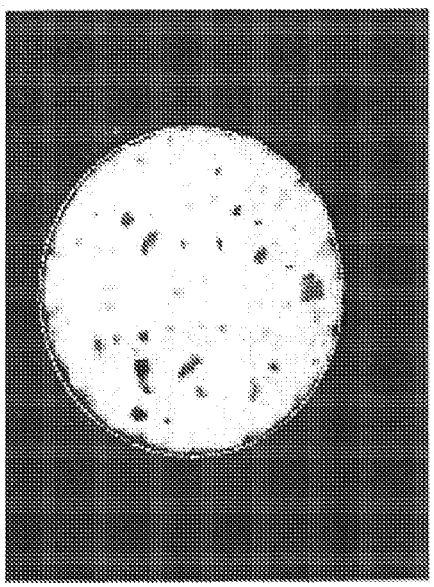
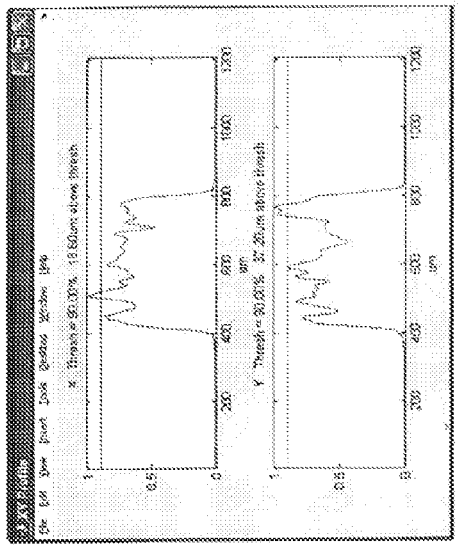
Fig. 35I

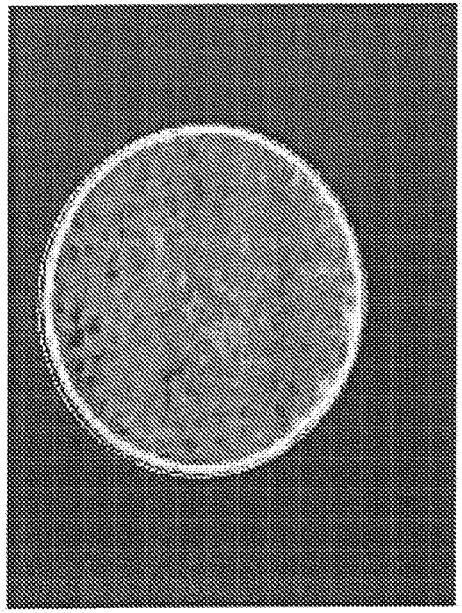
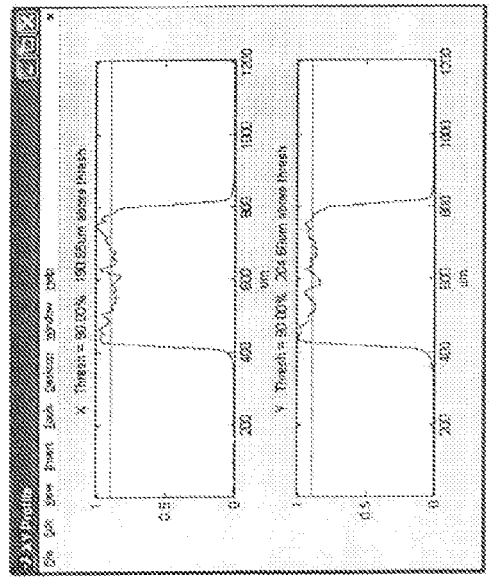
Fig. 35L
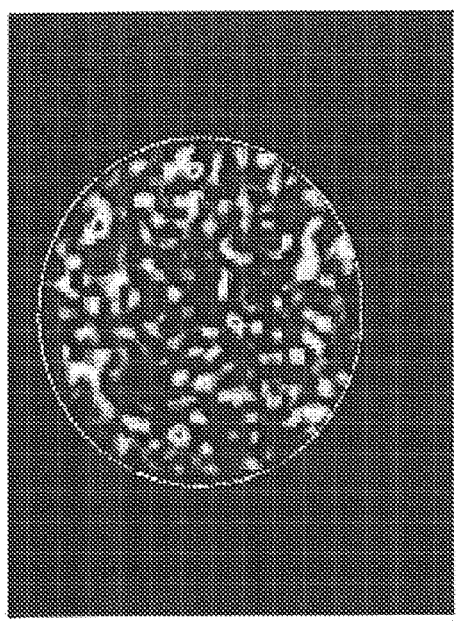
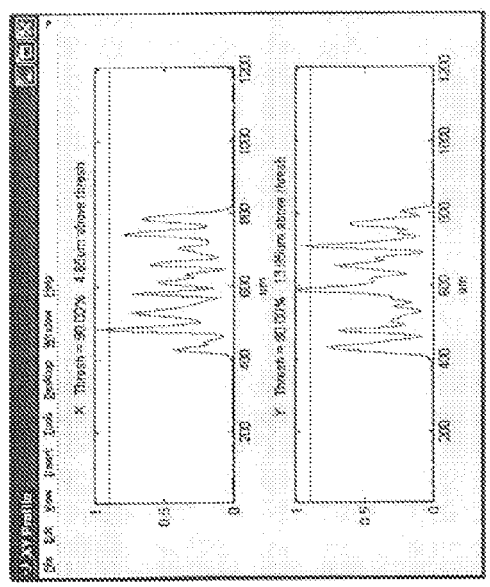
Fig. 35K

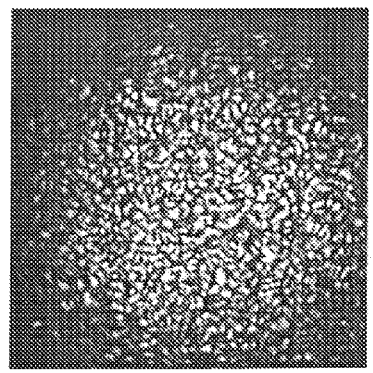
Fig. 41A
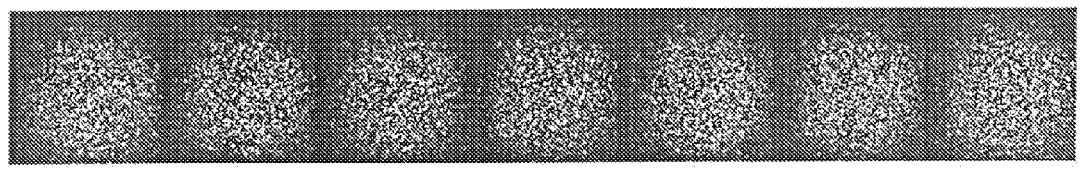
Fig. 41B
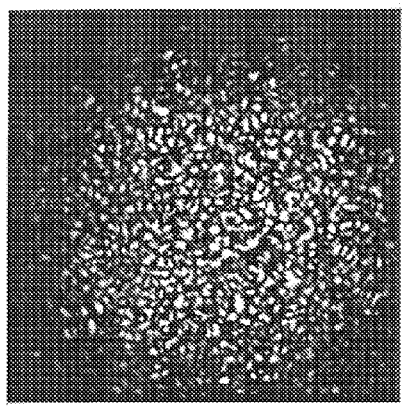 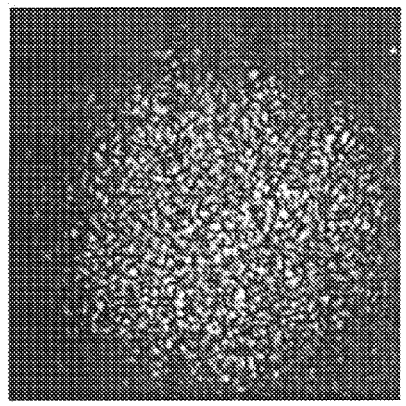
Fig. 41C　　　　　　　　Fig. 41D

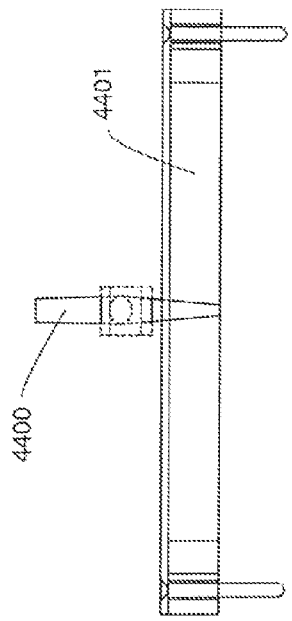
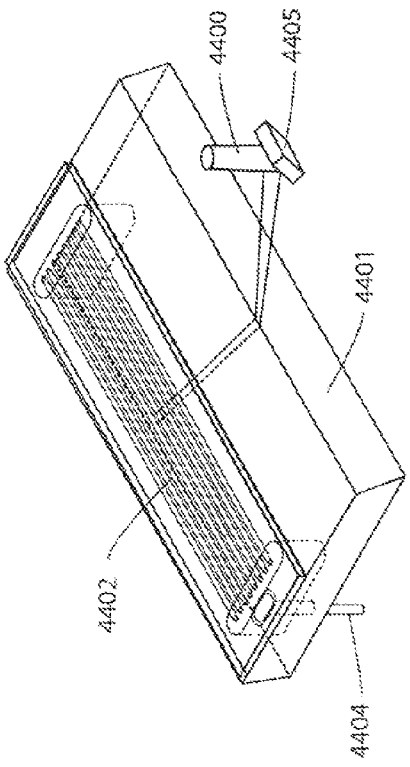
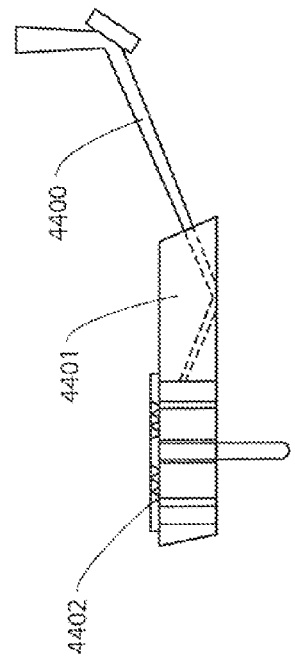
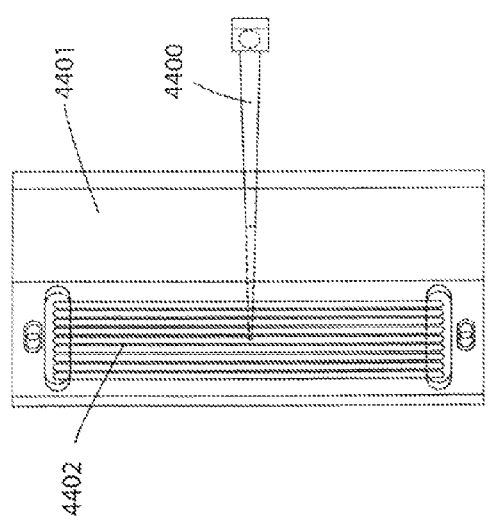
Fig. 44A
Fig. 44B
Fig. 44C
Fig. 44D

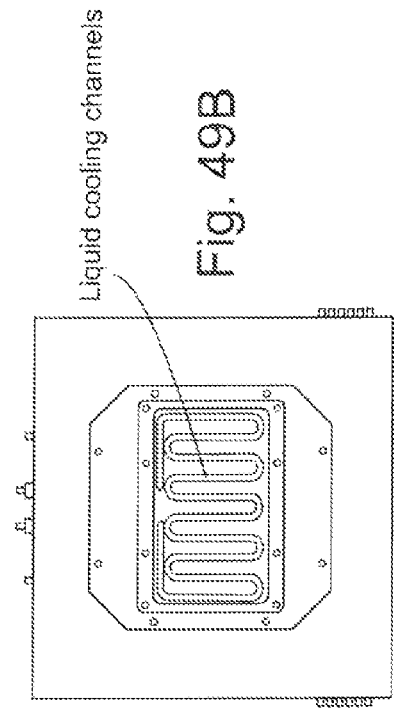
Fig. 49A
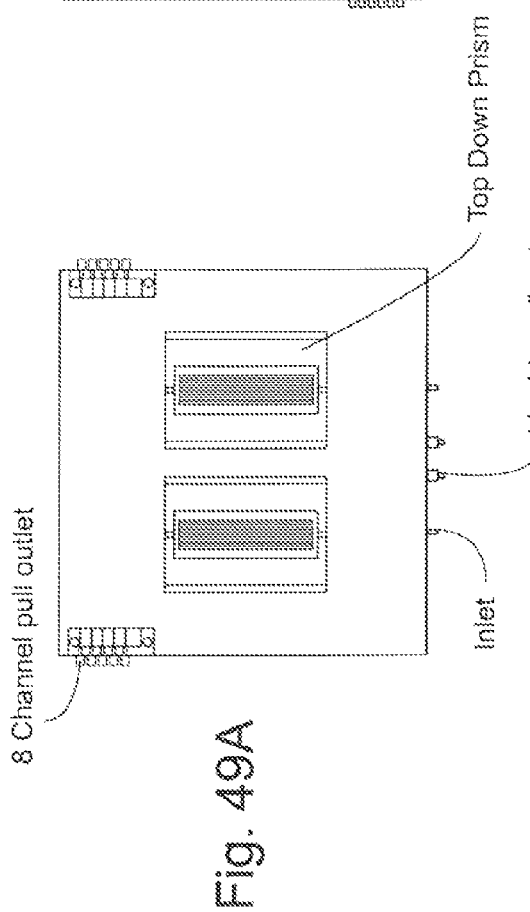
Fig. 49B
Fig. 49C
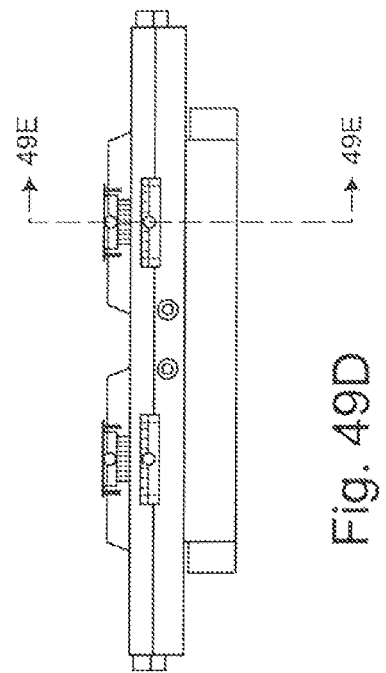
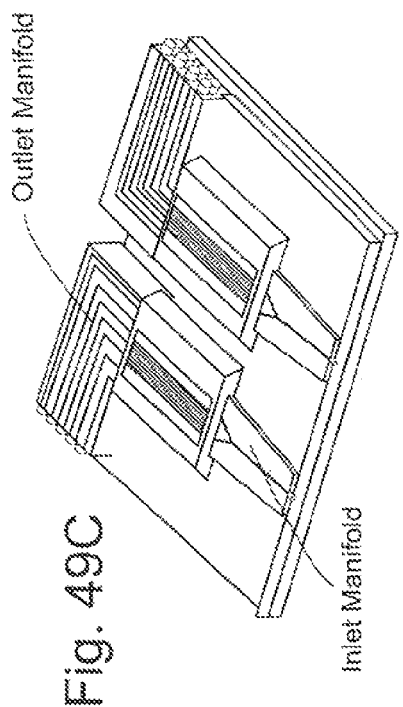
Fig. 49D

SYSTEMS AND DEVICES FOR SEQUENCE BY SYNTHESIS ANALYSIS

CROSS-REFERENCE TO RELATED APPLICATIONS

The present application claims priority to and is a national stage entry of International Patent Application No. PCT/US2007/007991, which claims priority to U.S. Provisional Patent Application Nos. 60/788,248, filed Mar. 31, 2006, and 60/795,368 filed Apr. 26, 2006, all of which are herein incorporated by reference in their entirety for all purposes.

FIELD OF THE INVENTION

The current invention relates to the field of nucleic acid sequencing. More specifically, the present invention provides systems and devices for sequence analysis of nucleic acids such as short DNA sequences from clonally amplified single-molecule arrays.

BACKGROUND OF THE INVENTION

Numerous recent advances in the study of biology have benefited from improved methods of analysis and sequencing of nucleic acids. For example, the Human Genome Project has determined the entire sequence of the human genome which is hoped to lead to further discoveries in fields ranging from treatment of disease to advances in basic science. While the "human genome" has been sequenced there are still vast amounts of genomic material to analyze, e.g., genetic variation between different individuals, tissues, additional species, etc.

Devices for DNA sequencing based on separation of fragments of differing length were first developed in the 1980s, and have been commercially available for a number of years. However, such technology involves running individual samples through capillary columns filled with polyacrylamide gels and is thus limited in throughput due to the time taken to run each sample. A number of new DNA sequencing technologies have recently been reported that are based on the massively parallel analysis of unamplified (WO00006770: *Proceedings of the National Academy of Sciences U.S.A.* 100, 3960-3964 (2003)) or amplified single molecules, either in the form of planar arrays (WO9844151) or on beads (WO04069849: *Nature*, 437, 376-380 (2005): *Science*, 309, 5741, 1728-1732 (2005); *Nat Biotechnol.* 6, 630-6344 (2000)).

The methodology used to analyze the sequence of the nucleic acids in such new sequencing techniques is often based on the detection of fluorescent nucleotides or oligonucleotides. The detection instrumentation used to read the fluorescence signals on such arrays is usually based on either epifluorescence or total internal reflection microscopy, for example as described in WO9641011, WO00006770 or WO02072892. Whilst total internal reflection microscopy has been used to image both single and amplified molecules of DNA on surfaces, a robust, reliable, four color DNA sequencing platform (e.g., comprising heating systems, fluidic controls, uniform illumination, control of the optical beam shape, an autofocus system, and hill software control of all components) is described herein for the first time.

There is a continuing need for better, more robust, and more economical devices and systems for fast reliable sequencing of nucleic acids. The current invention provides these and other benefits which will be apparent upon examination of the current specification, claims, and figures.

SUMMARY OF THE INVENTION

In various aspects herein, the invention comprises systems and devices for sequencing one or more polynucleotide. The systems can be used to image planar substrates, wherein the substrates can comprise unamplified single molecules, amplified single molecules, one or more collections of arrayed beads, or various combinations thereof. When used for sequencing, the systems can optionally comprise a planar solid substrate having one or more polynucleotides displayed thereon, e.g. either directly attached, or attached to beads that are optionally arrayed on the substrate; a fluid direction system that controllably moves various reagents (e.g., buffers, enzymes, fluorescently labeled nucleotides or oligonucleotides, etc.) into contact with the polynucleotides; a temperature control system that regulates the temperature of the substrate and/or of the reagents; an optical system for obtaining total internal reflection illumination of the substrate with a uniform beam footprint (where the shape of the footprint is optionally controlled), a light source (e.g., one comprising one or more lasers) for exciting the fluorescent moiet(ies); a detector component (e.g., a CCD camera and objective lenses, etc.) that is proximal to the substrate and which captures and detects fluorescence from the excited moiet(ies); a computer, connected to the detector, which has instruction sets for controlling the various components of the system, acquiring fluorescence data from the detector and optionally for determining sequence of the polynucleotide from the fluorescence data.

In some such embodiments, the substrates can be moved away from the detector in order to interact with the temperature control system, thus, regulating the temperature of the substrate (e.g., to allow polymerase reactions to proceed, etc.). In such embodiments, the system can comprise a scanning stage or moving platform that is optionally computer controlled. The heating device can be a computer controlled Peltier device or other heating/cooling component that moves in relation to the scanning stage, or the stage can optionally move to ensure that the Peltier is in contact with the substrate.

In the various embodiments herein, the substrate can comprise a flowcell. Flowcells can have one or more fluidic channel in which the polynucleotide is displayed (e.g., wherein the polynucleotides are directly attached to the flowcell or wherein the polynucleotides are attached to one or more beads arrayed upon the flowcell) and can be comprised of glass, silicon, plastic, or various combinations thereof.

In typical embodiments, the reagents include components to synthesize a second sequence complementary to the one or more polynucleotides. The synthesis can be performed using labeled nucleotides, which can be added individually or as a mixture of nucleotides, or as labeled oligonucleotides. In the case of labeled oligonucleotides, the identity of one or more bases complementary to the labeled oligonucleotide can be determined. The labeled nucleotides can take the form of fluorescently labeled triphosphates, which can contain a blocking moiety to control the addition and ensure a single nucleotide is added to each polynucleotide. The fluorophore can be attached to the blocking moiety, which can be located at the 3' position of the sugar, or can be attached through the nucleotide base through a linker that can optionally be cleaved using the same conditions as removal of the blocking moiety. The linker and blocking moiety may be cleaved using the same reagents.

In various embodiments herein, the Total Internal Reflection (TIRF) system can comprise, e.g., a lamp or a laser. The system can comprise more than one excitation lasers that can be coupled through a fiberoptic device. Such lasers can illuminate at least part of the same area. (i.e., overlap). The TIRF lasers herein also optionally comprise a shaking, vibrating, waveplate modulated, or piezo-electric actuator squeezed fiber mode scrambler to make the optical intensity substantially uniform over an entire illumination footprint of the laser. A number of mechanisms for controlling the illumination intensity and uniformity are described herein. The shape of the fiber also can be used to control the shape of the illumination footprint.

The detector component in the various embodiments herein can comprise one or more objective lenses, additional tube lenses, an autofocus system that adjusts either the stage position and/or the position of the objective lens(es) to ensure the substrate remains in focus, optical filter(s) appropriate to transmit the emission wavelength of the fluorophores and block the light from the excitation source, and a system for recording the fluorescence emission from the fluorophores, for example a charge coupled device (CCD) or similar camera.

These and other features of the invention will become more fully apparent when the following detailed description is read in conjunction with the accompanying figures and claims.

BRIEF DESCRIPTION OF THE DRAWINGS

FIG. 2, displays a photograph of an exemplary system of the invention shown without an enclosing chassis or covering.

FIG. 3, displays a photograph of an exemplary flowcell, lens objective, and fiber optic laser arrangement within a system of the invention.

FIGS. 30-32, display outlines of nucleic acid clusters and their sequencing with the systems/devices of the invention.

FIG. 35, Panels A-L display the effects of various mode scrambling schemes on emergent light from a number of different optical fibers.

FIG. 41, Panels A-D show photographs of an illuminated footprint area from a multimode optical fiber and results from mixing of optical modes through use of waveplates.

DETAILED DESCRIPTION

The present invention comprises systems and devices to analyze a large number of different nucleic acid sequences from, e.g., clonally amplified single-molecule DNA arrays in flowcells, or from an array of immobilized beads. The systems herein are optionally useful in, e.g., sequencing for comparative genomics (such as for genotyping, SNP discovery, BAC-end sequencing, chromosome breakpoint mapping, and whole genome sequence assembly), tracking gene expression, micro RNA sequence analysis, epigenomics (e.g., with methylation mapping DNAseI hypersensitive site mapping or chromatin immunoprecipitation), and aptamer and phage display library characterization. Of course, those of skill in the art will readily appreciate that the current invention is also amenable to use for myriad other sequencing applications. The systems herein comprise various combinations of optical, mechanical, fluidic, thermal, electrical, and computing devices/aspects which are described more fully below. Also, even though in certain embodiments the invention is directed towards particular configurations and/or combinations of such aspects, those of skill in the art will appreciate that not all embodiments necessarily comprise all aspects or particular configurations (unless specifically stated to do so).

Figure 1:
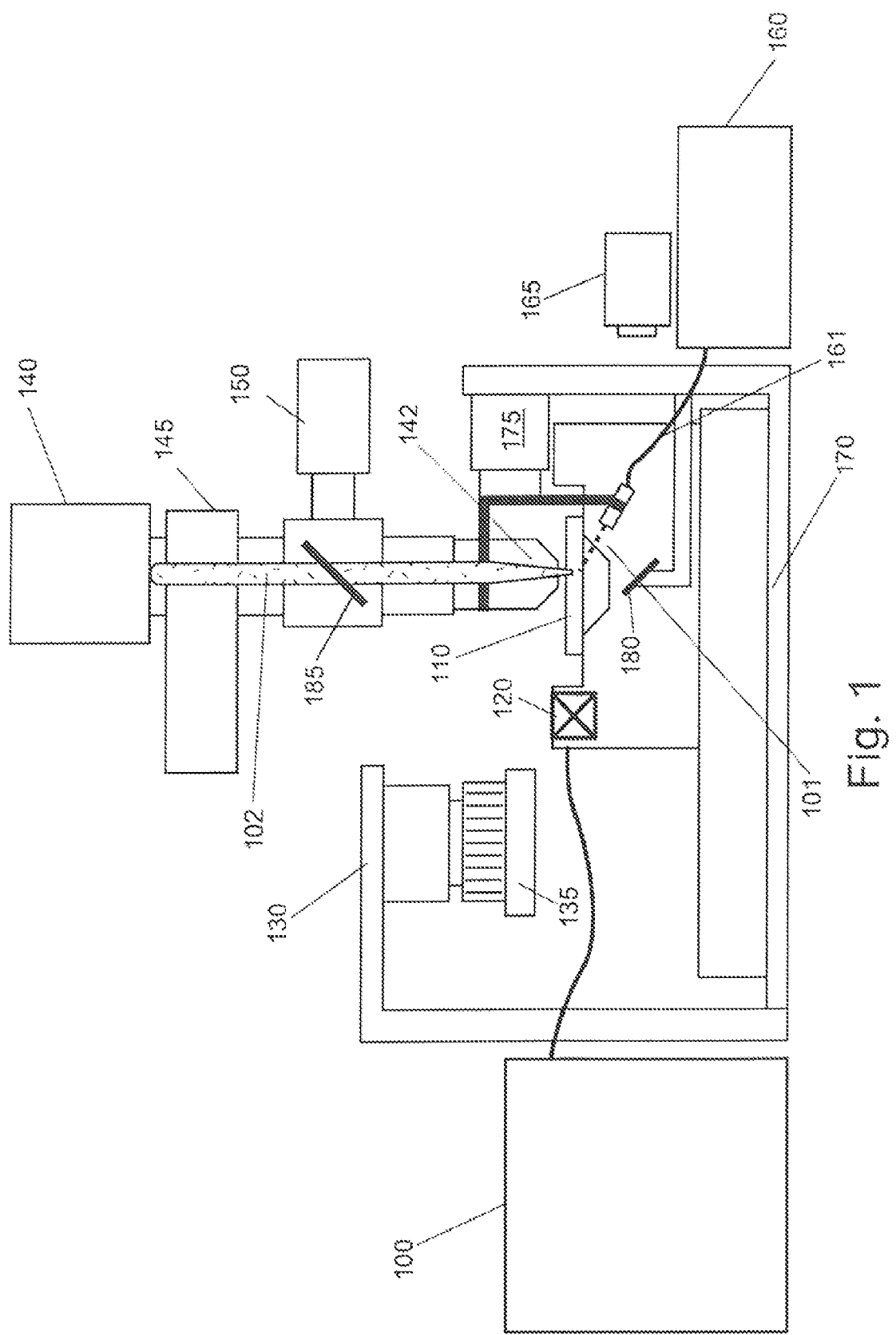
FIG. 1, displays a generalized overview of the major components of an exemplary system of the invention.

In brief, the general aspects of the invention are outlined in FIG. 1 which shows an exemplary TIRF imaging configuration of a backlight design embodiment. As can be seen in FIG. 1, fluid delivery module or device 100 directs the flow of reagents (e.g., fluorescent nucleotides, buffers, enzymes, cleavage reagents, etc.) to (and through) flowcell 110 and waste valve 120. In particular embodiments, the flowcell comprises clusters of nucleic acid sequences (e.g., of about 200-1000 bases in length) to be sequenced which are optionally attached to the substrate of the flowcell, as well as optionally other components. The flowcell can also comprise an array of beads, where each bead optionally contains multiple copies of a single sequence. The preparation of such beads can be performed according to a variety of techniques, for example as described in U.S. Pat. No. 6,172,218 or WO04069849 (Bead emulsion nucleic acid amplification).

The system also comprises temperature station actuator 130 and heater/cooler 135, which can optionally regulate the temperature of conditions of the fluids within the flowcell. As explained below, various embodiments can comprise different configurations of the heating/cooling components. The flowcell is monitored, and sequencing is tracked, by camera system 140 (e.g., a CCD camera) which can interact with various filters within filter switching assembly 145, lens objective 142, and focusing laser/focusing laser assembly 150. Laser device 160 (e.g., an excitation laser within an assembly optionally comprising multiple lasers) acts to illuminate fluorescent sequencing reactions within the flowcell via laser illumination through fiber optic 161 (which can optionally comprise one or more re-imaging lenses, a fiber optic mounting, etc. Low watt lamp 165, mirror 180 and reverse dichroic 185 are also presented in the embodiment shown. See below. Additionally, mounting stage 170, allows for proper alignment and movement of the flowcell, temperature actuator, camera, etc. in relation to the various components of the invention. Focus (z-axis) component 175 can also aid in manipulation and positioning of various components (e.g., a lens objective). Such components are optionally organized upon a framework and/or enclosed within a housing structure. It will be appreciated that the illustrations herein are of exemplary embodiments and are not necessarily to be taken as limiting. Thus, for example, different embodiments can comprise different placement of components relative to one another (e.g., embodiment A comprises a heater/cooler as in FIG. 1, while embodiment B comprises a heater/cooler component beneath its flowcell, etc.).

DEFINITIONS

Before describing the present invention in detail, it is to be understood that the invention herein is not limited to use with particular nucleic acids or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the context clearly dictates otherwise. Thus, for example, reference to "a flowcell" optionally includes a combination of two or more flowcells, and the like.

As used herein, the terms "polynucleotide" or "nucleic acids" refer to deoxyribonucleic acid (DNA), but where appropriate the skilled artisan will recognize that the systems and devices herein can also be utilized with ribonucleic acid (RNA). The terms should be understood to include, as equivalents, analogs of either DNA or RNA made from nucleotide analogs. The terms as used herein also encompasses cDNA, that is complementary, or copy, DNA produced from an RNA template, for example by the action of reverse transcriptase.

The single stranded polynucleotide molecules sequenced by the systems and devices herein can have originated in single-stranded form, as DNA or RNA or have originated in double-stranded DNA (dsDNA) form (e.g. genomic DNA fragments, PCR and amplification products and the like). Thus a single stranded polynucleotide may be the sense or antisense strand of a polynucleotide duplex. Methods of preparation of single stranded polynucleotide molecules suitable for use in the method of the invention using standard techniques are well known in the art. The precise sequence of the primary polynucleotide molecules is generally not material to the invention, and may be known or unknown. The single stranded polynucleotide molecules can represent genomic DNA molecules (e.g., human genomic DNA) including both intron and exon sequences (coding sequence), as well as non-coding regulatory sequences such as promoter and enhancer sequences.

In certain embodiments, the nucleic acid to be sequenced through use of the current invention is immobilized upon a substrate (e.g., a substrate within a flowcell or one or more beads upon a substrate such as a flowcell, etc.). The term "immobilized" as used herein is intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to the support under conditions in which it is intended to use the support, for example in applications requiring nucleic acid sequencing.

The term "solid support" (or "substrate" in certain usages) as used herein refers to any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In many embodiments, the solid support is a glass surface (e.g., the planar surface of a flowcell channel). In certain embodiments the solid support may comprise an inert substrate or matrix which has been "functionalized," for example by the application of a layer or coating of an intermediate material comprising reactive groups which permit covalent attachment to molecules such as polynucleotides. By way of non-limiting example such supports can include polyacrylamide hydrogels supported on an inert substrate such as glass. In such embodiments the molecules (polynucleotides) can be directly covalently attached to the intermediate material (e.g. the hydrogel) but the intermediate material can itself be non-covalently attached to the substrate or matrix (e.g. the glass substrate). Covalent attachment to a solid support is to be interpreted accordingly as encompassing this type of arrangement.

System Overview

As indicated above, the present invention comprises novel systems and devices for sequencing nucleic acids. As will be apparent to those of skill in the art, references herein to a particular nucleic acid sequence may, depending on the context, also refer to nucleic acid molecules which comprise such nucleic acid sequence. Sequencing of a target fragment means that a read of the chronological order of bases is established. The bases that are read do not need to be contiguous, although this is preferred, nor does every base on the entire fragment have to be sequenced during the sequencing. Sequencing can be carried out using any suitable sequencing technique, wherein nucleotides or oligonucleotides are added successively to a free 3' hydroxyl group, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to, the strands on the surface are also amenable to use with the systems and devices of the invention.

In certain embodiments, the current invention utilizes sequencing-by-synthesis (SBS). In SBS, four fluorescently labeled modified nucleotides are used to sequence dense clusters of amplified DNA (possibly millions of clusters) present on the surface of a substrate (e.g., a flowcell). The inventors and coworkers have described various additional aspects regarding SBS procedures and methods which can be utilized with the systems and devices herein. See, e.g., WO04018497, WO04018493 and U.S. Pat. No. 7,057,026 (nucleotides), WO05024010 and WO06120433 (polymerases), WO05065814 (surface attachment techniques), and WO 9844151, WO06064199 and WO07010251, the contents of each of which are incorporated herein by reference in their entirety.

In particular uses of the systems/devices herein the flowcells containing the nucleic acid samples for sequencing are placed within the appropriate flowcell holder of the present invention (various embodiments of which are described herein). The samples for sequencing can take the form of single molecules, amplified single molecules in the form of clusters, or beads comprising molecules of nucleic acid. The nucleic acids are prepared such that they comprise an oligonucleotide primer adjacent to an unknown target sequence. To initiate the first SBS sequencing cycle, one or more differently labeled nucleotides, and DNA polymerase, etc., are flowed into/through the flowcell by the fluid flow subsystem (various embodiments of which are described herein). Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Where the four nucleotides are mixed together, the polymerase is able to select the correct base to incorporate and each sequence is extended by a single base. In such methods of using the systems of the invention, the natural competition between all four alternatives leads to higher accuracy than wherein only one nucleotide is present in the reaction mixture (where most of the sequences are therefore not exposed to the correct nucleotide). Sequences where a particular base is repeated one after another (e.g., homopolymers) are addressed like any other sequence and with high accuracy.

The fluid flow subsystem also flows the appropriate reagents to remove the blocked 3' terminus (if appropriate) and the fluorophore from each incorporated base. The substrate can be exposed either to a second round of the four blocked nucleotides, or optionally to a second round with a different individual nucleotide. Such cycles are then repeated and the sequence of each cluster is read over the multiple chemistry cycles. The computer aspect of the current invention can optionally align the sequence data gathered from each single molecule, cluster or bead to determine the sequence of longer polymers, etc. Alternatively, the image processing and alignment can be performed on a separate computer.

The heating/cooling components of the system regulate the reaction conditions within the flowcell channels and reagent storage areas/containers (and optionally the camera, optics, and/or other components), while the fluid flow components allow the substrate surface to be exposed to suitable reagents for incorporation (e.g., the appropriate fluorescently labeled nucleotides to be incorporated) while unincorporated reagents are rinsed away. An optional movable stage upon which the flowcell is placed allows the flowcell to be brought into proper orientation for laser (or other light) excitation of the substrate and optionally moved in relation to a lens objective to allow reading of different areas of the substrate. Additionally, other components of the system are also optionally movable/adjustable (e.g., the camera, the lens objective, the heater/cooler, etc.). During laser excitation, the image/location of emitted fluorescence from the nucleic acids on the substrate is captured by the camera component, thereby, recording the identity, in the computer component, of the first base for each single molecule, cluster or bead.

FIG. 2 displays a photograph of an exemplary arrangement of a system of the invention. As can be seen, the system can be divided into several basic groupings, e.g., area 200 comprising fluidics and reagent storage (including pumps and motors or the like for producing and regulating fluid flow, heaters/coolers for proper reagent temperatures, etc.), area 210 comprising flowcell and detection (including one or more cameras or similar devices, one or more lasers or other light sources, one or more appropriate optical filters and lenses, a temperature control actuator, e.g., with Peltier heating/cooling for control of the temperature conditions of the flowcell, a movable staging platform and motors controlling such to correctly position the various devices/components within the system), and area 220 comprising a computer module (including memory and a user interface such as a display panel and keyboard, etc.).

FIG. 3 shows a photograph of a flowcell (flowcell 300) placed within an exemplary system. A laser coupled through optical fiber 320 is positioned to illuminate the flowcell (which contains the nucleic acid samples to be sequenced) while an objective lens component (component 310) captures and monitors the various fluorescent emissions once the fluorophores are illuminated by a laser or other light. Also as can be seen in FIG. 3, reagents are flowed through the flowcell through one or more tubes (tube 330) which connect to the appropriate reagent storage, etc. The flowcell in FIG. 3 is placed within flowcell holder 340 (which is, in turn, placed upon movable staging area 350). The flowcell holder keeps the flowcell secure in the proper position in relation to the laser, the prism (which directs laser illumination onto the imaging surface), and the camera system, while the sequencing occurs. Other flowcells and flowcell configurations are set forth below.

The various embodiments of the current invention present several novel features (again, it will be appreciated that not all features are necessarily present in all embodiments unless specifically stated to be so). For example, the systems herein can use two excitation lasers coupled through a fiberoptic device to ensure that they illuminate the same area (i.e. that the illuminated areas, or footprints, of the lasers overlap). Additionally, the current invention can contain a shaking, squeezed, or waveplate modulated fiber (mode scrambler) such that the optical intensity from a multimode beam is made uniform over the whole illumination footprint. The shape of the fiber may be adjusted, for example to be square or rectangular, such that the shape of the illumination can be matched to the shape of the data collection device (e.g., a CCD with square pixels). Also, in certain embodiments, a single laser excites two fluorophores, one with a narrow emission filter near the wavelength, and one with a wider band emission filter at longer wavelength. Such arrangement normalizes the relative intensities of the two dyes (with the same bandwidth filters, the dye further from the laser wavelength would be much weaker). The embodiments herein also can comprise a moving stage such that the chemistry (which requires heating and cooling) can happen on the same instrument, but out of the optical train. The systems herein also often contain an autofocus system to allow automated imaging of many tiles, and contain a fluidics system for performing on-line fluidic changes. The individual components of the system/device (e.g., light source, camera, etc.) can optionally each have its own power source or supply or can optionally all be powered via one source. As will be appreciated, while the components herein are often described in isolation or in relation to only one or two other components, that the various components in the embodiments are typically operably and/or functionally connected and work together in the systems/devices herein.

Flowcells

In various embodiments, the systems herein comprise one or more substrates upon which the nucleic acids to be sequenced are bound, attached or associated. See, e.g., WO 9844151 or WO0246456. In certain embodiments, the substrate is within a channel or other area as part of a "flowcell." The flowcells used in the various embodiments of the invention can comprise millions of individual nucleic acid clusters, e.g., about 2-8 million clusters per channel. Each of such clusters can give read lengths of at least 25 bases for DNA sequencing and 20 bases for gene expression analysis. The systems herein can generate a gigabase (one billion bases) of sequence per run (e.g., 5 million nucleic acid clusters per channel, 8 channels per flowcell, 25 bases per polynucleotide).

Figure 4A:
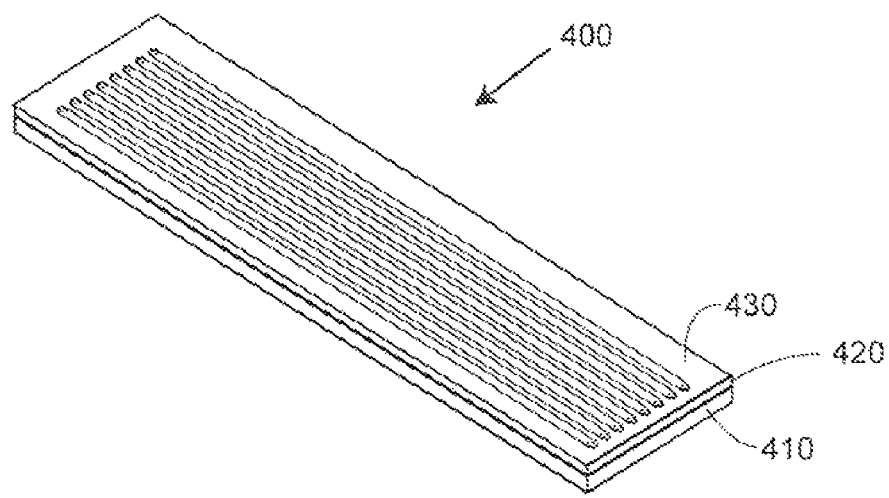
FIG. 4, Panels A-D show exemplary configurations of flowcells.
Figure 4B:
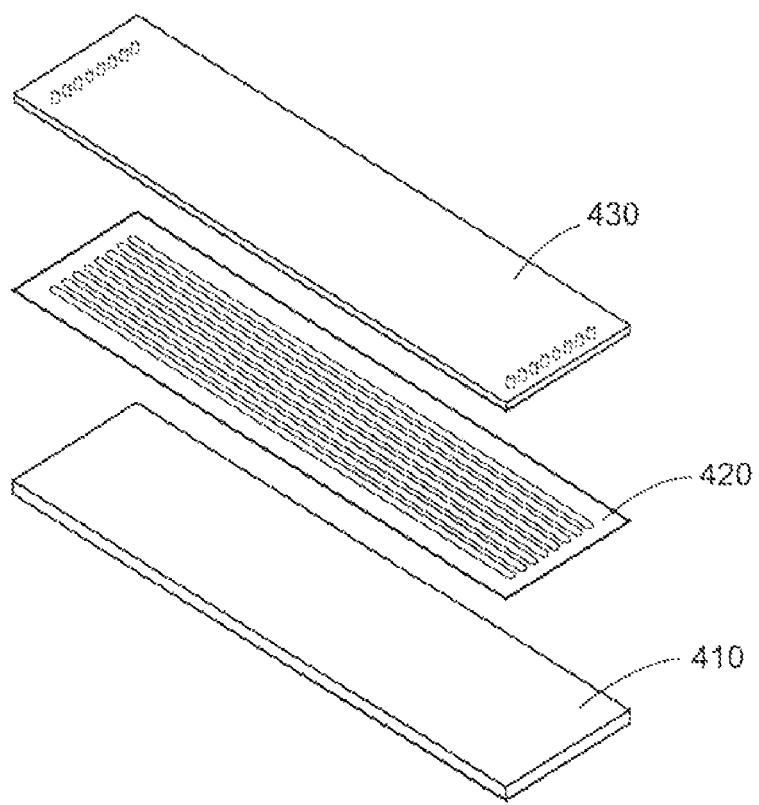

FIGS. 4A and 4B display one exemplary embodiment of a flowcell. As can be seen, the particular flowcell embodiment, flowcell 400, comprises base layer 410 (e.g., of borosilicate glass 1000 μm in depth), channel layer 420 (e.g., of etched silicon 100 μm in depth) overlaid upon the base layer, and cover, or top, layer 430 (e.g., 300 μm in depth). When the layers are assembled together, enclosed channels are formed having inlet/outlets at either end through the cover. As will be apparent from the description of additional embodiments below, some flowcells can comprise openings for the channels on the bottom of the flowcell.

The channeled layer can optionally be constructed using standard photolithographic methods, with which those of skill in the art will be familiar. One such method which can be used in the current invention, involves exposing a 100 μm layer of silicon and etching away the exposed channel using Deep Reactive Ion Etching or wet etching.

Figure 4C:
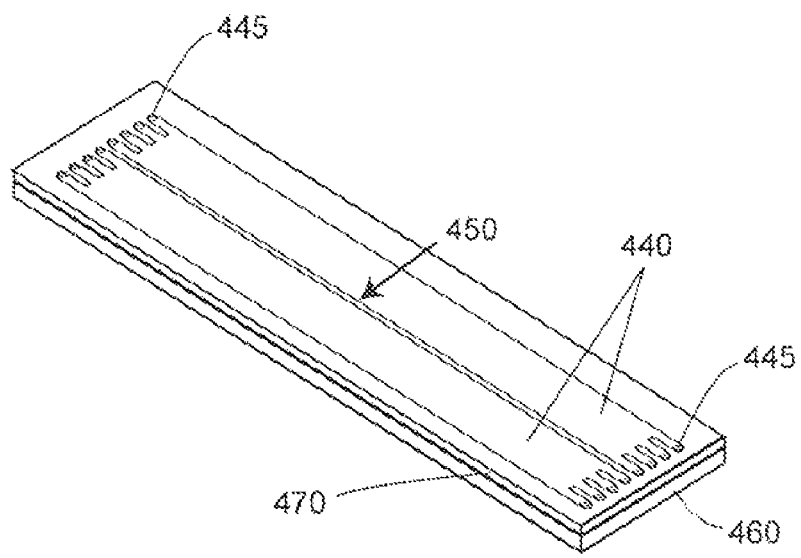
Figure 4D:
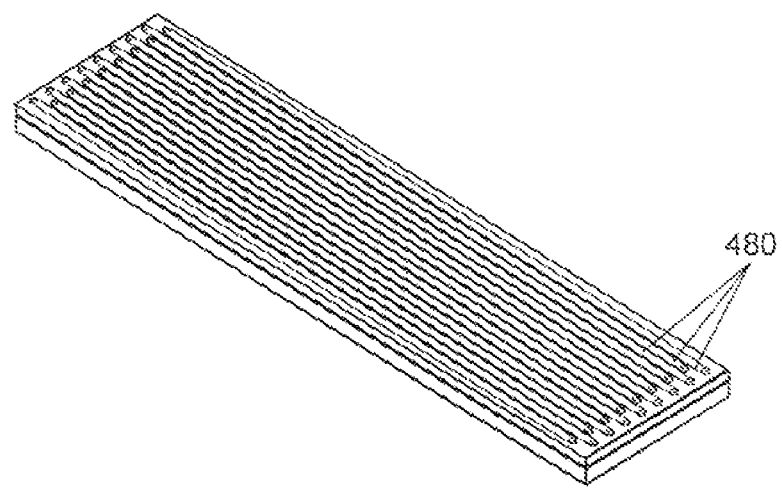

It will be appreciated that while particular flowcell configurations are present herein, such configurations should not necessarily be taken as limiting. Thus, for example, various flowcells herein can comprise different numbers of channels (e.g., 1 channel, 2 or more channels, 4 or more channels, or 6, 8, 10, 16 or more channels, etc. Additionally, various flowcells can comprise channels of different depths and/or widths (different both between channels in different flowcells and different between channels within the same flowcell). For example, while the channels formed in the cell in FIG. 4B are 100 μm deep, other embodiments can optionally comprise channels of greater depth (e.g., 500 μm) or lesser depth (e.g., 50 μm). Additional exemplary flowcell designs are shown in FIGS. 4C and 4D (e.g., a flowcell with "wide" channels, such as channels 440 in FIG. 4C, having two channels with 8 inlet and outlet ports (ports 445—8 inlet and 8 outlet) to maintain flow uniformity and a center wall, such as wall 450, for added structural support; or a flowcell with offset channels, such as the 16 offset channels (channels 480), etc.). The flowcells can be designed to maximize the collection of fluorescence from the illuminated surface and obtain diffraction limited imaging. For example, in the design shown in FIG. 4C, in particular embodiments, the light comes into the channel through 1000 μm thick bottom layer 460, which can be made of borosilicate glass, fused silica or other material as described herein, and the emitted light travels through 100 μm depth of aqueous solution within the channel and 300 μm depth of "top" layer material 470. However, in some embodiments, the thickness of the "top" layer may be less than 300 μm to prevent spherical aberrations and to image a diffraction limited spot. For example the thickness of the top layer can be around 170 μm for use with a standard diffraction limited optical system. To use the thicker top layer without suffering from spherical aberrations, the objective can optionally be custom designed, e.g., as described herein.

In the various embodiments herein, the flowcells can be created from/with a number of possible materials. For example, in some embodiments, the flowcells can comprise photosensitive glass(es) such as Foturan® (Mikroglas, Mainz, Germany) or Fotoform® (Hoya, Tokyo, Japan) that can be formed and manipulated as necessary. Other possible materials can include plastics such as cyclic olefin copolymers (e.g., Topas® (Ticona, Florence, Ky.) or Zeonor® (Zeon Chemicals. Louisville, Ky.) which have excellent optical properties and can withstand elevated temperatures if need be (e.g., up to 100° C.). As will be apparent from FIG. 4, the flowcells can comprise a number of different materials within the same cell. Thus, in some embodiments, the base layer, the walls of the channels, and the top/cover layer can optionally be of different materials.

While the example in FIG. 4B shows a flowcell comprised of 3 layers, other embodiments can comprise 2 layers, e.g., a base layer having channels etched/ablated/formed within it and a top cover layer, etc. Additionally, other embodiments can comprise flowcells having only one layer which comprises the flow channel etched/ablated/otherwise formed within it.

In some embodiments, the flowcells comprise Foturan®. Foturan is a photosensitive glass which can be structured for a variety of purposes. It combines various desired glass properties (e.g., transparency, hardness, chemical and thermal resistance, etc.) and the ability to achieve very fine structures with tight tolerances and high aspect ratios (hole depth/hole width). With Foturan® the smallest structures possible are usually, e.g., 25 μm with a roughness of 1 μm.

Figure 5A:
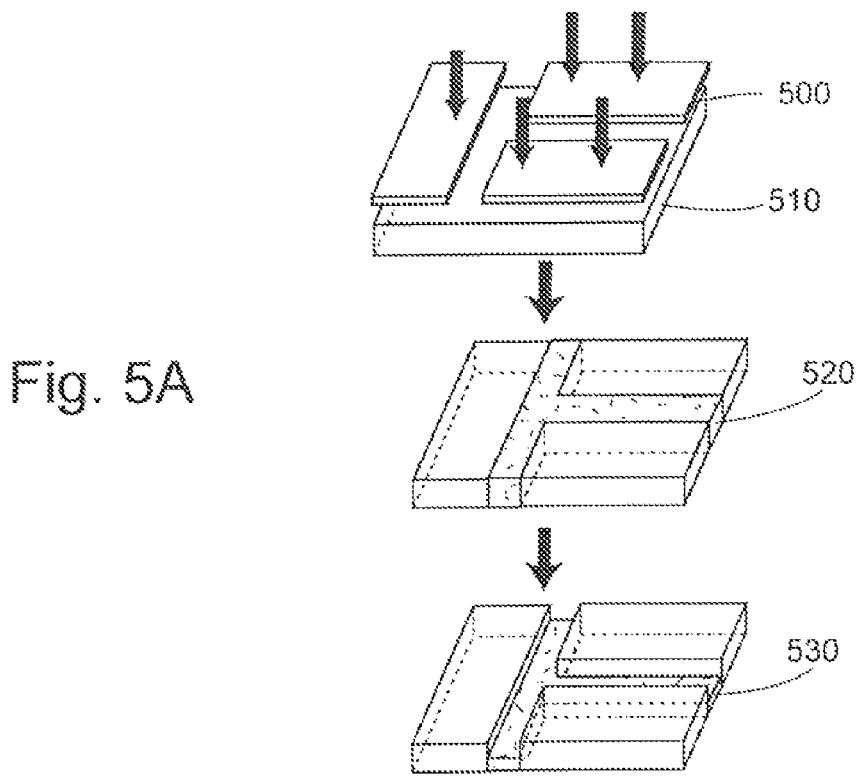
FIG. 5, Panels A and B, show one method of forming a flowcell of the system (Panel A) and a transmission spectra of Foturan glass (Panel B).
Figure 5B:
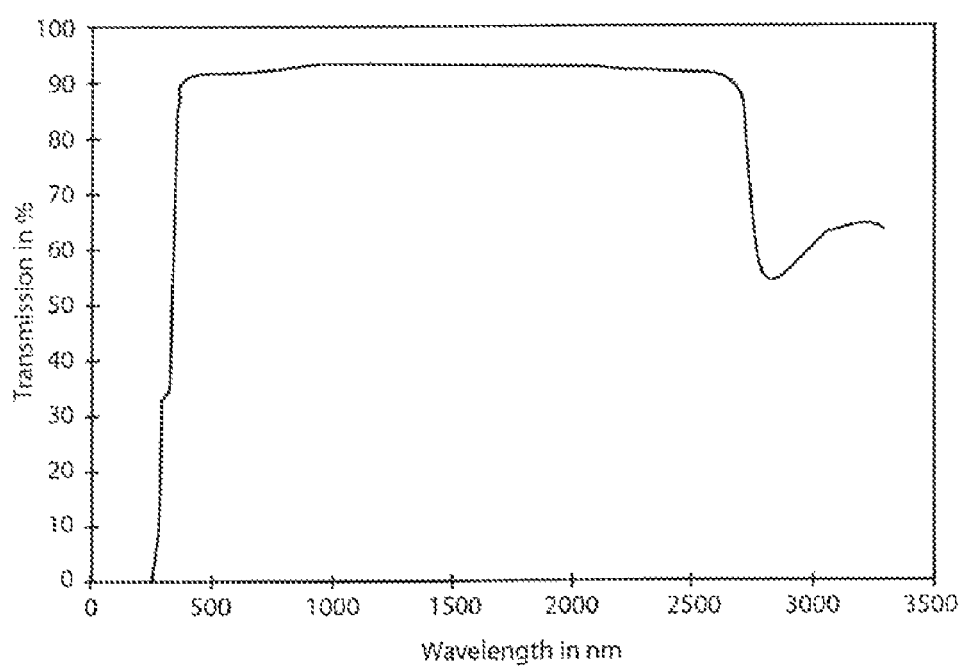
Figure 6A:
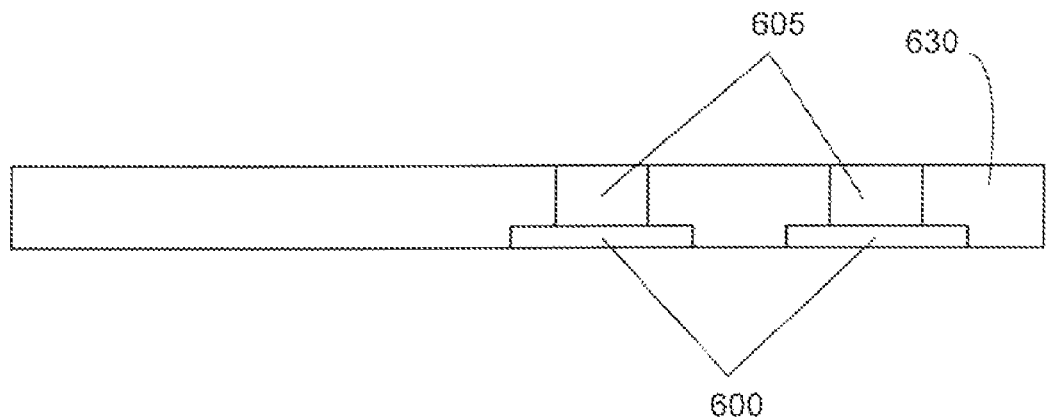
FIG. 6, Panels A-E show an exemplary possible etching method to construct flowcells herein.
Figure 6B:
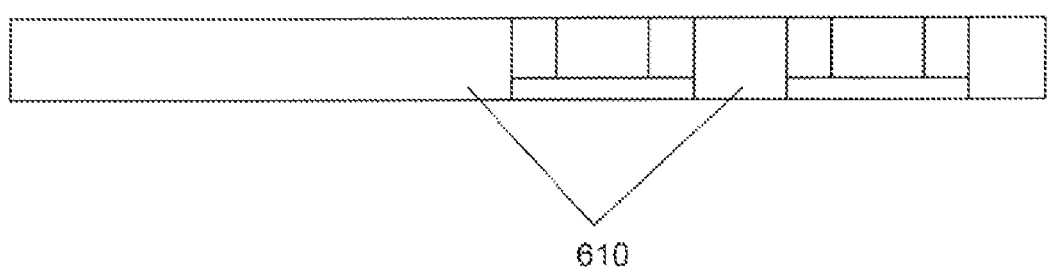
Figure 6C:
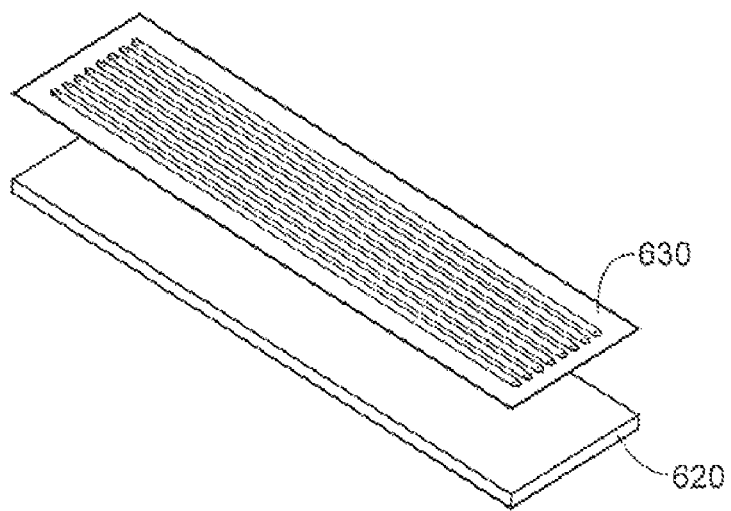
Figure 6D:
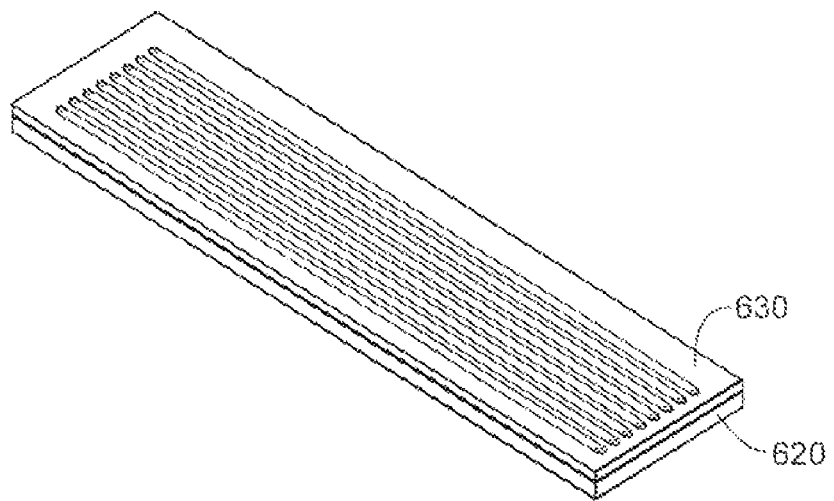
Figure 6E:
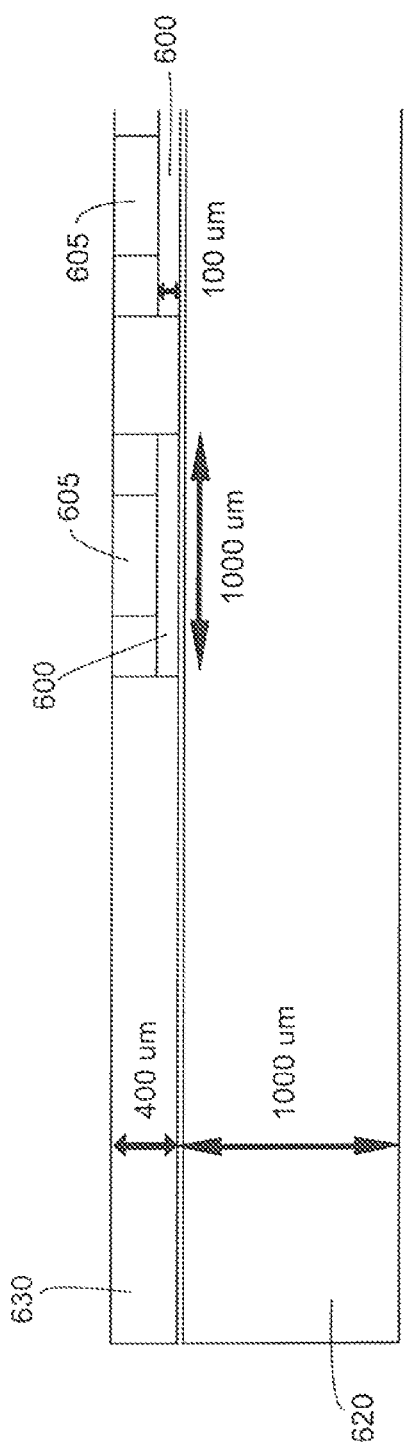

FIG. 5A, gives a schematic diagram of one possible way of patterning a flowcell (e.g., one comprising Foturan®). First the desired pattern is masked out with masks 500, onto the surface of substrate 510 which is then exposed to UV light. In such exposure step, the glass is exposed to UV light at a wavelength between 290 and 330 nm. It can be possible to illuminate material thicknesses of up to 2 mm. An energy density of approximately 20 J/cm$^2$ is typically sufficient to structurize a 1 mm thick Foturan® plate. During the UV exposure step, silver or other doped atoms are coalesced in the illuminated areas (areas 520). Next, during a heat treatment between 500° C. and 600° C., the glass crystallizes around the silver atoms in area 520. Finally, the crystalline regions, when etched with a 10% hydrofluoric acid solution at room temperature (anisotropic etching), have an etching rate up to 20 times higher than that of the vitreous regions, thus resulting in channels 530. If wet chemical etching is supported by ultrasonic etching or by spray-etching, the resulting structures display a large aspect ratio. FIG. 5B shows a transmission spectra from a sample of Foturan glass (d=1 mm).

FIG. 6, panels A through E show an exemplary etching process to construct a sample flowcell as used herein. In FIG. 6A, channels 600 (seen in an end view) and through-holes 605 (seen in an end view) are exposed/etched into layer 630. Layer 630 is the "top" layer of a two layer flowcell as can be seen in FIG. 6E (mated with bottom layer 620). The through-holes (where reagents/fluids enter into the flowcell channels) and channels can be etched into layer 630 through a 3-D process such as those available from Invenios (Santa Barbara, Calif.). Top layer 630 can comprise Foturan which, as described, can be UV etched. Foturan, when exposed to UV, changes color and becomes optically opaque (or pseudo-opaque). Thus in FIG. 6B, layer 630 has been masked and light exposed to produce darkened areas 610 within the layer (similar to the masking in FIG. 5A, but without the further etching). Such optically opaque areas can be helpful in blocking misdirected light, light scatter, or other nondesirable reflections that could otherwise negatively affect the quality of sequence reading herein. In other embodiments, a thin (e.g., 100-500 nm) layer of metal such as chrome or nickel is optionally deposited between the layers of the flowcell (e.g., between the top and bottom layers in FIG. 6E) to help block unwanted light scattering. FIGS. 6C and 6D display the mating of bottom layer 620 with channel layer 630 and FIG. 6E shows a cut away view of the same.

In various embodiments, the layers of the flowcells are attached to one another in any of a number of different ways. For example, the layers can be attached via adhesives, bonding (e.g., heat, chemical, etc.), and/or mechanical methods. Those of skill in the art will be familiar with numerous methods and techniques to attach various glass/plastic/silicon layers to one another.

Again, while particular flowcell designs and constructions are described herein, such descriptions should not necessarily be taken as limiting; other flowcells of the invention can comprise different materials and designs than those presented herein and/or can be created through different etching/ablation techniques or other creation methods than those disclosed herein. Thus, particular flowcell compositions or construction methods should not necessarily be taken as limiting on all embodiments.

Fluid Flow

Figure 7A:
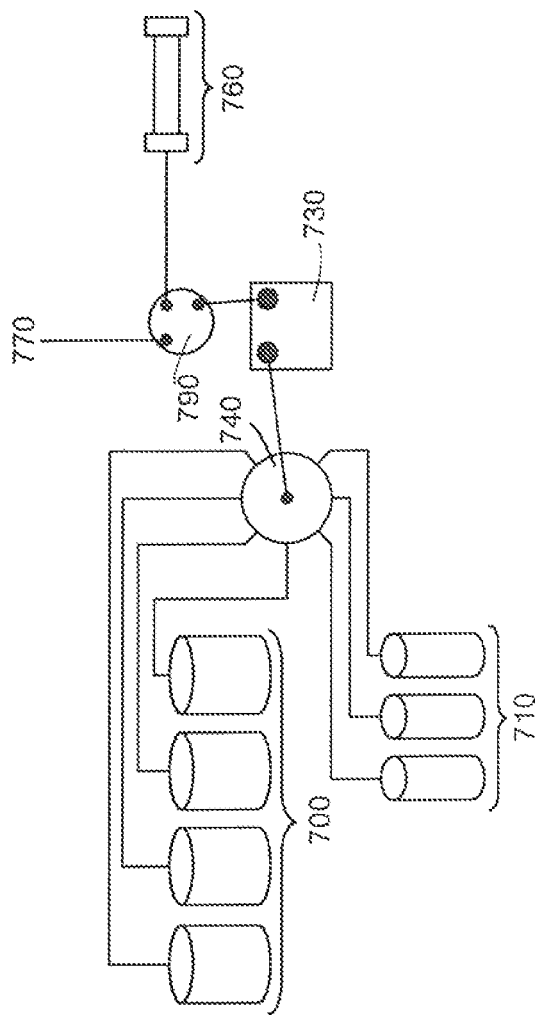
FIG. 7, Panels A-C present exemplary schematic diagrams of possible fluid flow components/arrangements of the system in push (Panel A) or pull (Panels B and C) configurations.
Figure 7B:
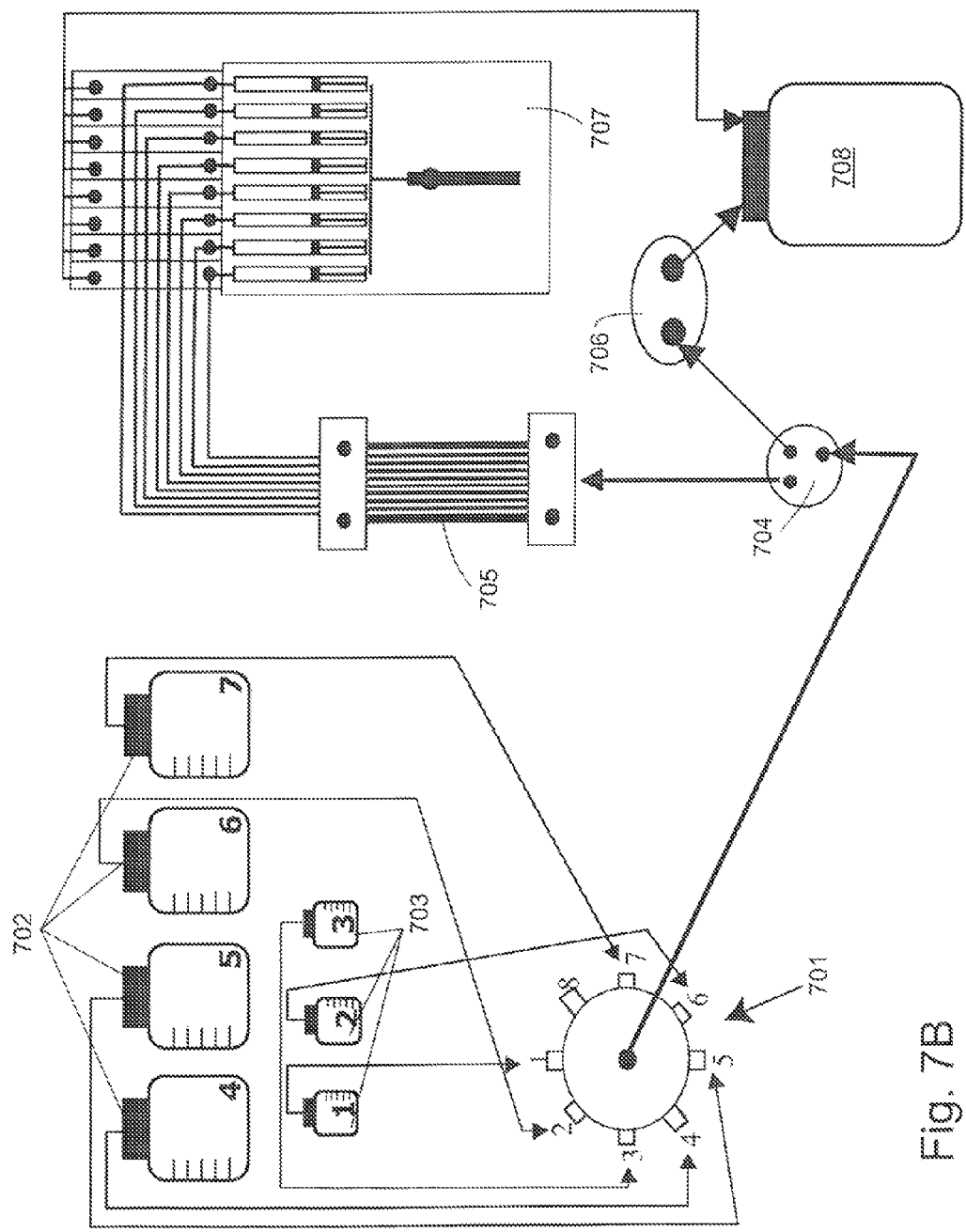
Figure 7C:
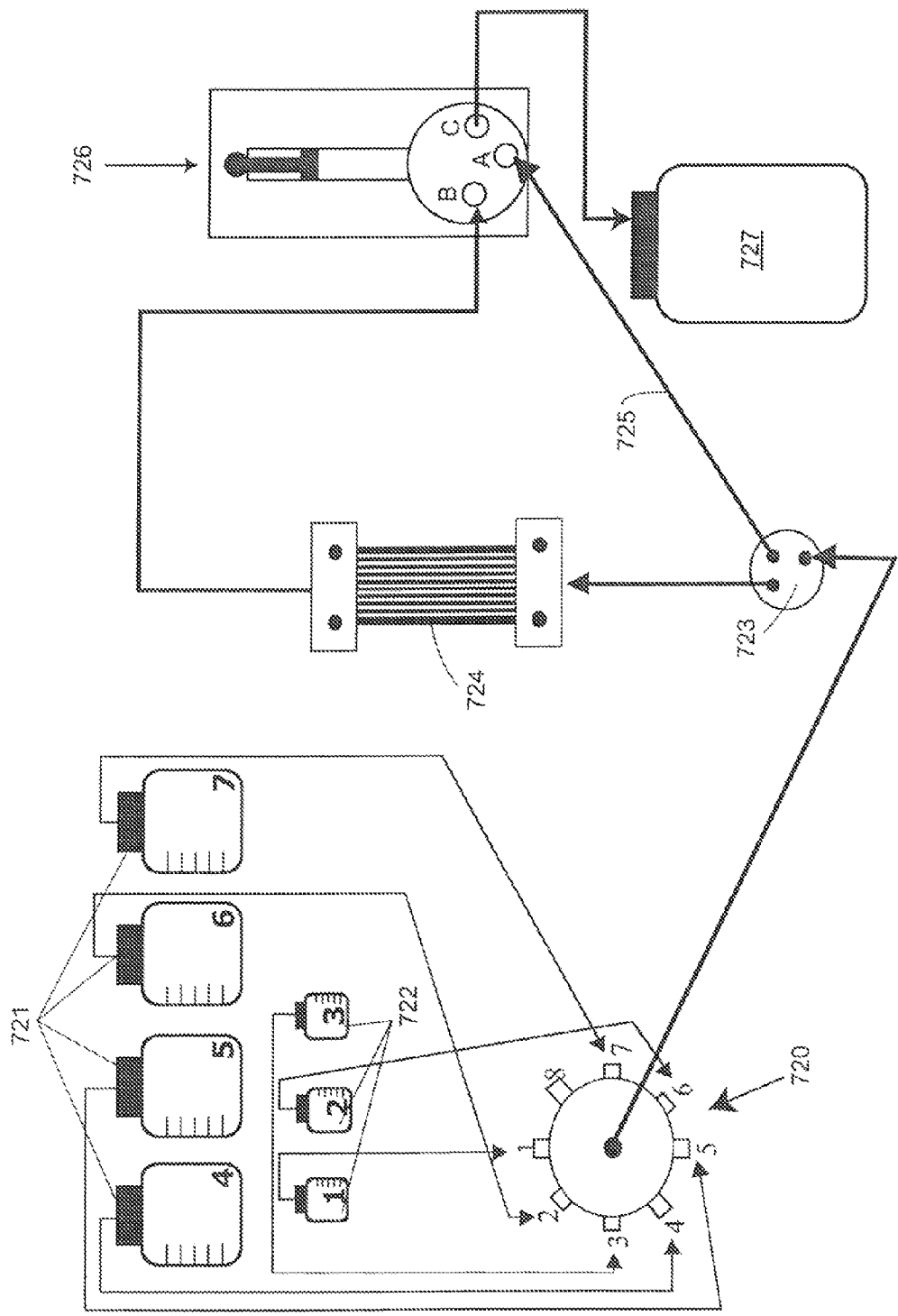

In the various embodiments herein, the reagents, buffers, etc. used in the sequencing of the nucleic acids are regulated and dispensed via a fluid flow subsystem or aspect. FIGS. 7A-C present generalized diagrams of exemplary fluid flow arrangements of the invention, set up in one way push, eight way pull, and one way pull configurations respectively. In general, the fluid flow subsystem transports the appropriate reagents (e.g., enzymes, buffers, dyes, nucleotides, etc.) at the appropriate rate and optionally at the appropriate temperature, from reagent storage areas (e.g., bottles, or other storage containers) through the flowcell and optionally to a waste receiving area.

The fluid flow aspect is optionally computer controlled and can optionally control the temperature of the various reagent components. For example, certain components are optionally held at cooled temperatures such as 4° C.+/−1° C. (e.g., for enzyme containing solutions), while other reagents are optionally held at elevated temperatures (e.g., buffers to be flowed through the flowcell when a particular enzymatic reaction is occurring at the elevated temperature).

In some embodiments, various solutions are optionally mixed prior to flow through the flowcell (e.g., a concentrated buffer mixed with a diluent, appropriate nucleotides, etc.). Such mixing and regulation is also optionally controlled by the fluid flow aspect of the invention. It is advantageous if the distance between the mixed fluids and the flowcell is minimized in many embodiments. Therefore the pump can be placed after the flowcell and used to pull the reagents into the flowcell (FIGS. 7B and 7C) as opposed to having the pump push the reagents into the flowcell (as in FIG. 7A). Such pull configurations mean that any materials trapped in dead volumes within the pump do not contaminate the flowcell. The pump can be a syringe type pump, and can be configured to have one syringe per flow channel to ensure even flow through each channel of the flowcell. The pump can be an 8 way pump, if it is desired to use an 8 way flowcell, such as for example a Kloehn 8 way syringe pump (Kloehn, Las Vegas, Nev.). A fluidics diagram of an 8 way pull configuration is shown in FIG. 7B. In FIG. 7A, fluidic reagents are stored in reagent containers 700 (e.g., buffers at room temperature, 5× SSC buffer, enzymology buffer, water, cleavage buffer, etc.) and 710 (e.g., cooled containers for enzymes, enzyme mixes, water, scanning mix, etc.). Pump 730 moves the fluids from the reagent containers through reagent valve 740, priming/waste valve 770 and into/through flowcell 760.

In FIG. 7B, fluidic reagents are stored in reagent containers 702 (e.g., buffers at room temperature similar to those listed above) and 703 (e.g., cooled containers for enzymes, etc. similar to those listed above), linked through reagent valve 701. Those of skill in the art will be familiar with multi-way valves (such as the reagent valves) used to allow controllable access of/to multiple lines/containers. The reagent valve is linked into flowcell 705 via an optional priming valve (or waste valve) 704, connected to optional priming pump 706. The priming pump can optionally draw reagents from the containers up through the tubing so that the reagents are "ready to go" into the flowcell. Thus, dead air, reagents at the wrong temperature (e.g., because of sitting in tubing), etc. will be avoided. When the priming pump is drawing, the outflow is shunted into the waste area. During non-priming use, the reagents can be pulled through the flowcell using 8 channel pump 707, which is connect to waste reservoir 708.

In either embodiment (push or pull), the fluidic configurations can comprise "sipper" tubes or the like that extend into the various reagent containers in order to extract the reagents from the containers. FIG. 7C shows a single channel pump rather than an 8 channel pump. Single channel pump 726 can also act as the optional priming pump, and thus optional priming pump or waste valve 723 can be connected directly to pump 726 through bypass 725. The arrangement of components is similar in this embodiment as to that of FIG. 7B. Thus it comprises reagent containers 721 and 722, multi-way selector valve 720, flowcell 724, etc.

The fluid flow itself is optionally driven by any of a number of pump types, (e.g., positive/negative displacement, vacuum, peristaltic, etc.) such as an Encynova® 2-1 Pump (Encynova, Greeley, Colo.) or a Kloehn® V3 Syringe Pump (Kloehn, Las Vegas, Nev.). Again, it will be appreciated that specific recitation of particular pumps, etc. herein should not be taken as necessarily limiting and that various embodiments can comprise different pumps and/or pump types than those listed herein. In certain embodiments, the fluid delivery rate is from about 50 µL to about 500 µL/min (e.g., controlled ±2 µL) for the 8 channels. In the 8 way pull configuration, the flow can be between 10-100 µl/min/channel, depending on the process. In some embodiments, the maximum volume of nucleotide reagents required for sequencing a polynucleotide of 25 bases is about 12 mL.

Which ever pump/pump type is used herein, the reagents are optionally transported from their storage areas to the flowcell through tubing. Such tubing, such as PTFE, can be chosen in order to, e.g., minimize interaction with the reagents. The diameter of the tubing can vary between embodiments (and/or optionally between different reagent storage areas), but can be chosen based on, e.g., the desire to decrease "dead volume" or the amount of fluid left in the lines. Furthermore, the size of the tubing can optionally vary from one area of a flow path to another. For example, the tube size from a reagent storage area can be of a different diameter than the size of the tube from the pump to the flowcell, etc.

The fluid flow subsystem of the invention also can control the flow rate of the reagents involved. The flow rate is optionally adjustable for each flow path (e.g., some flow paths can proceed at higher flow rates than others; flow rates can optionally be reversed; different channels can receive different reagent flows or different timings of reagent flows, etc.). The flow rate can be set in conjunction with the tube diameter for each flow path in order to have the proper volume of reagent, etc in the flowcell at a given time. For example, in some embodiments, the tubing through which the reagents flow is 0.3 mm 1D, 0.5 mm, or 1.0 mm while the flow rate is 480 µL/min or 120 µL/min. In some embodiments, the speed of flow is optionally balanced to optimize the reactions of interest. High flow can cause efficient clearing of the lines and minimize the time spent in changing the reagents in a given flowcell volume, but can also cause a higher level of shear flow at the substrate surface and can cause a greater problem with leaks or bubbles. A typical flow rate for the introduction of reagents can be 15 µl/min/channel in some embodiments.

The system can be further equipped with pressure sensors that automatically detect and report features of the fluidic performance of the system, such as leaks, blockages and flow volumes. Such pressure or flow sensors can be useful in instrument maintenance and troubleshooting. The fluidic system can be controlled by the one or more computer component, e.g., as described below. It will be appreciated that the fluid flow configurations in the various embodiments of the invention can vary, e.g., in terms of number of reagent containers, tubing length/diameter/composition, types of selector valves and pumps, etc.

Heating/Cooling

Figure 8:
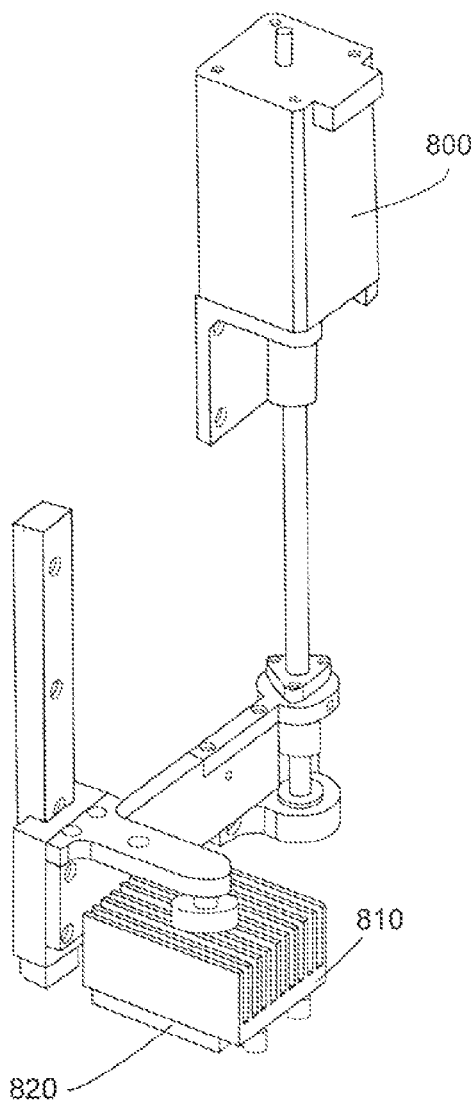
FIG. 8, shows an exemplary heating/cooling component of the system in isolation from other aspects of the invention.

In some embodiments, the systems herein comprise a heating/cooling control component having heating/cooling capabilities, e.g., through Peltier devices, etc. Optionally, the various components herein (e.g., the flowcell and its contents) can be heated by a resistive heating element and cooled through convection to create reaction conditions above ambient temperature. Such heating/cooling component(s) can control the temperature of the flowcells (and the fluids within them) during the various reactions required in sequencing-by-synthesis. An exemplary flowcell temperature control system is shown in FIG. 8 (in isolation from the other components of the system). In FIG. 8, Peltier fan 800 is shown in relationship to heat sink 810 and Peltier heater 820. The flowcell heating/cooling component is optionally positionable and/or movable in relation to the other components of the system (e.g., the flowcell and flowcell holder, etc.). Thus, the heating/cooling component can be moved into place when needed (e.g., to raise the temperature of the reagents in the flowcell to allow for enzyme activity, etc.) and moved away when not needed. Additionally and/or alternatively, the flowcell and flowcell holder can optionally be moved in relation to the heating/cooling component. See FIG. 10A and 10B below. In various embodiments, the temperature control elements control the flowcell temperature, e.g., from about 20° C. to about 60° C. or any other temperature/temperature ranges as required by the reactions to be done within the systems/devices. The temperature of the heating element can be adjusted to control the temperature of the flowcell and the reagents therein. As the flowcell is exposed to a flow of cooled reagents, the temperature of the heating element may be higher than the temperature desired at the surface of the flowcell. For example the heating element may be set to 55° C. to obtain a flowcell temperature of 45° C.

Those of skill in the art will be familiar with Peltier devices used for temperature control (which can optionally be used in the systems herein). Again, it will be appreciated that while certain heating/cooling devices are recited herein, such should not be construed as necessarily limiting. Thus, in certain embodiments heating/cooling devices other than Peltier devices are optionally comprised within the present invention. In typical embodiments, notwithstanding the type of device, the heating/cooling component is optionally controlled (e.g., in terms of temperature, time at particular temperatures, movement of the component, and/or movement of other devices such as the flowcell holder to the heating/cooling component) by the computer component (see below).

In some embodiments, additional heating/cooling elements can optionally regulate the temperature of other components in addition to or alternate to the flowed. For example, heating/cooling components can optionally regulate the temperature of the camera, the reagent reservoirs, which can be cooled, for example to 4° C. to prolong the storage life of the reagents during long sequencing runs, the temperature of the atmosphere inside the instrument etc.

Multiple Flowcells and Alternative TIRF and Heating/Cooling Approaches

In certain embodiments herein, the systems/devices can comprise additional approaches to flowcell configuration, TIR illumination, heating/cooling configurations of the flowcell(s), and in how the flowcells are held/stabilized within the device. While such approaches can optionally be utilized together in certain embodiments, it will be appreciated that they each can be used in any combination, e.g., with each other, with any of the other approaches described herein, etc.

In some embodiments, the flowcells herein can be "bottom flow" flowcells. Thus, as opposed to the flowcells, e.g., as shown in FIGS. 4, 6, and 9 where the flowcells are clamped down and fluid flow enters from the top side of the flowcell, some flowcells can comprise configurations that allow fluid flow that enters from the bottom of the flowcell. Such bottom flowcells can be similar in construction and composition as "top flow" flowcells. In some embodiments bottom flow flowcells can comprise less fluidic dead volume (and use more of the whole channel length than top flow flowcells, e.g., since the ends of the flowcells are not covered by clamps/manifolds, etc.). See, e.g., FIG. 44-49.

Bottom flow flowcells can optionally be held to the flowcell holder through vacuum chucking rather than clamps. Thus, a vacuum can hold the flowcell into the correct position within the device so that proper illumination and imaging can take place. Cf., FIGS. 44-49 with FIG. 9. Thus, some embodiments herein also comprise one or more vacuum creation device to create a vacuum (or partial vacuum, etc.) to hold the flowcell and/or prism to the flowcell holder, XY stage, etc.

Figure 46:
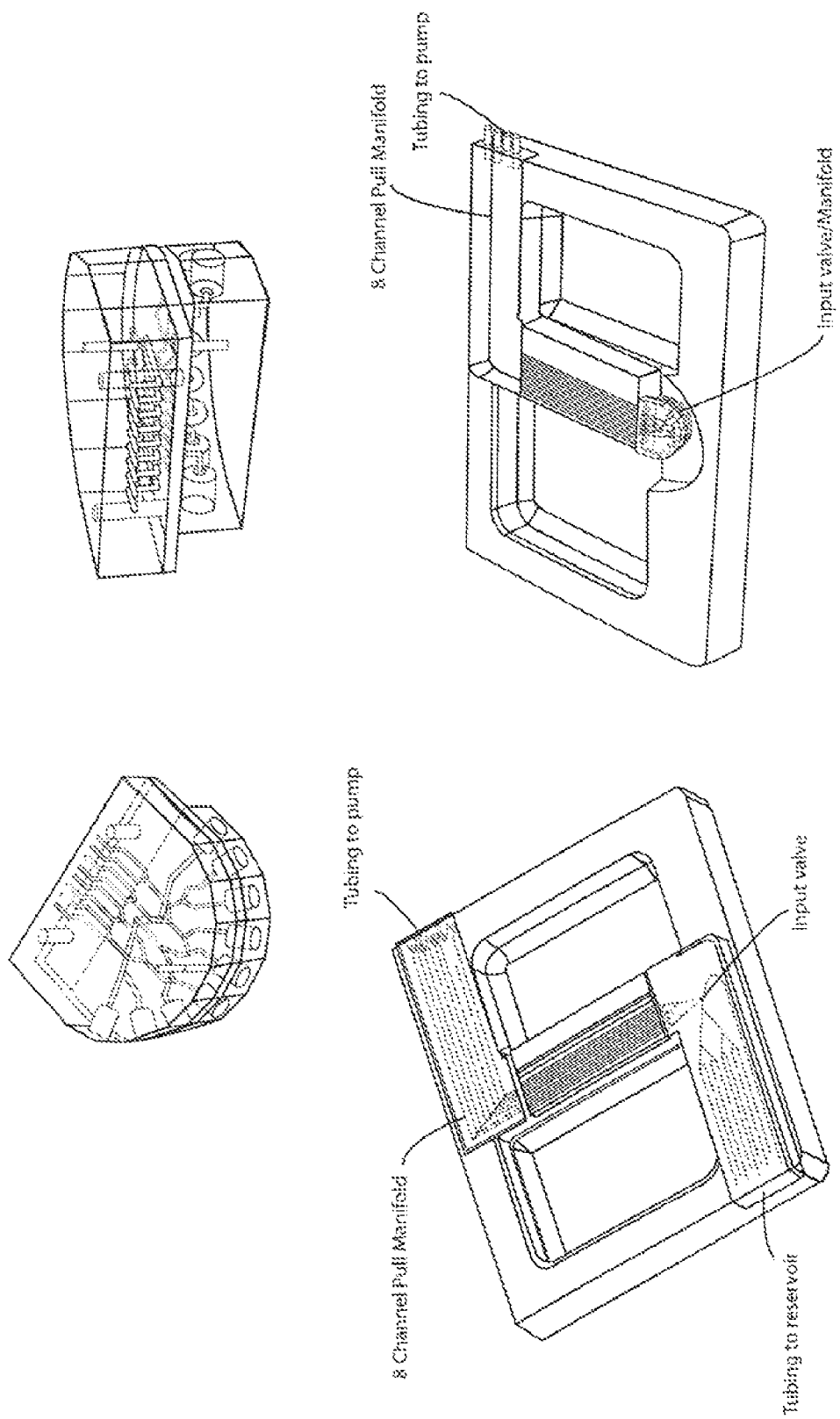
FIG. 46 shows an exemplary fluidic valve and exemplary manifolds (e.g., for use with bottom flow flowcells).
Figure 47:
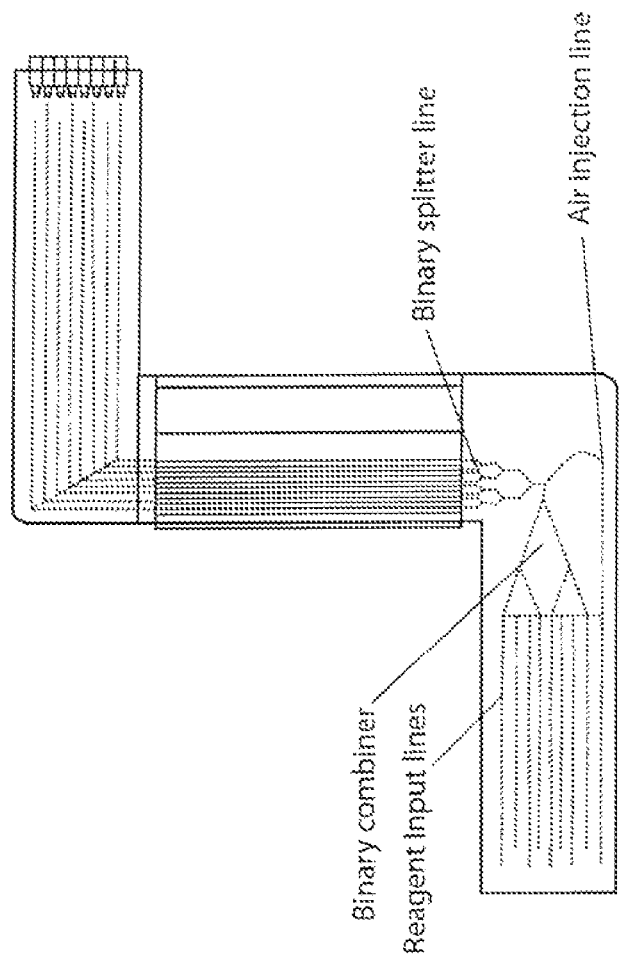
FIG. 47 shows an exemplary fluidic valve of the invention.
Figure 49E:
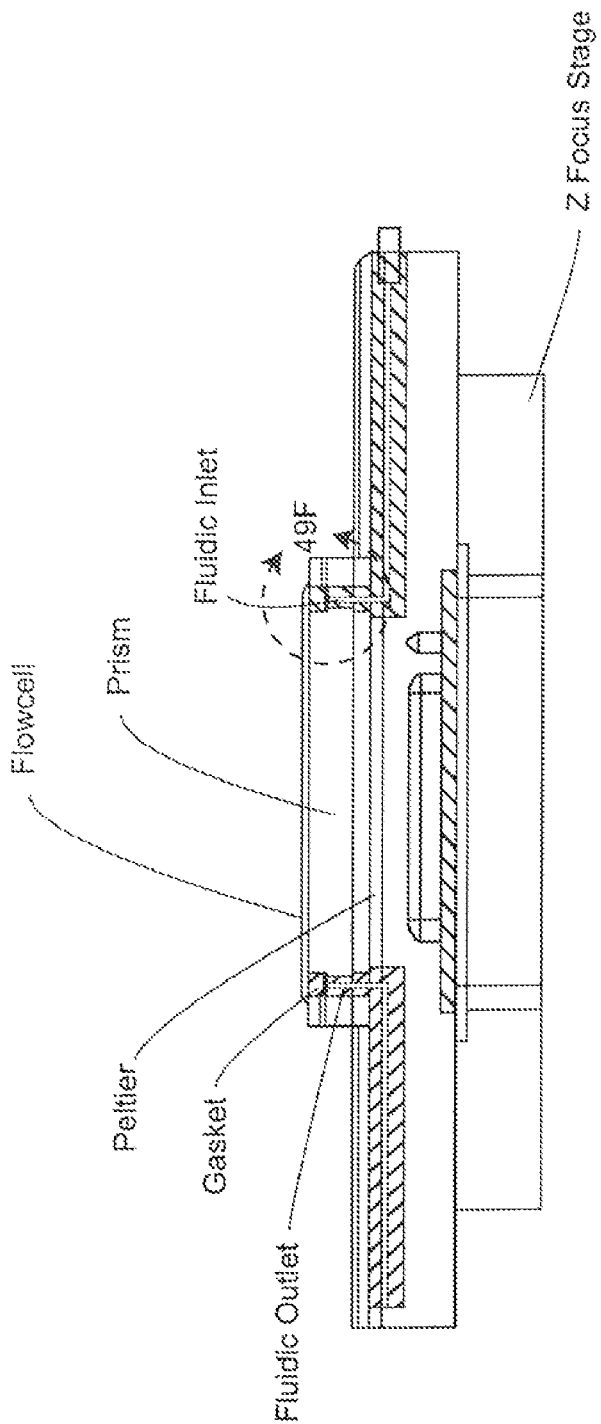
FIG. 49, Panels A-F show various exemplary bottom temperature regulation configurations capable of use with bottom flow flowcells of the invention.
Figure 49F:
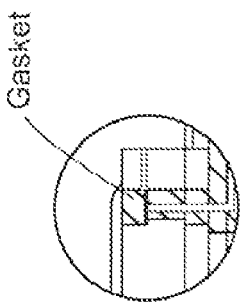

Various examples of flowcell holder manifolds are shown in FIG. 46 that can be used with bottom flow flowcells. As can be seen, the fluids flowed into/through/out of the flowcell are directed through various branching tubes within the manifolds to/from specific channels within the flowcell. Again, such embodiments can optionally not obstruct any (or not substantially any) of the top surface of the flowcell which might interfere with illumination/imaging of the Ml length of the channels. FIG. 47 displays an exemplary fluidic valve. Such valve has no moving parts or vibrations and a low dead volume. In such arrangements, each reagent bottle/container can have an open/close valve. After drawing a fluid, air can be injected before closing the reservoir valve thereby forcing an air gap valve between reagents. Cooled reagents can be returned to their reservoirs and all reagents in case of a system shut down. Also, an air injection pump can be added to the push/pull pump (e.g., a kloehn pump).

Figure 44E:
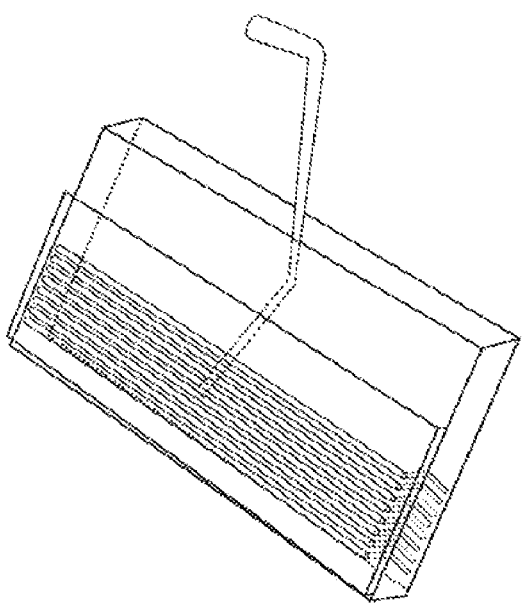
FIG. 44, Panels A-F show exemplary embodiments of bottom flow flowcells, prisms, and side/top TIRF illumination
Figure 44F:
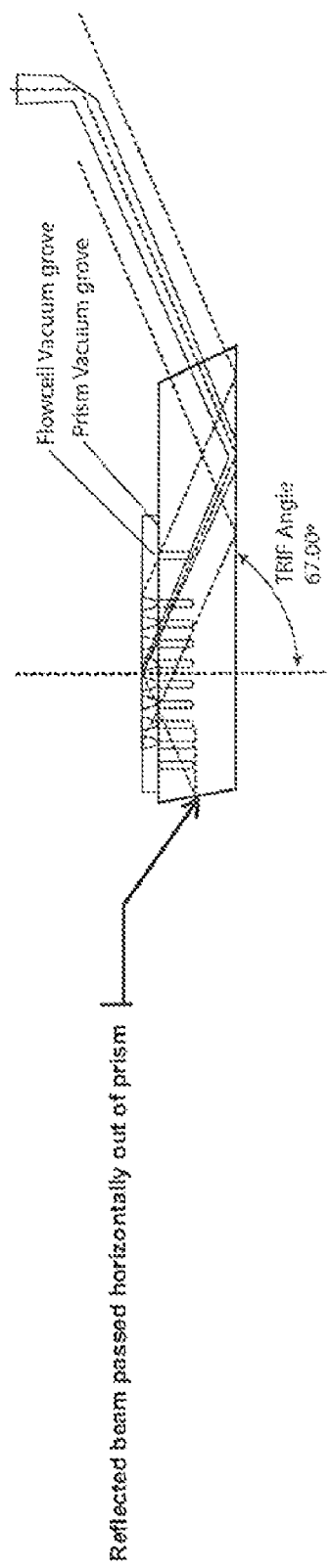

Another approach to illumination can comprise "top down" illumination. Such top down approach can be useful when used in conjunction with vacuum chucking (and bottom temperature control below). It can optionally be problematic to illuminate from the bottom (e.g., as in FIG. 1, etc.) in configurations with vacuum chucking and bottom temperature control since such embodiments often utilize the space below the flowcell. As can be seen in FIG. 44, top down or side illumination comes from above into prism 4401 upon which flowcell 4402 rests (and is optionally held down by vacuum). Such arrangement can also help prevent bowing of the flowcell which presentation can aid in auto focusing and flat field imaging and can aid in configuration with multiple flowcells having simultaneous reading, etc. Laser illumination 4400 is also shown entering into the prism in FIG. 44 as is mirror 4405 and manifold/fluidic connector 4404.

Figure 45:
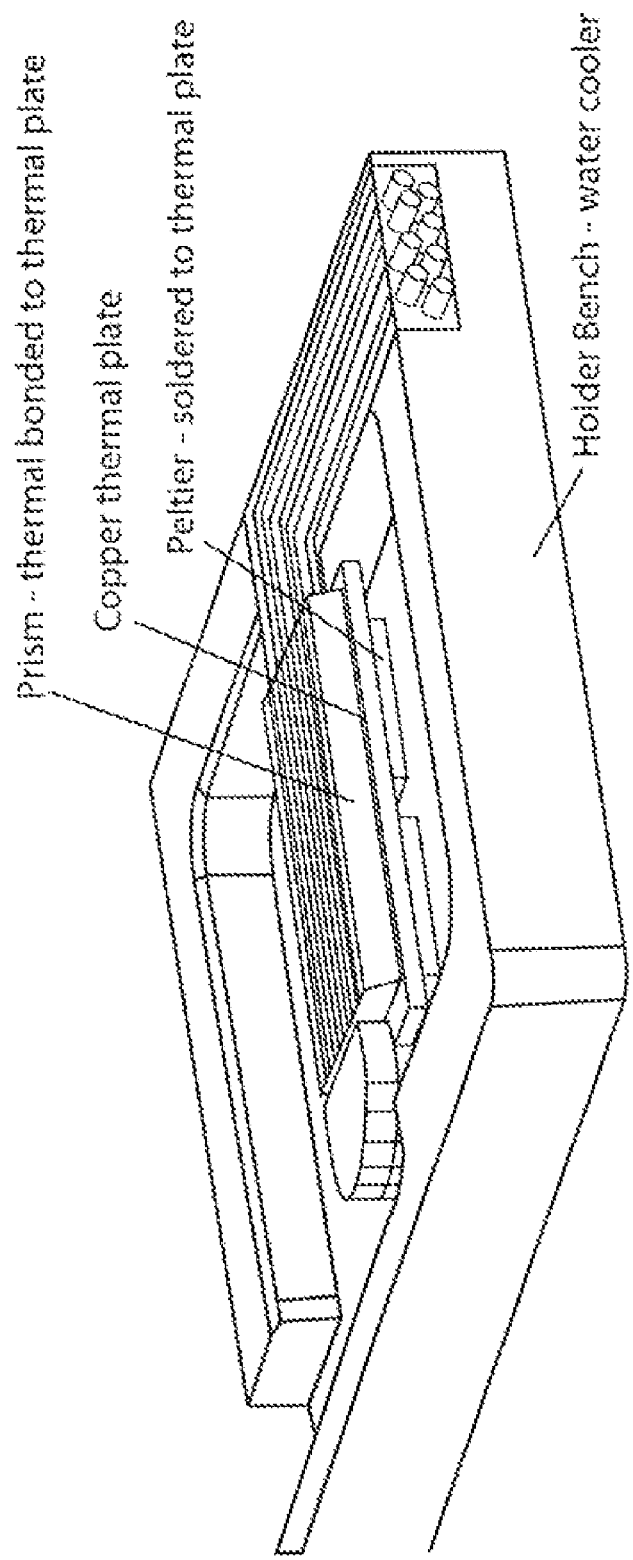
FIG. 45 shows an exemplary temperature regulation component beneath a flowcell and prism.

FIG. 45 shows another approach to thermodynamic control of a flowcell (and the reagents and reactions within it). FIG. 45 shows an exemplary embodiment of a bottom temperature controlled device. In some such embodiments, the aspect can comprise a water cooled bench that can help assure dimensional stability during read cycles and controlled scan buffer temperature. A thermal plate can extend past the prism and flowcell and under the manifolds to optionally help in uniform temperature control. Fluids can optionally be preheated when passing through the inlet manifold. Also, RTD temperature feedback can be imbedded in top of the prism to assure that the flowcell is at the desired set temperature and that thermal resistant effects of the prism are minimized.

Figure 48A:
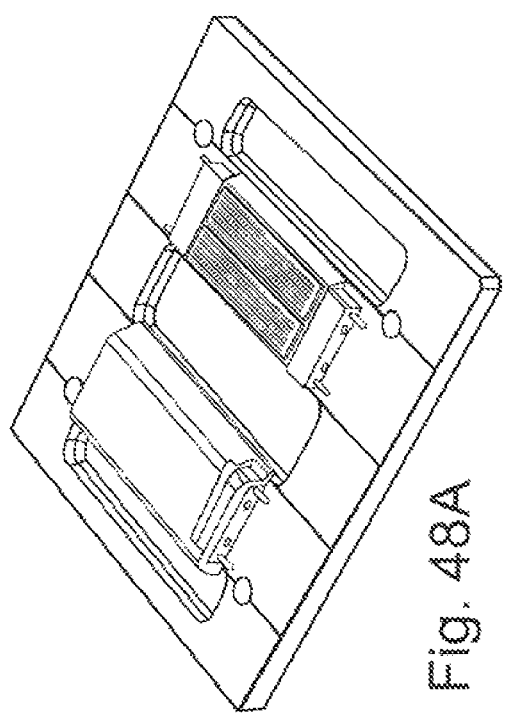
FIG. 48, Panels A and B show one possible dual flowcell configuration of the invention.
Figure 48B:
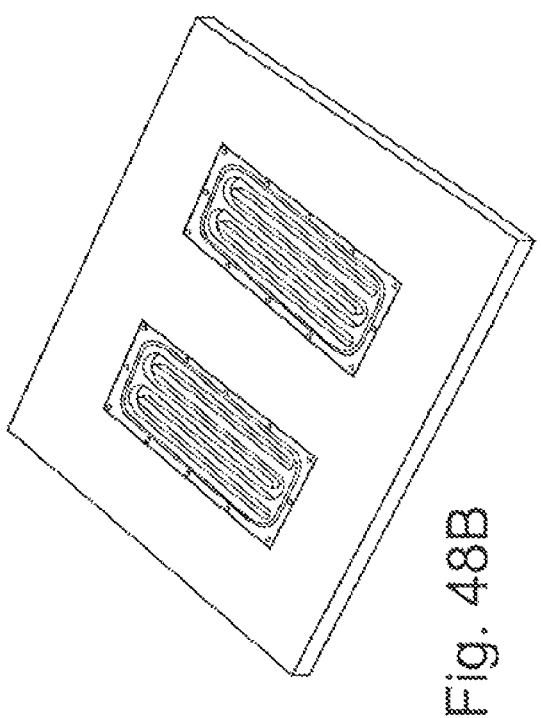

Configurations having multiple flowcells within a flowcell holder are shown in FIG. 48. As can be seen, up to four flowcells can be loaded into the holder in FIG. 48A (or two double wide flowcells, e.g., having 18-20 channels each). Peltiers or other similar devices can be beneath the flowcells and can optionally be water cooled through the holder bench aspect (which can be kept at room temperature optionally).

Stage and Flowcell Holder

Placement and movement of the flowcell (and thus the nucleic acids to be sequenced) is controlled and secured by, e.g., a movable stage upon which the flowcell and flowcell holder (or other substrate) are located. Such movable stage can optionally allow movement of the flowcell in relation to the laser illumination and lens objective to read the sequencing reactions within the channels. If desired, the scanning stage or other components can be actively cooled during the scanning cycle to control the temperature of the substrate during the imaging cycles.

Figure 9A:
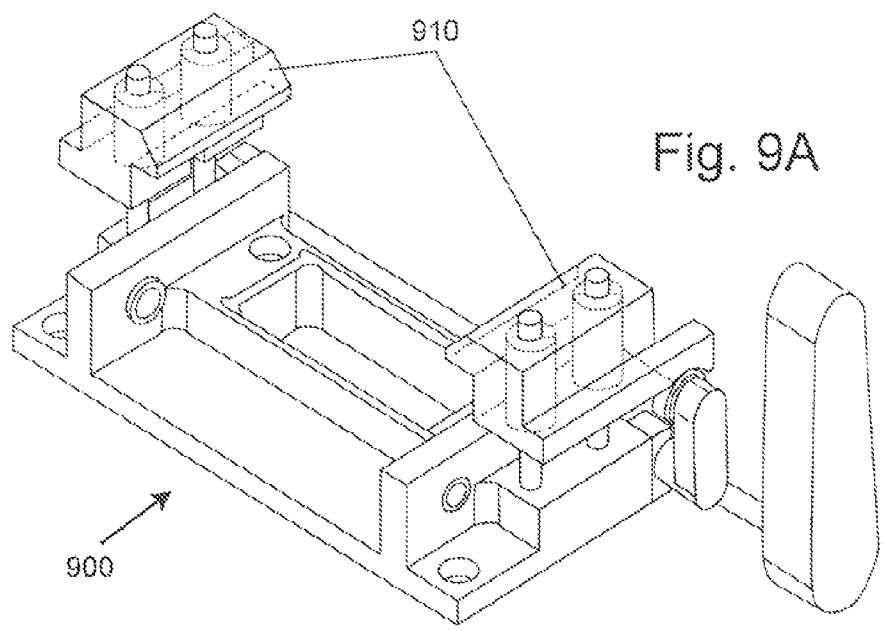
FIG. 9, panels A-D present schematic diagrams of possible flowed and flowcell holder configurations of the invention.
Figure 9B:
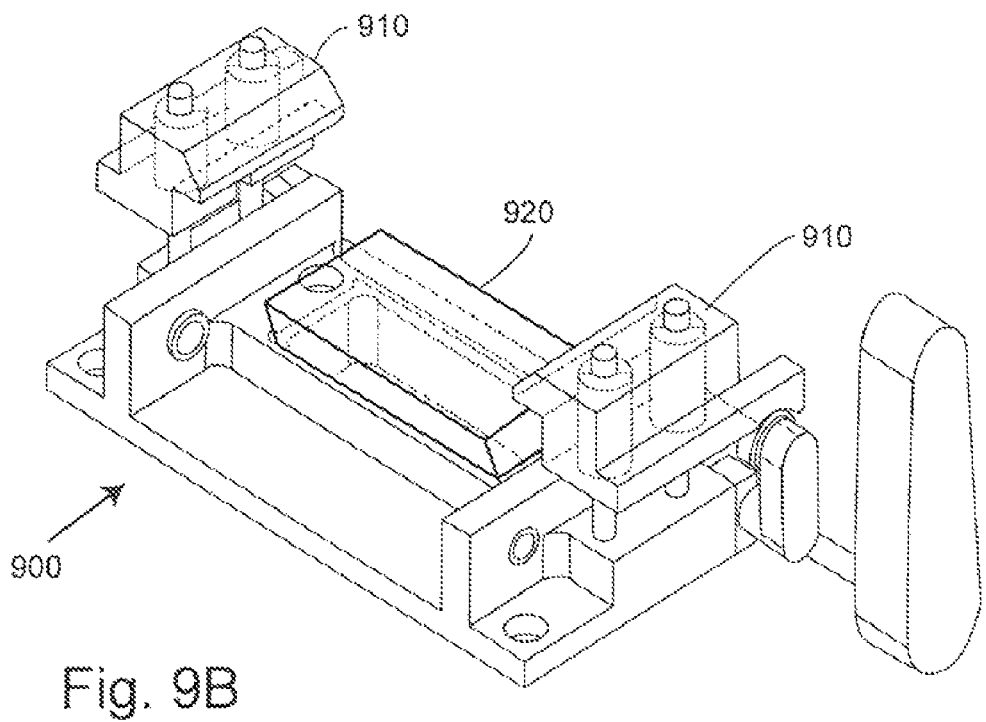
Figure 9C:
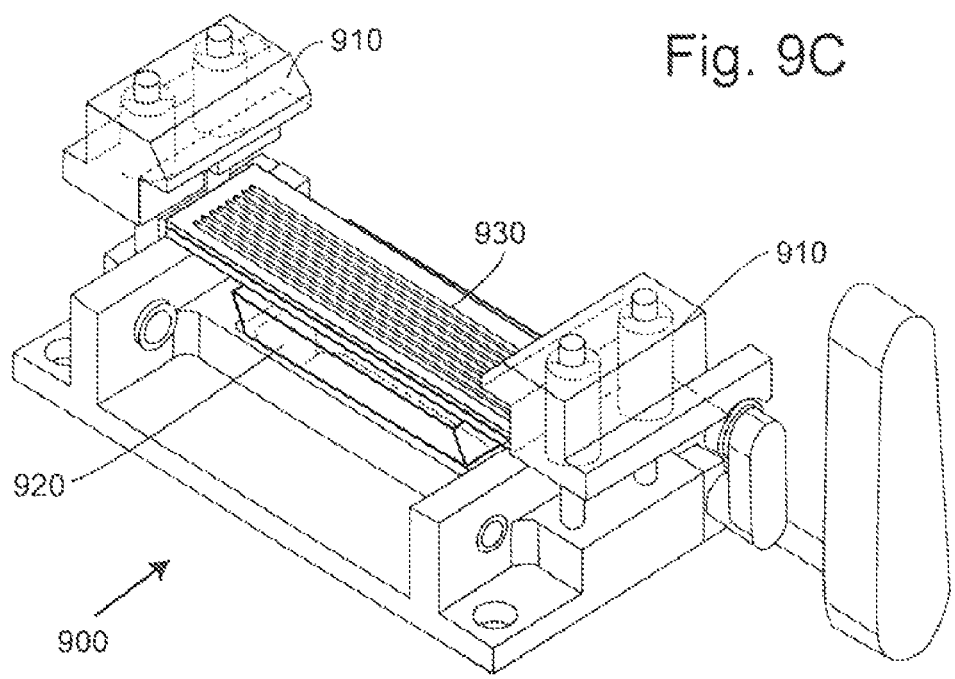

FIG. 9, panels A through D, displays schematic diagrams of an exemplary flowcell holder of the current system. FIG. 9A shows flowcell holder 900 before a flowcell is placed upon it. As can be seen, the holder comprises adjustable clamps 910 (optionally spring loaded) to securely fasten the flowcell to the holder and optionally one or more manifolds (e.g., optionally comprised within the clamps) to fluidically connect the flowcell channels to the rest of the fluidic system. A manifold can individually connect each of the channels in parallel. Alternatively, a manifold can connect the channels such that they are connected via a single inlet line that is split to flow in parallel to each channel, or can be configured as a "serpentine" configuration to make a single fluid flow. Such a manifold can be configured to contain a single 1-8 split, or can comprise a binary splitter wherein each fluid channel is only split into 2, to obtain a split from 1-2-4-8, in order to give a more uniform flow along each of the 8 channels. In the 8 way pull configuration, the "exit" manifold from the flowcell can comprise 8 individual ports, each connected to a barrel of an 8 way syringe pump, whilst the "inlet" manifold can contain a single entry tube to reduce the length of tubing needed to till the flowcell. The inlet manifold can contain a 1-8 splitter or a binary 1-2-4-8 splitter for partitioning the flow evenly down each of the 8 channels. FIG. 9B also shows the presence of adjustable prism 920 that optionally can be raised/lowered to come into contact with the underside of the flowcell. The prism is used in conjunction with the lasers in the TIRF activity. In particular embodiments, oil (e.g., immersion oil such as that available from Cargille; catalog #19570 or the like) is placed between the prism and the flowcell in a uniform and continuous layer to create total internal reflection through the layer of air between the prism and the flowcell glass. FIG. 9C shows placement of flowcell 930 upon the holder and prism and FIG. 9D shows the flowcell clamped to the flowcell holder with handle/clamp 940 being lowered to help secure the clamps and flowcell.

The flowcell and flowcell holder can be situated upon a movable stage or platform. Such stage optionally is adjustable along, X, Y, and Z axes. This allows fine scale height and placement adjustment of the flowcell in relation to the lasers, camera, lens optics, etc, and allows the surface of the flowcell to be kept in focus relative to the imaging device. Furthermore, the movable stage can optionally allow the flowcell to be moved back and forth between the heating/cooling component and the optic/laser components (i.e., to allow enzymatic reactions when heated and to quantify the outcome of such reactions with the camera/laser components). FIG. 10 shows photographs depicting movement of flowcell 1020 and flowcell holder 1010 between the heating/cooling element (left picture) and the camera/laser elements (right picture). Thus the x and y components can allow the flowcell to be moved laterally (e.g., by 10s of centimeters), whilst the height can be adjusted (e.g., by 10s of nanometers) vertically to allow focusing of the images. Alternatively, the stage also can be simply an XY stage with no vertical setting, and the lens objective can be adjustable in the Z plane to ensure focus is maintained. It will be appreciated that the heating/cooling elements are optionally movable as well, e.g., in order to come into closer proximity with the flowcell, etc. Cf., FIG. 10 left picture (heating/cooling device raised) and FIG. 10 right picture (heating/cooling device lowered onto flowcell).

Figure 10B:
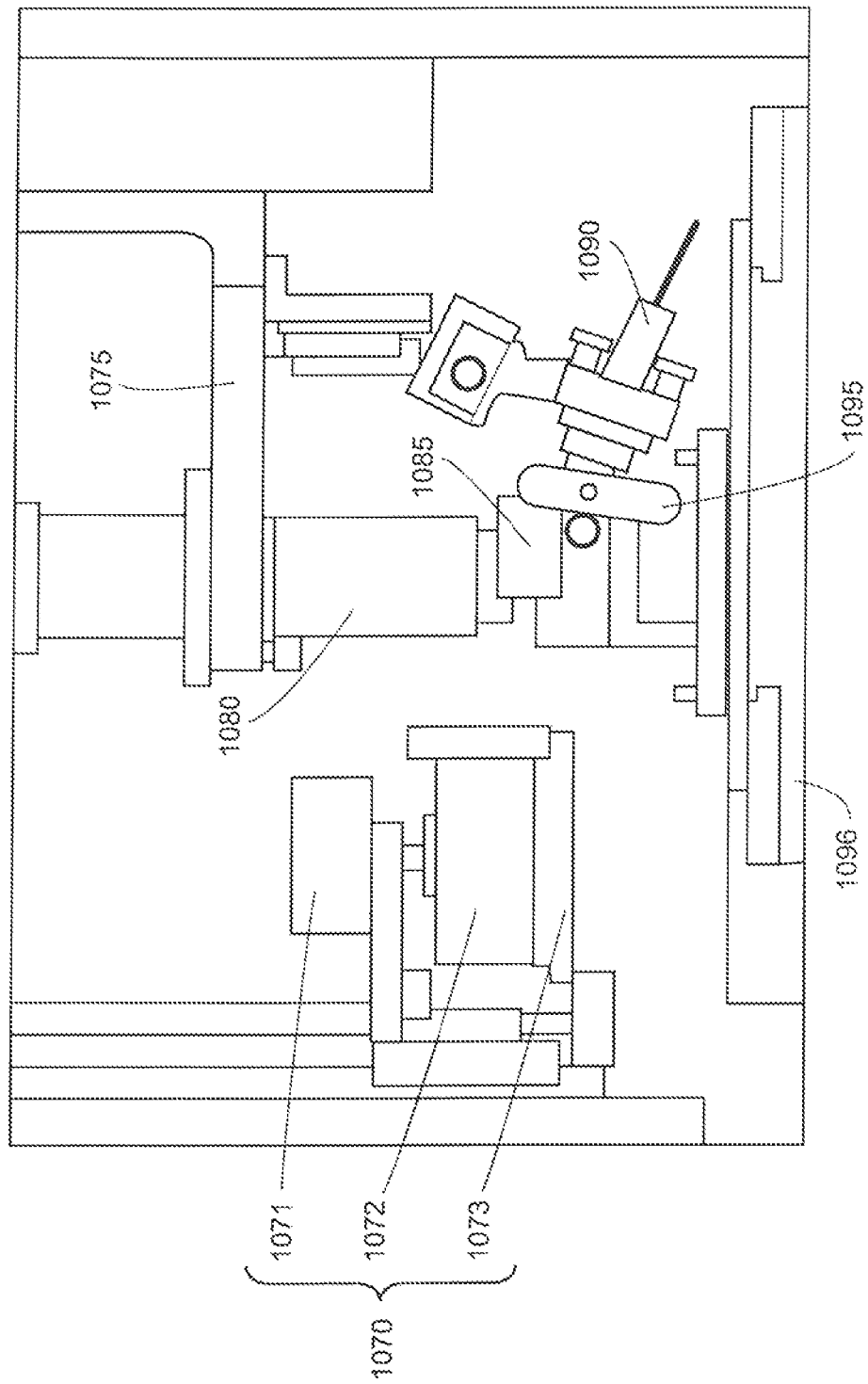
FIG. 10, Panels A and B present photographs of an exemplary embodiment of the invention showing movement of the heating/cooling component and the flowcell holder (Panel A) and a schematic of the heating/cooling components in relation to other components of an exemplary system (Panel B).

FIG. 10A shows a photograph of the instrument before and during the heating step. Peltier device 1000 (comprised of fan 1001, heat sink 1002 and heater unit 1003) moves in the vertical direction to come into contact with the flowcell 1020 and flowcell holder 1010 mounted on XY stage 1050. Reagents are introduced into the flowcell via tube 1040. The flowcell can move to a position located under camera 1030 for imaging. A schematic representation of the device in the imaging location is shown in FIG. 10B, where the Peltier device 1070 is in the raised position (with fan 1071, heatsink 1072, and heater 1073), flowcell 1085 and stage 1086 are sited next to the fiber optic mount 1090 and below lens objective 1080. The fiber optic mount is connected to the Z stage 1075, which also controls the height of lens objective 1080. The flowcell is clamped in place onto the flowcell holder by the manifold lever/handle 1095.

Figure 11A:
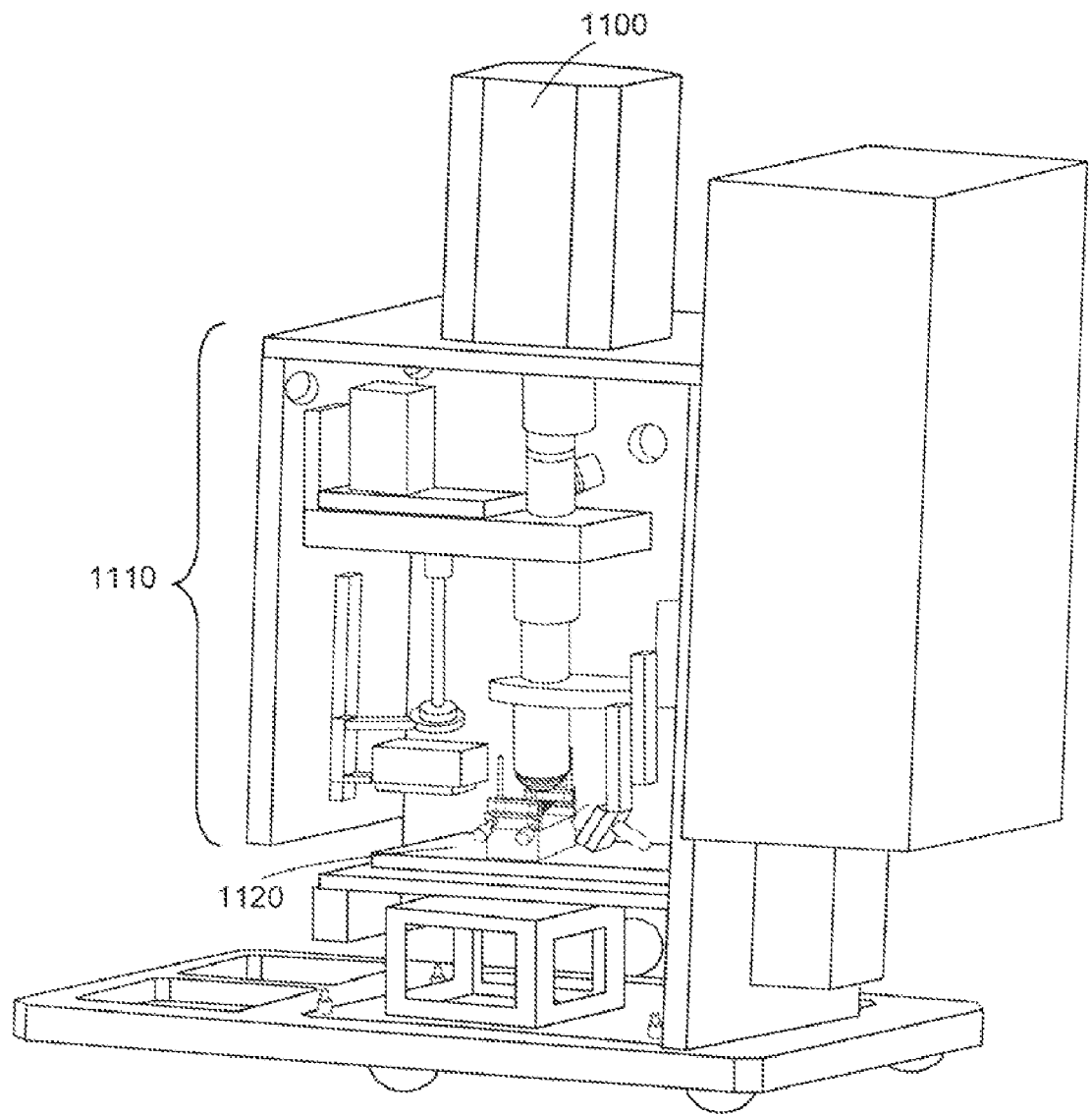
FIG. 11, Panels A and B show schematics displaying an exemplary framework holding the optics, fiber optic laser mount, heating/cooling, and flowcell holder components (A); and an exemplary flowcell leveling adjustment configuration (B).
Figure 11B:
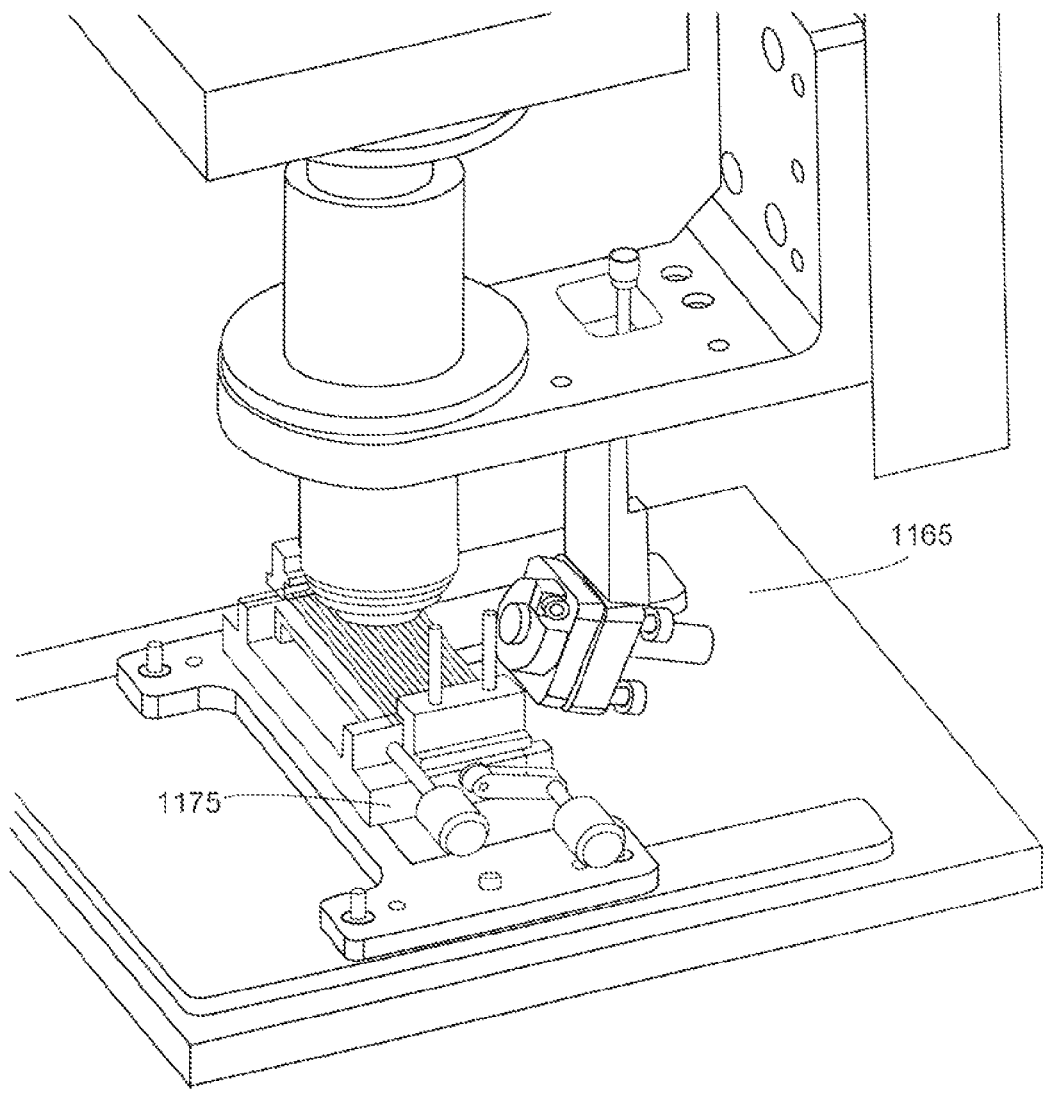
Figure 12:
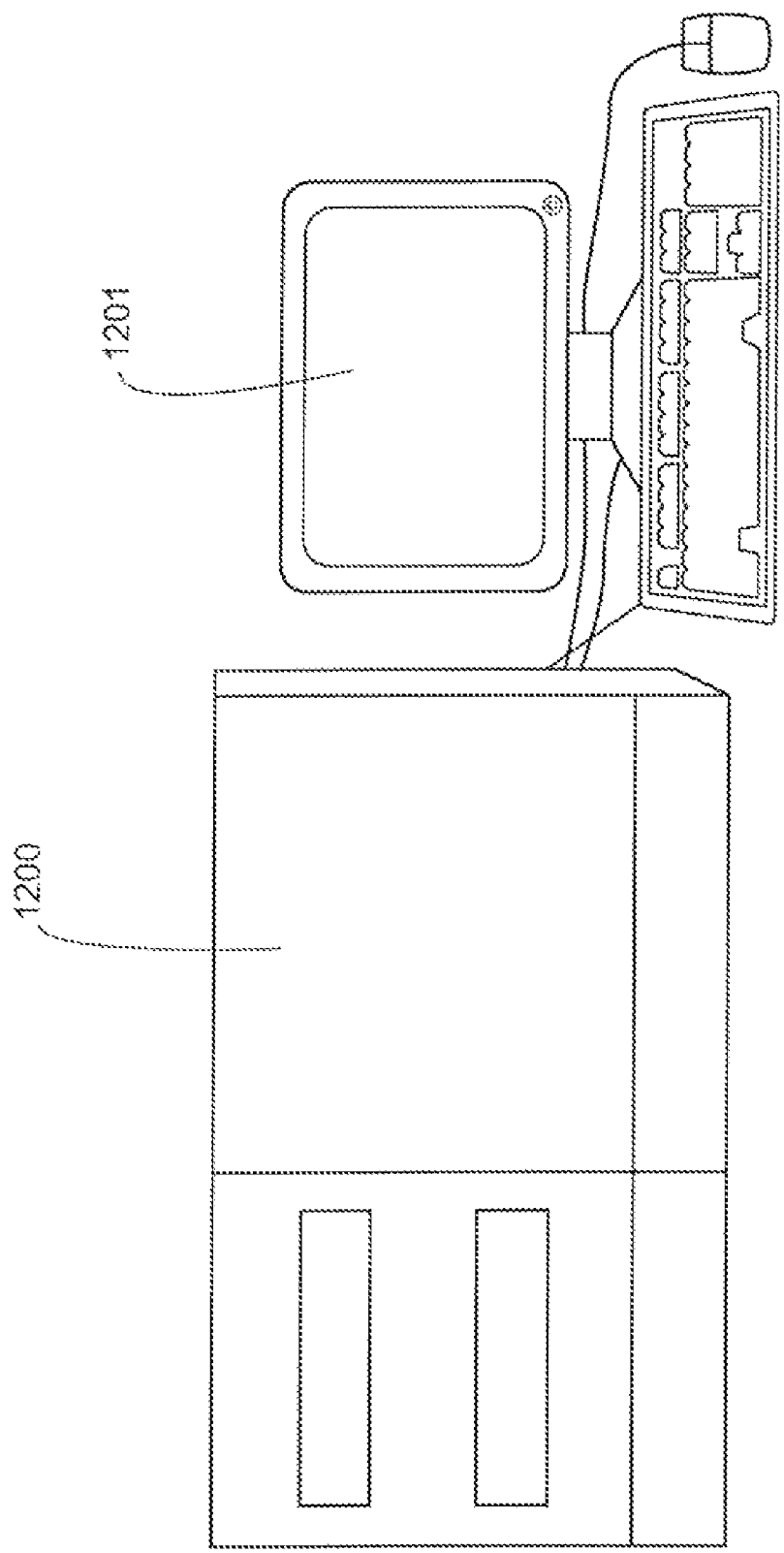
FIG. 12, presents a picture of an exemplary embodiment of the system showing framework and housing of the system.

Additionally, it will be appreciated that the various components herein, e.g., the laser components, heating/cooling components, etc., are typically arranged on a scaffolding, chassis, or framework and optionally enclosed within a housing to fully or partially enclose the instrument. The particular configuration of such framework and/or housing can optionally vary in different embodiments based upon, e.g., the particular components, their size, etc. In typical embodiments however, the framework keeps the various components secure and in the proper location and orientation while also optionally aiding in the movement of the components when necessary. The framework should be rigid enough to prevent vibrations within the instrument and the various components. For example the mode scrambler can be motion damped and vibrationally isolated from the stage to prevent shaking of the flowcell during imaging. FIG. 11A shows a schematic displaying an exemplary framework holding the camera (1100), heating/cooling components 1110, (cf., FIG. 8) flowcell and flowcell holder, and movable stage 1120. Additional aspects of framework and mounting that aid in tying together the various components and aspects of the device/system include various alignment and mounting pins/locations can be seen in FIG. 11B which shows the bearing slide for laser piece vertical adjustment 1165 and flowcell leveling adjustment component 1175. Other frameworks and housing, including external covers (skins) for the housing can be seen in FIG. 12 along with computer monitor 1201.

Excitation and Observation

In certain embodiments herein, the incorporation of specific nucleic acid bases with their accompanying specific fluorescences is tracked via laser excitation and camera observation. In various embodiments, the illumination is performed using Total Internal Reflection (TIR) comprising a laser component. It will be appreciated that a "TIRF laser," "TIRF laser system," "TIR laser," and other similar terminology herein refers to a TIRF (Total Internal Reflection Fluorescence) based detection instrument/system using excitation, e.g., lasers or other types of non-laser excitation from such light sources as LED, halogen, and xenon arc lamps (all of which are also included in the current description of TIRF, TIRF laser, TIRF laser system, etc. herein). Thus, a "TIRF laser" is a laser used with a TIRF system, while a "TIRF laser system" is a TIRF system using a laser, etc. Again, however, the TIRF systems herein (even when described in terms of having laser usage, etc.) should also be understood to include those TIRF systems/instruments comprising non-laser based excitation sources. Those of skill in the art will be well aware of different aspects of TIRF systems and their general use. In various embodiments, the camera component comprises a CCD camera. In some embodiments, the laser comprises dual individually modulated 50 mW to 500 mW solid state and/or semiconductor lasers coupled to a TIRF prism, optionally with excitation wavelengths of 532 nm and 660 nm. The coupling of the laser into the instrument can be via an optical fiber to help ensure that the footprints of the two lasers are focused on the same area of the substrate (i.e., overlap).

Mode Scrambling

In the various embodiments herein, the area wherein the laser(s) or other excitation source(s) illuminate the sample (the area of which illumination is referred to as the "footprint") is typically desired to be spatially flat and uniform. In many embodiments the devices/systems herein take advantage of properties of multimode fibers that allow propagation of all optical modes through their cores with near equal amplitude to produce a flat or top-hat profile illumination footprint from the laser on the illuminated substrate surface (e.g., the surface of a flowcell), etc. However, the finite number of modes present in such fibers can constructively and destructively interfere with each other and produce local minima and maxima in the intensity profile of the laser (or other light). See, e.g., FIGS. 33A and 34A which show minima/maxima resulting from uncorrected output from multimode fibers. To ameliorate this problem, some embodiments herein produce a substantially uniform footprint by use of dynamic mode scrambling by constantly changing the index of refraction within the illumination beam, e.g., by modulating the beam with a waveplate, or by shaking, squeezing or compressing one or more areas of a fiber carrying the illumination beam. Thus, some embodiments of the current invention produce a substantially uniform flat-top output (i.e., a substantially uniform illumination/excitation footprint from a laser or light source) by dynamically scrambling the modes in an illuminating beam, e.g., by squeezing/compressing a fiber carrying the beam in one or more area over its length. FIGS. 33 and 34 summarize various embodiments of mode scrambling as described herein. See below.

Dynamic Mode Scrambling and Low Loss Beam Shaping

In certain embodiments, the devices herein comprise component(s) to produce a "top-hat" illumination, e.g., a uniform or substantially uniform illumination over a particular illumination footprint, as seen in FIG. 35. Such embodiments comprise one or more aspects that dynamically change the index of refraction within the medium transmitting the illumination (e.g., a fiber) at one or more nodes. For example, a fiber can be squeezed at various locations along its length to induce a continuously changing index of refraction. Such squeezing of the fiber, e.g., a Step Index Fiber, can be used to spatially/temporally scramble the modes in the fiber to cause sufficient overlap over a desired integration time of the output illumination. As explained also herein (see below) the fiber can also be shaken, rotated, vibrated or physically deformed in other ways to change the optical path through the fiber.

In general, the dynamic scrambling of the modes in the fibers allows achievement of spatially uniform illumination over a minimum user defined integration time. This thus prevents interference of propagating modes of monochromatic light in multimode fibers which would produce light and dark patterns in the resulting beam. It is optionally sufficient that these modes disappear over the minimum integration time. Thus, in some embodiments, the relative path lengths of these modes within the illumination beam are rapidly varied by introducing time variable curvature and index variations into the fiber, e.g., by mechanical means.

It will be appreciated that several parameters of the dynamic mode scrambling can optionally be varied or can comprise a range of different configurations. However, in general, dynamic mode scrambling comprises one or more aspects/components used to dynamically change the index of refraction of an illumination beam in order to average out an end illumination footprint. While many existing refractive optical concepts require an input Gaussian beam and existing diffractive optical concepts are often wavelength dependent, the present embodiment does not require a Gaussian beam input and is wavelength independent.

In their various embodiments, the devices/systems herein desire a uniformly illuminated field for excitation/measurement of the sequencing reactions, etc. Thus, the uneven light/dark patterns that result from interference of propagating modes of monochromatic light in a multimode fiber is typically undesirable. Averaging of the light output over an illumination footprint (over a period of observation time such as the time captured by a camera during an imaging) to allow integration of the light means that the light/dark patterns "disappear" or are averaged out, and thus the excitation intensity seen by each fluorophore on the surface should be uniform.

Underlying dynamic mode scrambling, is the constant varying of the index of refraction at a point or node of the light beam over time (e.g., by physically squeezing a fiber over time) which causes the light to be scrambled and take different paths and thus averages out the light output in the illumination footprint. Thus, the position of interference minima and maxima changes as the index of refraction of the input beam is changed. If the index of refraction is changed at a frequency that is faster than the image acquisition time, then a spatially uniform image can be produced in the timescale of the observation.

It will be appreciated that the current embodiment should not be confused with the common usage of "mode scramble" which most often refers to randomization of an input mode or modes relative to the output. The desired function of the current embodiment is to temporally as well as spatially randomize modes, i.e., producing dynamic scrambling.

The dynamic mode scrambling of the current embodiment can also be used in conjunction with fibers comprising cores of particular shapes to achieve a beam shape with uniform illumination. For example, squeezing a fiber with a square core will result in a uniformly illuminated square beam. The beam can be shaped along a particular axis to make a rectangle, or oval shape, which beam is imaged as square or circular when it hits upon the imaging surface. See FIGS. 17-18. For example, rectangular beams can be generated from optical fibers, as shown in FIG. 34.

FIG. 35 shows the optical output from a variety of different lasers, fibers, and mode scrambling aspects, etc. During device operation, the ends of the fibers were re-imaged onto a beam profiler. FIG. 35 shows the effect of dynamic mode-scrambling (i.e., by manipulation of the fibers at one or more nodes with, e.g., piezo-electric actuators) by comparing the images from different wavelength lasers (e.g., 532 nm and 550 nm) and laser times (solid state and diode) in conjunction with different beam shapers (two versions of rectangles and a circle) by showing the output when the dynamic modescrambling is "on" versus the light output when the modescrambling is "off" for each laser type, etc.

It will be appreciated that one embodiment of the device can therefore comprise a dynamic mode scrambler as opposed to static mode scrambler. It is the dynamic variation of index of refraction that causes the modes to overlap over the desired integration time. The index of refraction is constantly changed at one or more location (node). For example, a fiber transmitting the illumination is constantly squeezed at a point with a changing degree of intensity (e.g., from no squeezing to maximum squeezing and back again). The fiber can be temporarily deformed by such squeezing so that its shape changes from a circle to an ellipse to a circle, etc. which, in turn, keeps changing the index of refraction. As soon as the squeezing stops, the mode scrambling stops.

Efficiency of averaging of the illumination output in a footprint depends on length of image capture, the degree of change in index of refraction, the type/strength of the light source, etc. Thus, it is a user controllable variable and should not necessarily be taken as limiting. The user can optionally control the degree of scrambling to fine tune the averaging of light output in a footprint.

Thus, the time period over which light output averaging is measured is variable, e.g., it can be the period during which an image is captured of the area illuminated by the light output (e.g., tiles (specific image capture areas) upon the flowcells in certain sequencing embodiments herein). In certain embodiments, the time period of scrambling efficiency is equivalent to or substantially equivalent to the expose period for each image captured by a camera (e.g., the CCD camera in particular sequencing embodiments herein). It will be appreciated that such exposure times can vary from embodiment to embodiment, e.g., from less than 1 millisecond to over 1 hour or more depending upon the particular requirements of the embodiment (e.g., at least 1, 5, 10, 25, 50, 100, 250, 500 or more microseconds; at least 1, 5, 10, 25, 50, 100, 250, 500 or more milliseconds; at least 1, 5, 10, 25, 50, 100, 250, 500 or more seconds, etc.). For the sequencing reactions described herein, the imaging time may be of the order of 50-500 milliseconds per exposure.

In various embodiments, the current dynamic mode scrambler can, no matter the overall system with which it is used, be used with different light sources/types, different beam media, different ways of changing the index of refraction, different numbers of nodes where the index of refraction is changed, etc.

Dynamic mode scrambling is not limited by the particular light/illumination used. Thus, for example, while many embodiments herein optionally use lasers of particular wavelength (e.g., 532 and/or 660 nm), other embodiments can use illumination of entirely different wavelength. The lasers used with dynamic mode scrambling can be, e.g., visible light lasers, IR lasers, narrow alignment lasers, broad linewidth lasers, etc. Again, while particular laser wavelengths are mentioned herein, such recitation should not necessarily be taken as limiting. Of course, it will be appreciated with each different laser type/strength used, that correspondingly, other parameters are optionally adjusted to achieve substantially uniform illumination. For example, the number of nodes where the index of refraction is changed and/or the rate of change of the index at such nodes is optionally different for different light sources to achieve the same degree of uniformity of the footprint.

Also, while the examples herein are generally addressed in terms of mode scrambling in fiber optic lines, dynamic mode scrambling is also optionally used with light transmitted through glass, plastic, non-fiber optic lines, air, vacuum, etc. Thus, dynamic mode scrambling is not limited by the medium in which the light is transmitted. Here too, differences in the transmission medium can optionally also match with a difference in other aspects of the mode scrambler needed to achieve substantially uniform output. For example, for light transmitted through air/vacuum (i.e., not contained within a fiber, etc.), the index of refraction is optionally changed/varied by changes in temperature rather than any mechanical change in the transport medium.

The index of refraction can optionally be varied through a number of ways. For example, as mentioned above, when the light is not transmitted through a cable/fiber, but rather traverses air/vacuum, the index of refraction of the light beam can be varied by changes in temperature. Thus, one or more heaters/coolers can he used to vary the temperature of one or more node of the light beam to change the index of refraction. For beams that travel through a fiber/cable, the physical properties of the fiber can be changed in order to vary the index of refraction. For example, the fiber can be physically bent, shaken, twisted, squeezed, compressed, pulled, or heated/cooled at one or more nodes to change the index of refraction at those points. The physical interaction with the fiber can be through actual mechanical manipulation (e.g., through rollers, pinchers, etc. and/or through piezo-electric actuators that squeeze the fiber (e.g., similar to those available from General Photonics (Chino, Calif.)), etc.). Generally, any way of varying the index of refraction can be used.

In addition to different ways of changing the index of refraction, the rate of change of the index, the number of nodes, etc. are also optionally variable. Thus, in different embodiments, dynamic mode scrambling can comprise one or more node (i.e., area where the index is varied) on an illumination beam, which node can be fixed/static or movable along the light beam. In a general, but not limiting sense, the greater the number of nodes, the more scrambling occurs. Similarly, for multiple nodes it is typically preferred that the changes in refraction not be synchronized with one another (i.e., it is preferred that the variation in index of refraction be random).

FIGS. 33-35 show examples of mode scrambling with various fiber shapes and various light sources. As can be seen from the images, substantially uniform "top hat" illumination is achieved when the dynamic mode scramble is performed using a vibrating or squeezed fiber. The figures also illustrate that images can be shaped through use of shaped-core fibers. FIG. 33 shows a nonscrambled beam output (A) compared with beam outputs wherein the fiber was shaken, e.g., through use of a MKIII MS from Point Source (Hamble, UK) (B), vibrated, e.g., with an MKIV MS from Point Source (C), or squeezed, e.g., through use of one or more piezo-electric squeezer/compressors (e.g., squeezed over 6 nodes at about 500-600 Htz. per node) (D). The results shown in FIG. 33 were all performed with the same fiber and laser types (e.g., 15 micron step index fiber and a 532 nm solid state laser). Similar results are shown in FIG. 34A-D for a rectangular core fiber: nonscrambled (A), shaken (B), vibrated (C), or squeezed (D). In FIG. 34 the examples were all done with the same fiber/laser types. FIG. 35 shows similar results on a number of different laser sources and scrambling procedures. Thus in FIG. 35 the panels correspond to: 660 um wavelength diode laser in a rectangular core fiber with no mode scrambling (A) and the same fiber with dynamic mode scrambling (B); a 532 um wavelength solid state laser with no mode scrambling (C) and the same fiber with dynamic mode scrambling (D); a 660 um wavelength diode laser (a second rectangular) with no mode scrambling (E) and the same fiber with dynamic mode scrambling (F); a 532 solid state second rectangular fiber with no scrambling (G) and with dynamic mode scrambling (H); a 660 um diode laser (round) with no mode scrambling (I) and with dynamic mode scrambling (J); a 532 um solid state laser with no mode scrambling (K) and with dynamic mode scrambling (L).

Low Loss Beam Shapers

In some embodiments herein, specific beam shapes such as a square or rectangular laser beams are optionally used. Such shaped illumination allows for efficient exposure and tiling over a surface, e.g., comprising a nucleic acid sample, which can result in higher throughput in various devices herein. This can be advantageous in cases where the imaging is performed using a CCD device with square pixels, as the illumination footprint and imaging area can be tiled to prevent illumination, and photobleaching of areas outside the image capture area.

In some embodiments herein, instead of using a mask to shape the beam and re-image the mask onto the sample surface (which can optionally waste energy outside of the mask), the laser is coupled into a square or rectangular (or other shaped) core fiber. Thus, all the available laser power is efficiently used for illumination. Propagation down a sufficient length of such shaped fiber fills the core efficiently to produce the desired illumination shape. The end of this fiber can then be re-imaged onto a sample, e.g., a flowcell substrate. In particular embodiments, such re-imaging of the illumination from the fiber is typically desired to not substantially disturb the top-hat profile and/or beam shape achieved from scrambling and/or beam shaping (or even to distort the beam when it has not been beam shaped or scrambled). Thus, re-imaging aspects (e.g., lens(es), etc.) are appropriately chosen to not distort the achieved profile and optionally to correctly magnify the light output onto the flowcell, etc. Re-imaging, in particular embodiments, can also be chosen to be achromatic (i.e., to be able to function with any wavelength light). In some embodiments, re-imaging components can also be "pistoned" by slightly moving the re-imaging components to have the illumination land properly on particular areas of the flowcell.

Illumination uniformity in such embodiments can optionally be controlled by the condition of the beam launched into the shaped fiber coupled with the length of the fiber. Illumination uniformity optionally can be enhanced by dynamically scrambling the modes within the shaped fiber. For example utilizing a device that continuously squeezes the shaped core fiber at various locations. See above. The delivered beam dimensions at the sample surface optionally can be manipulated by imaging lenses.

FIGS. 34 and 35 show the results of use of a rectangular core optical fiber. The end of the fiber was re-imaged onto a beam profiler. The image from the beam profile illustrates the desired rectangular beam with uniform illumination in the vertical and horizontal dimensions.

The dynamic mode scrambling and/or beam shaping systems comprise components to generate and deliver a substantially uniform and wavelength-switchable evanescent beam to the lower surface of a flowcell channel (or other substrate) in an SBS reader instrument. As is apparent, these components interface with several other modules/components in the overall SBS system (e.g., the various optics components described above, etc.), and can be controlled/directed through one or more computer component.

Even though the current dynamic mode scrambling and beam shaping embodiments include, and are described throughout in terms of their interaction with, nucleic acid sequencing systems (e.g., various sequencing by synthesis configurations as described herein), it will be appreciated by those of skill in the art that such embodiments are also applicable to a wide range of other uses/systems. Thus, dynamic mode scrambling can be included in myriad systems comprising one or more aspects to dynamically vary the index of refraction of an illumination beam to mix the optic modes of a multimode optical fiber in order to produce a substantially uniform image or output in a desired timeframe (e.g., such as during the image capture time for a camera or the like). Dynamic mode scrambling can optionally be utilized with systems such as those tracking fluorescence on a plate or microarray or the like, i.e., uses that do not comprise tracking of sequencing reactions.

Mode Scrambling Using Waveplates

In various aspects herein, the invention comprises a system for mixing optic modes in a multimode optic fiber through use of waveplates. Such systems comprise a light source (e.g., a laser) which sends light through a multimode optic fiber and also optionally through at least one waveplate and then optionally through a re-imaging lens(es), prism, and onto a substrate (flowcell). The waveplates in such systems can comprise "rotating" waveplates. In some embodiments the waveplates actually physically rotate at various rpms, while in other embodiments, such as with liquid crystal waveplates, the plate "rotates" and alters the polarization of the light passing through it by varying voltage across the liquid crystal. In certain embodiments, the waveplate comprises two or more sections of oriented retarders each of which rotates polarization in different directions. In typical embodiments, the light output from the fiber comprises a substantially uniform light output on a surface over a defined time period. The light output on the surfaces in various embodiments herein comprises reduced intensity minima and reduced intensity maxima in comparison to the output from a multimode optic fiber that does not comprise one or more rotating waveplates.

In other aspects, the invention comprises methods for equalizing light output from a multimode optic fiber over a surface in a defined time period by sending light from a light source (e.g., a laser) through a multimode optic fiber and through one or more rotating waveplates. In some embodiments, the output on the surface comprises reduced intensity minima and reduced intensity maxima as compared to the output from a multimode optic fiber that does not comprise one or more rotating waveplate. In some embodiments the waveplates actually physically rotate at various rpms, while in other embodiments, such as with liquid crystal waveplates, the plate "rotates" and alters the polarization of the light passing through it by varying the voltage across the liquid crystal. In certain embodiments, the waveplate comprises two or more sections of oriented retarders each of which rotates polarization in different directions.

As used herein in some embodiments, a "waveplate" (or retardation plate or phase shifter or the like) refers to an optical device that alters velocity of light rays as they pass through it, thus, creating a phase difference. Waveplates are typically comprised of a birefringent crystal. Some embodiments can comprise a liquid crystal waveplate.

As described above, in particular embodiments comprising laser or other source excitation, the illumination of the sample (the area of which illumination is referred to as the "footprint") is spatially flat and uniform. The optic instruments herein exploit the properties of multimode fibers that allow propagation of all optical modes through their core with near equal amplitude which produces a flat or top-hat profile of the footprint. However the finite number of modes present in such fibers can constructively and destructively interfere with each other, thus producing local minima and maxima in the intensity profile of the laser (or other light). Some embodiments produce a uniform footprint by physically shaking the fiber at a timescale shorter than the exposure time of the camera capturing the images, which averages the intensity minima and maxima and produces a uniform flat top footprint. This shaking can require an off balance DC motor that rotates and shakes the fiber, which in some instances can cause undesired noise and vibrations that need to be damped to avoid causing imaging problems. The shaking can also adversely affect reliability since off balance DC motors have a shorter mean time between failure than balanced motors, and may increase physical wear on the fiber. Because of these factors, mode mixing in a multimode optical fiber without mechanical vibrations and, in some instances without moving parts, by using waveplates can be advantageous in some instances.

One embodiment of the current invention produces a substantially uniform flat-top beam (i.e., illumination/excitation area or footprint) by mixing the modes of the multimode optical fiber using a rotating $\lambda/2$ waveplate (retarding plate). The spatial content of the modes depends on the state of polarization of the input light. As polarization is changed, the spatial content is changed. Thus, the position of interference minima and maxima changes as the polarization of the input beam is changed. If the waveplate is rotated at an angular frequency that is faster than image acquisition time, then a spatially uniform image can be produced in the timescale of the observation. Thus, in particular embodiments, the waveplate completes one or more rotation during a certain time period. The time period is, e.g., one during which an image is captured of the area illuminated by the light output (e.g., substrate areas of the flowcells in certain sequencing embodiments herein). Thus, in certain embodiments, the time period is equivalent to or substantially equivalent to the expose period for each image captured by a camera (e.g., a CCD camera in particular sequencing embodiments herein). It will be appreciated that such exposure times can vary from embodiment to embodiment, e.g., from less than 1 msec to over 1 hour or more depending upon the particular requirements of the embodiment (e.g., at least 1, 5, 10, 25, 50, 100, 250, 500 or more µsec; at least 1, 5, 10, 25, 50, 100, 250, 500 or more msec; at least 1, 5, 10, 25, 50, 100, 250, 500 or more seconds, etc.). For the cameras used herein, the exposure time may be 50-500 milliseconds. In certain embodiments the waveplates can rotate less than or more than a full rotation during the time period, thus, in some embodiments, aliasing can also be included.

Figure 38:
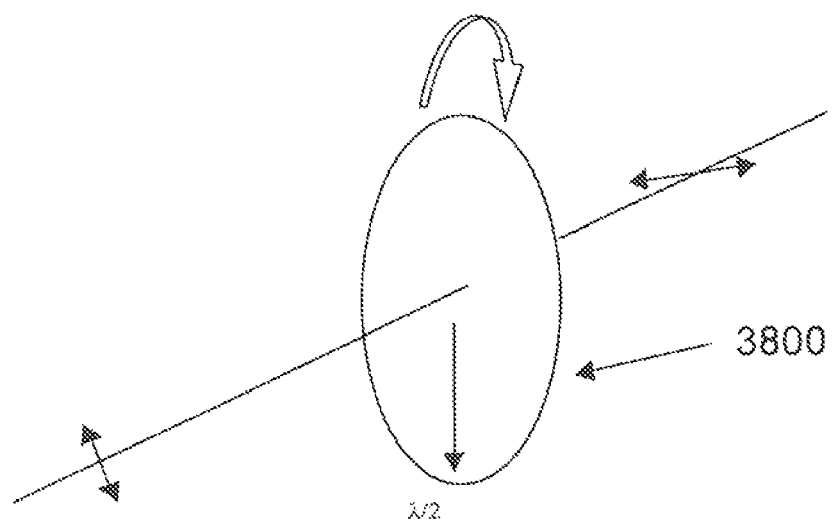
FIG. 38, shows a schematic of a λ/2 waveplate.
Figure 39:
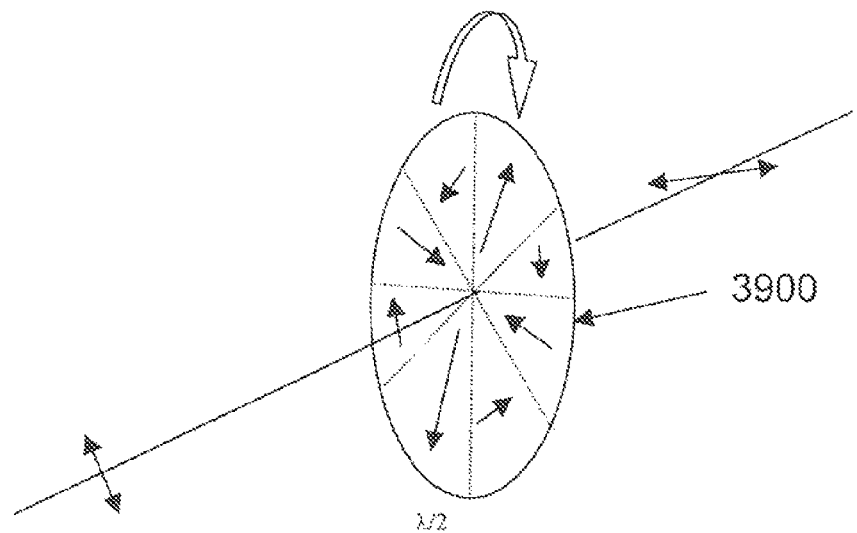
FIG. 39, shows a schematic of a λ/2 modified waveplate comprising a number of differently orientated sections.

While the rotation of the polarization can be accomplished by a number of ways, typical embodiments rotate the waveplate. In particular embodiments herein, a $\lambda/2$ waveplate (see waveplate 3800 in FIG. 38) in a suitable housing is rotated by a suitable DC motor or the like, operating at a speed fast enough so that a spatially substantially uniform image is produced during the appropriate image capture time. Other embodiments comprise modified waveplate(s) which consist of several sections of oriented waveplates or smaller pieces, with the fast axis oriented in different directions (see waveplate 3900 in FIG. 39). Since sections rotate the polarization in different ways/amounts, a much faster mixing of the modes can occur and the DC motor optionally does not rotate as fast as in the embodiments with several sections. In yet other embodiments, other devices, such as liquid crystals (such as, but not limited to, those manufactured by Meadowlark Optics (Frederick, Colo.)) can be used to rotate the polarization of the laser. With such liquid crystals, the polarization can be rotated by varying the voltage across the device.

Figure 40:
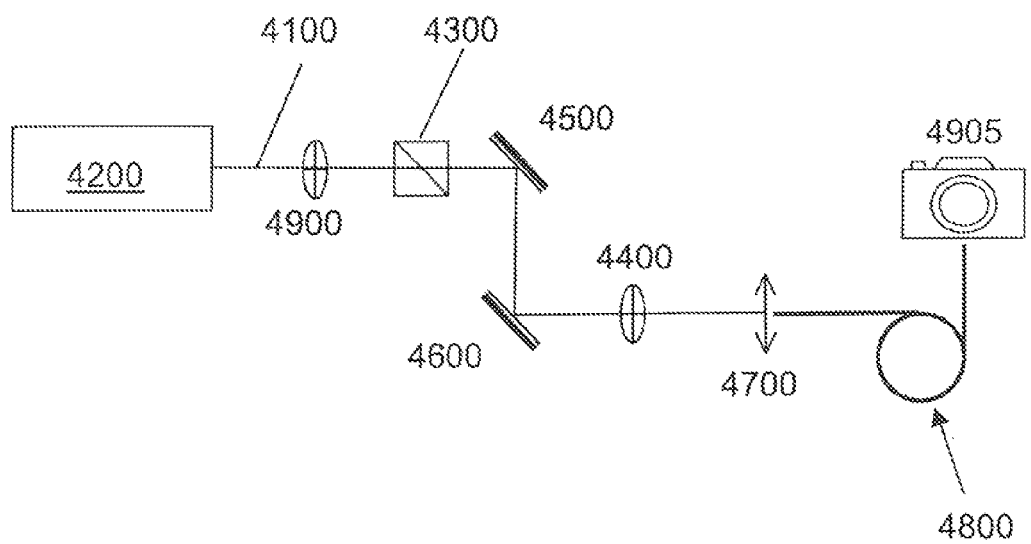
FIG. 40, shows an outline of a mode waveplate modulated mixing system of an embodiment of the invention.

FIG. 40 shows a schematic diagram representing an exemplary arrangement of an embodiment of the invention. In FIG. 40 linearly polarized light 4100 (200 mW, 532 nm) from diode pumped solid state laser (4200) is attenuated by use of several OD filters. The intensity of the beam is further controlled by λ/2 waveplate 4900 (e.g., Casix, Fuzhou, Fujian, China) and polarizing beamsplitter cube 4300 (e.g., Thorlabs, Newton. N.J.). In various embodiments, the entire laser intensity is not needed, thus, in the example described only about 0.1 µW is used. Rotation of the waveplate 4900 allows a precise control of the input laser power while keeping the polarization fixed. The beam is then passed through second λ/2 retarding waveplate 4400 and steered by two mirrors 4500 and 4600 into microscope objective 4700 (e.g., Nikon, 20×NA 0.3). The microscope objective reduces the beam to the required size to be accepted by multimode optical fiber, 4800 200 µm core, 0.22NA (e.g., OZ optics, Ottawa, Canada). The output end of the fiber in the embodiment shown is placed directly on the chip of CCD camera 4905 (e.g., Cascade 512, Photometrics, Tucson, Ariz.). In the exemplary embodiment shown, the camera was operated in frame transfer mode and exposures of 100 ms were adequate to capture the beam profile as explained herein.

In various embodiments, the current invention, no matter the overall system with which it is used, can comprise different waveplates (e.g., different in terms of type, placement, arrangement, construction, etc.), different mirrors and beam splitters (e.g., different in terms of type, location, angle, etc.). Thus, different embodiments can comprise, e.g., λ/2 waveplates, λ/4 waveplates (e.g., when the input polarization is circular), λ/n waveplates of other specific retardation, etc., and can comprise at least 1 waveplate; at least 2 waveplates, at least 3 waveplates, or at least 5 or more waveplates in various arrangements. The waveplates of the invention are not necessarily limited by their construction. Thus, solid crystal (e.g., crystal quartz, or any other appropriate substance) and liquid crystal waveplates are included herein.

While the current embodiment includes, and is described throughout in terms of its interaction with, nucleic acid sequencing systems (e.g., various sequencing by synthesis configurations as described herein), it will be appreciated by those of skill in the art that the current invention is also applicable to a wide range of other uses/systems. Thus, the embodiments can include systems comprising one or more waveplate (typically rotating) that mixes the optic modes of a multimode optical fiber in order to produce a spatially substantially uniform image or output in a desired timeframe (e.g. such as during the image capture time for a camera or the like). The current waveplate aspects can optionally be utilized with systems, such as those tracking fluorescence on a plate or microarray or the like, that is not a sequencing reaction. Correspondingly, the waveplate aspects can also include methods to create a substantially uniform image or output from a multimode optic fiber in a desired timeframe by passing the optic modes of the fiber through one or more waveplate (typically rotating and typically rotating at a speed faster than the image capture time or desired timeframe).

Figure 42A:
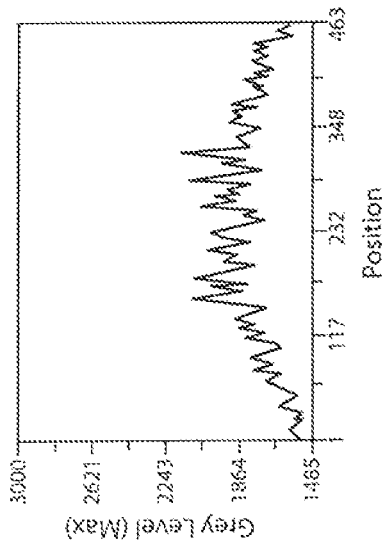
FIG. 42, Panels A and B display the substantial uniformity of a laser footprint area from multimode mixing through use of waveplates.
Figure 42B:
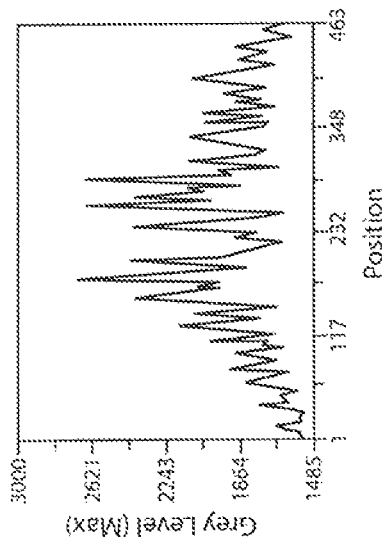

Various images obtained from exposure of a camera from such exemplary embodiments are shown in FIG. 41. From a single exposure, the prominent regions of bright and dark pixels are evident in FIG. 41A. The bright/dark images result from constructive and destructive interference of various modes that are present in the multimode optical fiber. Rotation of the waveplates results in spatial redistribution of the dark and bright regions as shown in the series of images in FIG. 41B. In such Figures, each image was taken at a different waveplate setting. As mentioned previously, if the waveplate is rotated faster than the image acquisition time, then the spatial profile is averaged and uniform smoothing of the image results. Such uniform smoothing is comparable to obtaining a large number of images and averaging them. FIGS. 41C and 41D show a single image with its line profile (41C) and an average of 54 images with associated line profile (41D). FIG. 42, shows the substantial uniformity of the footprint produced by use of the waveplate(s).

Other methods of ensuring that the optical beam is uniform over the imaging footprint include the use of solenoids, rotation of the light beam in an electric or magnetic field using Faraday or Pockel cells, and reimaging the light after it has gone through a diffuser. The diffuser can be a holographic diffuser that would superimpose light waves originating at the end of the fiber (if fiber coupled) or at the laser (if no fiber were present) in such a way that the waves superimpose and produce the required beam shape. One such example is a diffuser with an intensity profile of sine(x)^2 (sine is sin(x)/x) which will transform a gauss beam into a top-hat beam.

The various mode scrambling aspects herein can optionally be controlled/manipulated through the one or more computer component and are typically coordinated/synched with the light illumination and light detection components (also typically by the computer aspects herein).

Devices for Detecting Fluorescence

Figure 29:
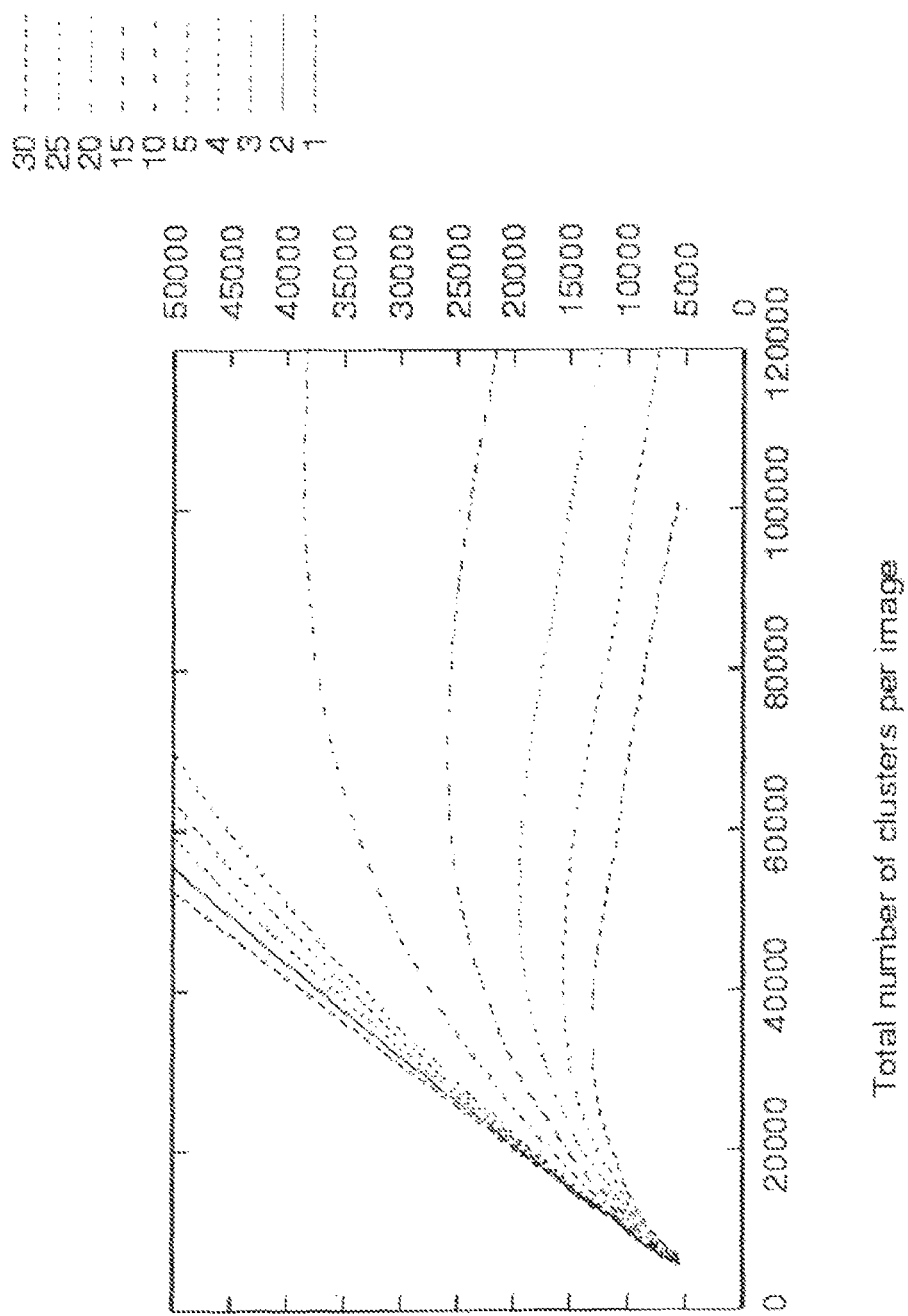
FIG. 29, shows a graph of the number of detected nucleic acid clusters as a function of total cluster number and minimum cluster area as detected by an embodiment of the invention.

There are numerous devices for detecting fluorescence, for example photodiodes and cameras, that can comprise the detection/detector component(s) of the current invention. In some embodiments herein, the detector component can comprise a 1 mega pixel CCD-based optical imaging system such as a 1024×1024 back thinned CCD camera with 8 µm pixels, which at 40× magnification can optionally image an area of 0.33×0.33 mm per tile using a laser spot size of 0.5×0.5 mm (e.g., a square spot, or a circle of 0.5 mm diameter, or an elliptical spot, etc.). The cameras can optionally have more or less than 1 million pixels, for example a 4 mega pixel camera can be used. In many embodiments, it is desired that the readout rate of the camera should be as fast as possible, for example the transfer rate can be 10 MHz or higher, for example 20 or 30 MHz. More pixels generally mean that a larger area of surface, and therefore more sequencing reactions, can be imaged simultaneously for a single exposure. This has the advantage of requiring fewer stage moves and filter wheel changes, and helps to speed up imaging. In particular embodiments, the CCD camera/TIRF lasers herein are capable of collecting about 6400 images to interrogate 1600 tiles (since images are optionally done in 4 different colors with optionally different filters in place) per cycle. For a 1 Mega pixel CCD, certain images optionally can contain between about 5,000 to 50,000 randomly spaced unique nucleic acid clusters (i.e., images upon the flowcell surface). The theoretical density of resolvable clusters per unit area (or image) is dependant of the size of the clusters, as shown in FIG. 29 which shows a 1 Mpix image of the number of detected clusters as a function of total cluster number and minimum cluster area. At an imaging rate of 2 seconds per tile for the four colors, and a density of 25000 clusters per tile, the systems herein can optionally quantify about 45 million features per hour. At a faster imaging rate, and higher cluster density, the imaging rate can be significantly improved. For example at the maximum readout rate of a 20 MHz camera, and a resolved cluster every 20 pixels, the readout can be 1 million clusters per second. The instrument can be configured to have more than a single camera. The light can be split to simultaneously image two colors onto two cameras, or even four colors onto four cameras. If four cameras are used in parallel, it is thus possible to sequence 1 million bases per second, or 86.4 billion bases per day.

Figure 36:
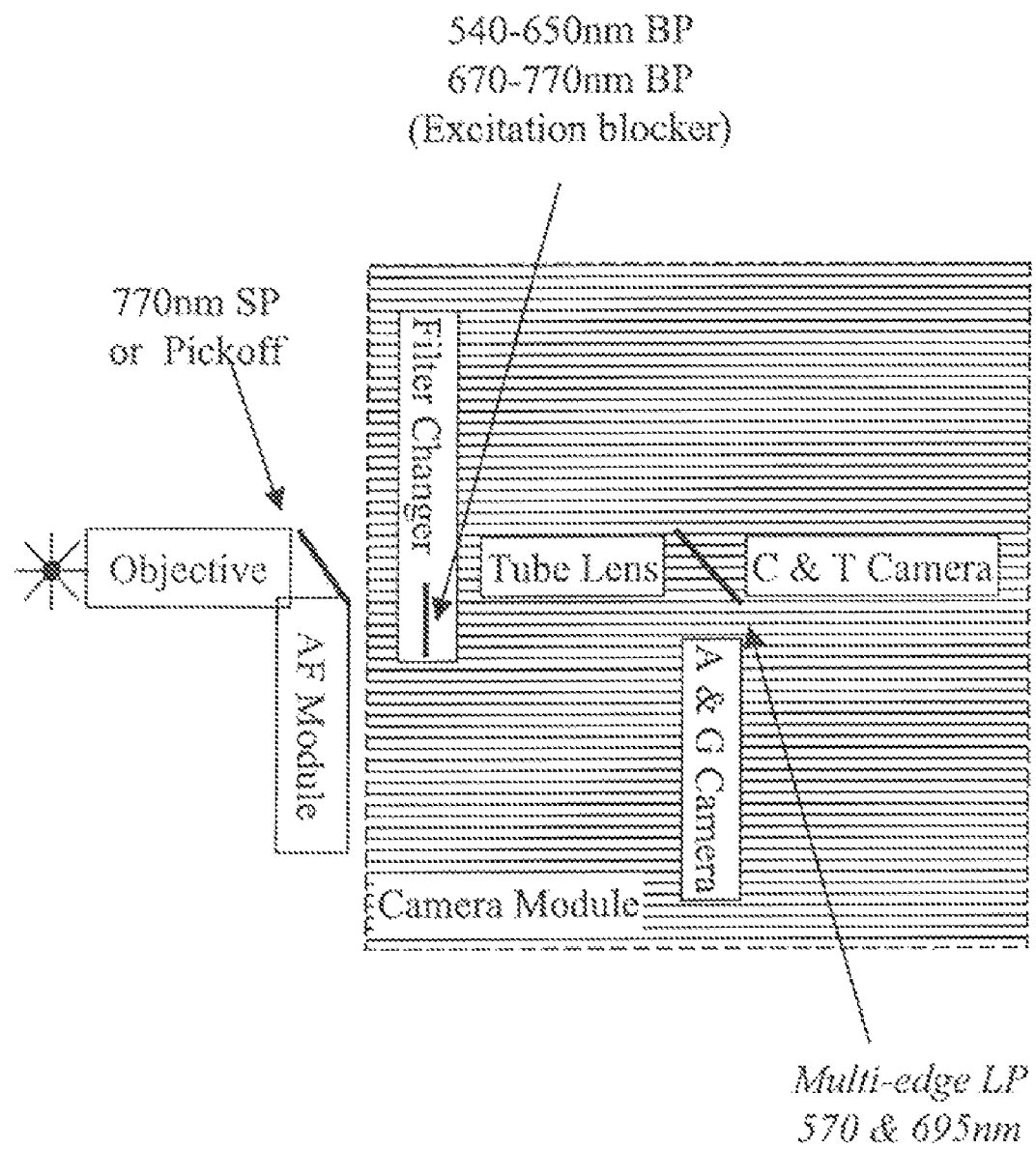
FIG. 36 shows one possible arrangement for a dual camera system embodiment of the invention.
Figure 37:
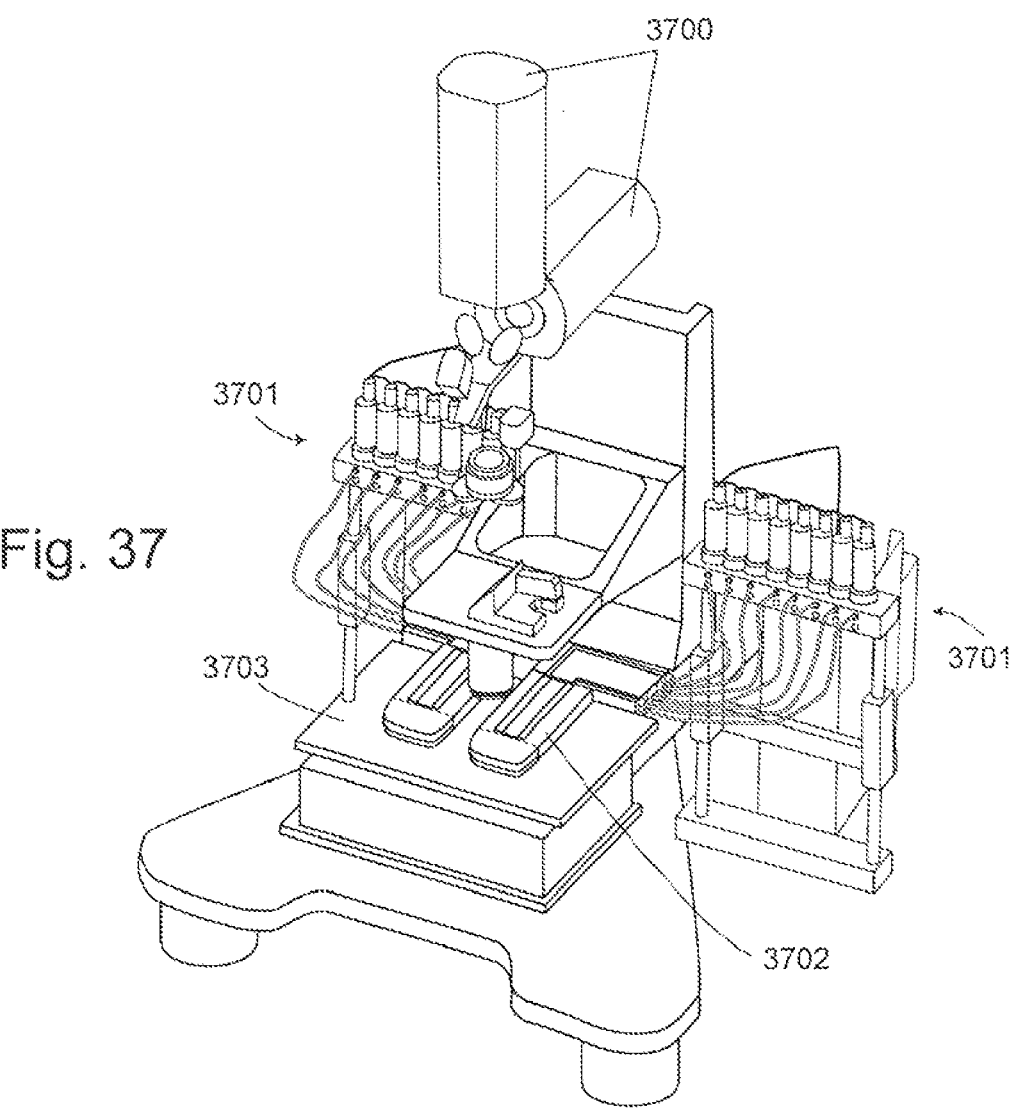
FIG. 37 shows an exemplary embodiment of the invention containing 2 cameras for simultaneous recording of 2 colors on the same image.

There are two ways of splitting up the optical signals for a two camera system. If two lasers are used, there may be a red excitation and a green excitation, with half the emission light split towards each camera. Alternatively both lasers may be used in both illumination cycles, and the light may pass through a suitable dichroic mirror, so sending the red light in one direction, and the green light in a different direction, as shown in FIG. 36. Such system prevents the signal losses associated with beam splitting, but does mean that two of the dyes are exposed to the laser before their intensity is recorded. In some such embodiments, the excitation blocker, e.g., as shown in FIG. 36 can comprise a dual notch filter (e.g., 532 and 660 nm). A picture of an instrument with two detection cameras 3700 and two fluidics systems 3701 (and two flowcells 3702) is shown in FIG. 37.

A "tile" herein is functionally equivalent to the image size mapped onto the substrate surface. Tiles can be, e.g., 0.33 mm², 0.5 mm², 1 mm², 2 mm² etc, although the size or the tile will depend to a large extent on the number and size of pixels on the camera and the desired level of magnification. Also, it will be appreciated that the tile does not have to equal the same size or shape as the illumination footprint from the laser (or other light source), although this can be advantageous if the minimization of photobleaching is desired.

As stated previously, in the various embodiments herein, the camera/laser systems collect fluorescence from 4 different fluorescent dyes (i.e., one for each nucleotide base type added to the flowcell). Again, additional material on other aspects of, and other concepts regarding, SBS sequencing can be found in applicants' co-pending applications, for example WO04018497, WO04018493 and U.S. Pat. No. 7,057,026 (nucleotides), WO05024010 and WO06120433 (polymerases), WO05065814 (surface attachment techniques), and WO 9844151, WO06064199 and WO07010251 (cluster preparation and sequencing).

Figure 13:
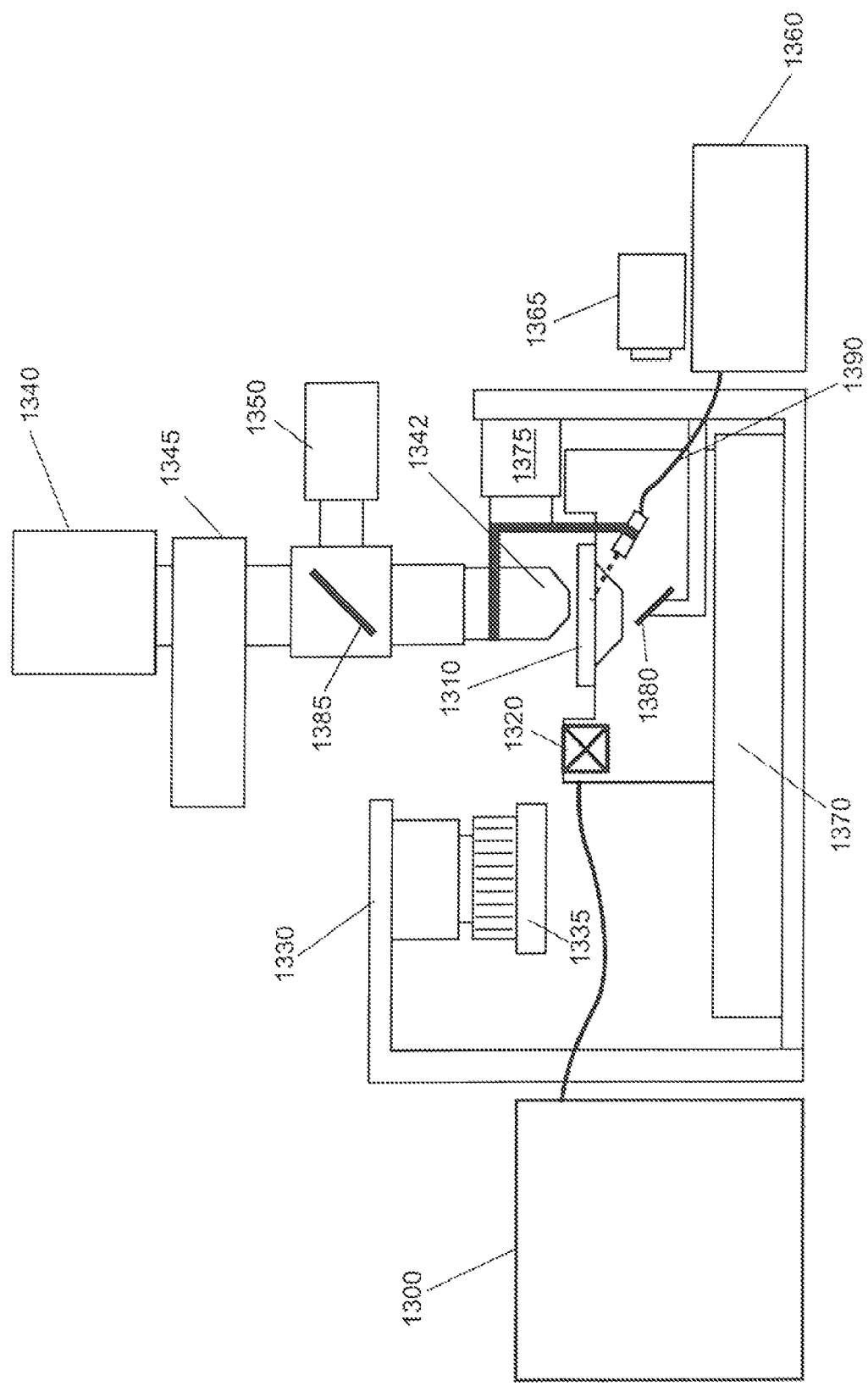
FIGS. 13-16, present various optional configurations of cameras, light sources, and other components in the systems herein.

FIGS. 1 and 13-16 show various possible configurations of the cameras and lasers of the present invention, including a backlight design, a TIRF Imaging configuration, a laser focusing configuration, a white-light viewing configuration, and an alternative laser focusing design. The white light excitation source is optional, and can be Used as well as, or instead of, the excitation lasers. FIG. 1 shows the backlight design system whilst recording an image in the TIRF imaging configuration. The configuration in FIG. 1 for the TIRF imaging is optionally a configuration of the backlight design set-up shown in FIG. 13. In FIG. 1, one of the two lasers (in laser assembly 160) is used to illuminate the sample (in flowcell 110), and a single one of the four emission filters (in filter switching assembly 145) is selected to record a single emission wavelength and to cut out any stray laser light. During imaging, both focus laser (150) and optional white light lamp (165) do not illuminate the sample as they are either blocked with a shutter or switched off. Laser illumination 101 and illumination from the flowcell up through the lens objective and camera 102 are also shown. FIG. 13 shows all the components of the system in the backlight design but without the specific TIRF imaging configuration. Cf. FIGS. 1 and 13. Thus FIG. 13 shows: fluid delivery module 1300, flowcell 1310, waste valve 1320, temperature actuator 1330, heating/cooling component (e.g., Peltier) 1335, camera (e.g., CCD camera) 1340, lens objective 1342, filter switching assembly 1345, focusing laser assembly 1350, excitation lasers assembly 1360, low watt lamp 1365, precision XY stage 1370, focus (z-axis) device 1375, mirror 1380, "reverse" dichroic 1385, and laser fiber optic 1390.

Figure 14:
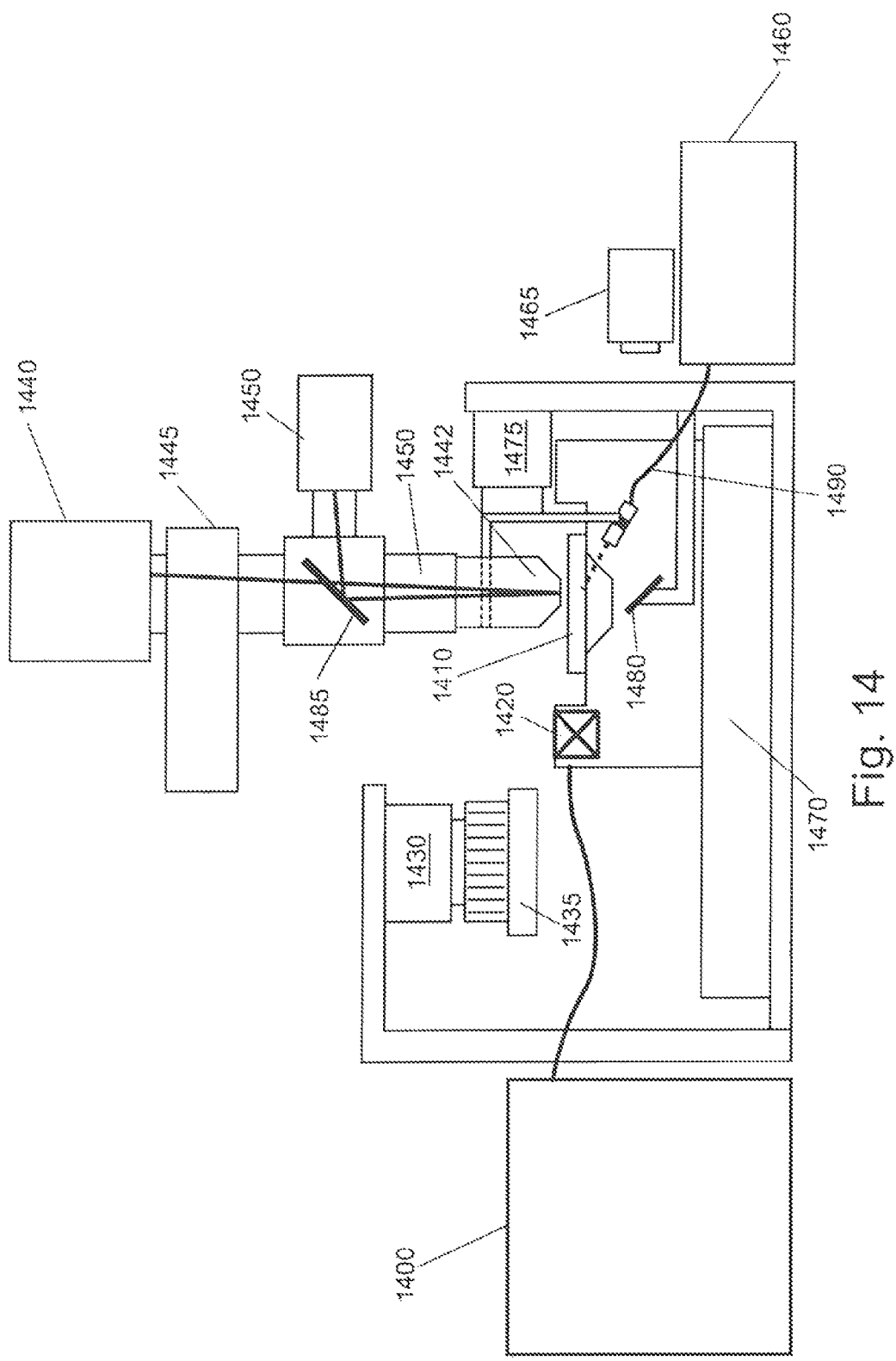

FIG. 14 shows a similar system as that in FIG. 1, but in the laser focusing configuration where the excitation lasers (in laser assembly 1460) and optional white light 1465 are switched off. Focusing laser 1450 is on and shines into the system, hits beam splitter 1485 (e.g., a pick-off mirror 1% beam splitter) which direct a faint beam 1402 down the objective to hit a small spot on the sample (in flowcell 1410). The scattered light from the sample returns up objective (1442) through an empty slot in filter wheel switching assembly 1445 and is imaged by CCD camera 1440. The position of the spot on the camera is used to ensure the sample is at the right distance from the objective, and therefore the image will be in focus. The numbering of the elements in FIG. 14 is similar to that of the elements in FIG. 13, but numbered as "14" rather than "13," e.g., 1460 corresponds to a similar element as 1360, etc. The autofocus system is described in more detail below.

Figure 15:
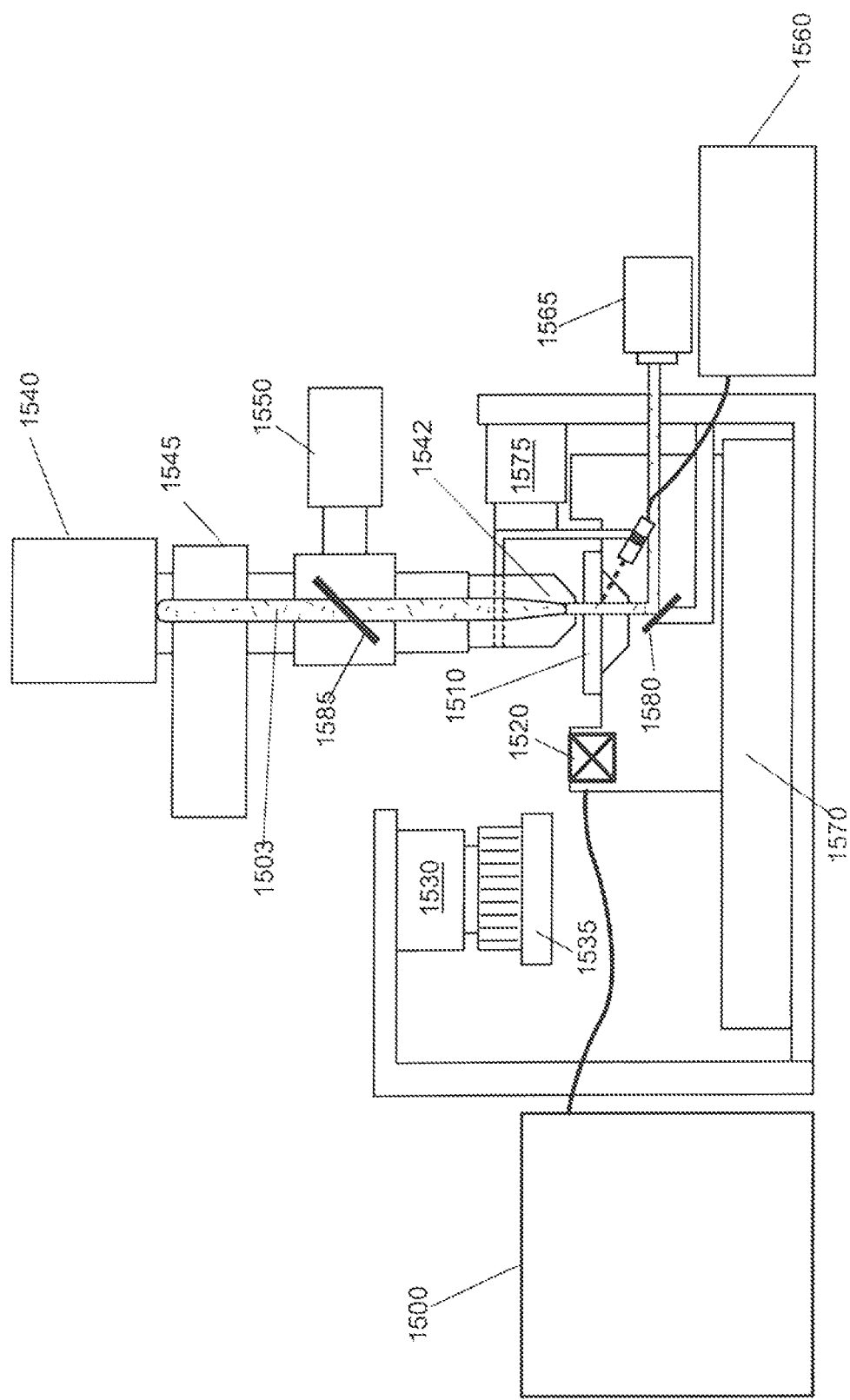
Figure 16:
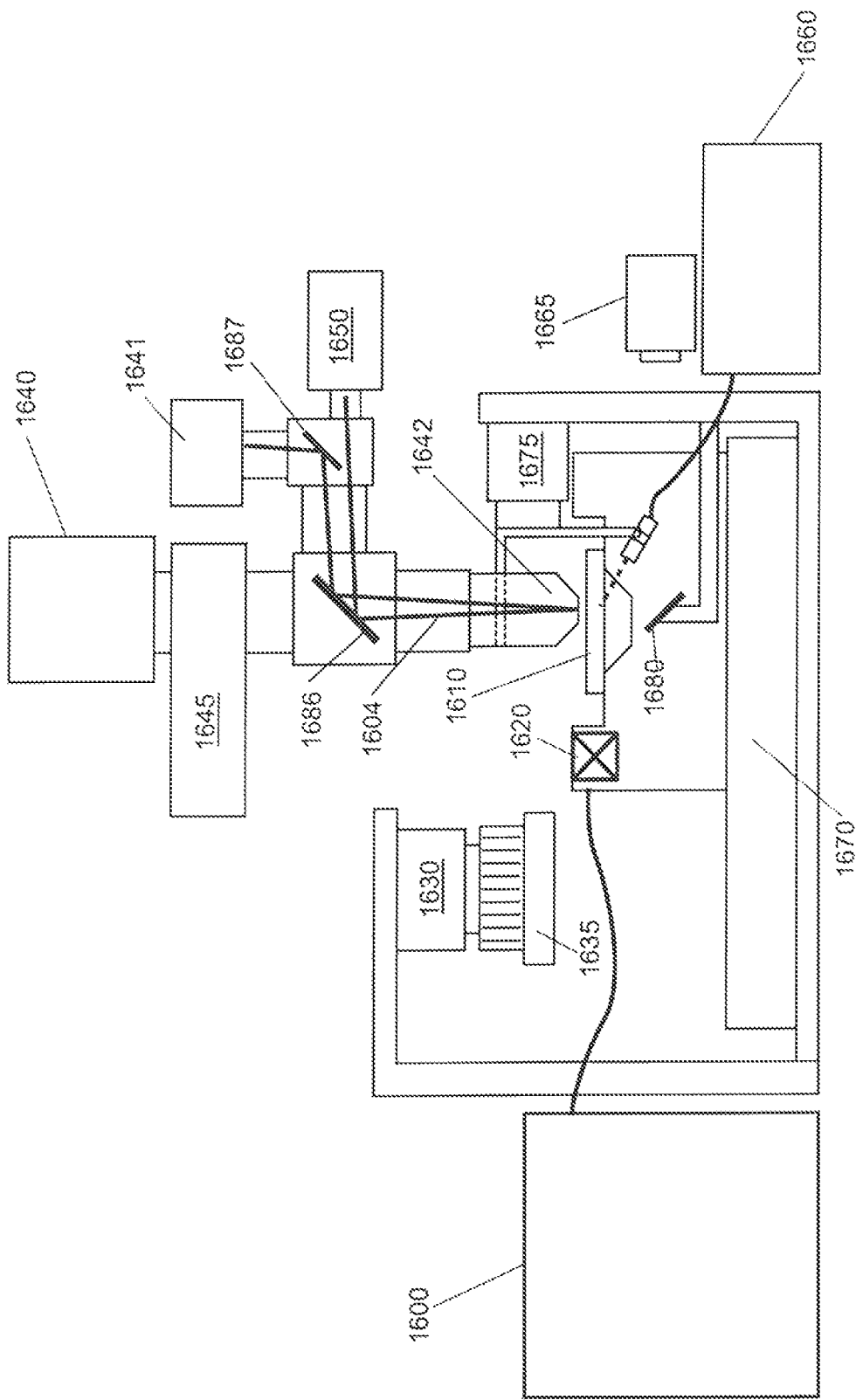

FIG. 15 shows the optional white light viewing configuration, where focus laser 1550 and illumination lasers 1560 are off. In such configuration the white light from low watt lamp 1565 goes into the system as beam 1503 and is imaged directly on the camera. Here too, the numbering of elements, except for beam 1503, etc., follows that of FIGS. 13 and 14. FIG. 16 shows an alternative focus configuration where the system contains second focusing camera 1641, which can be a quadrant detector, PSD, or similar detector to measure the location of the scattered beam reflected from the surface. This configuration allows for focus control concurrent with data collection. The focus laser wavelength is optionally longer than the reddest dye emission filter.

Figure 17:
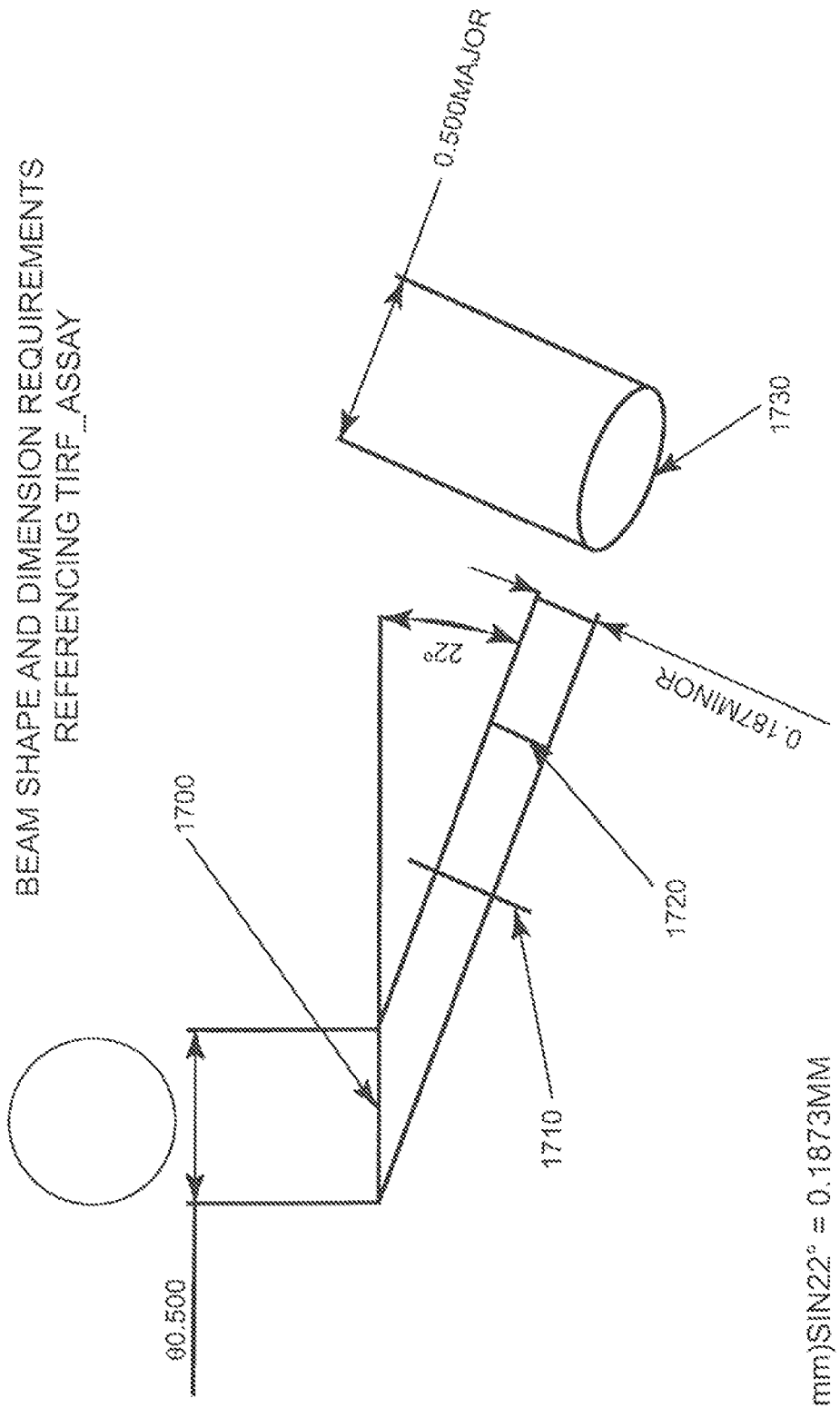
FIGS. 17-19, show various schematics for beam shape and dimensions for TIRF lasers in various embodiments of the systems herein.
Figure 18:
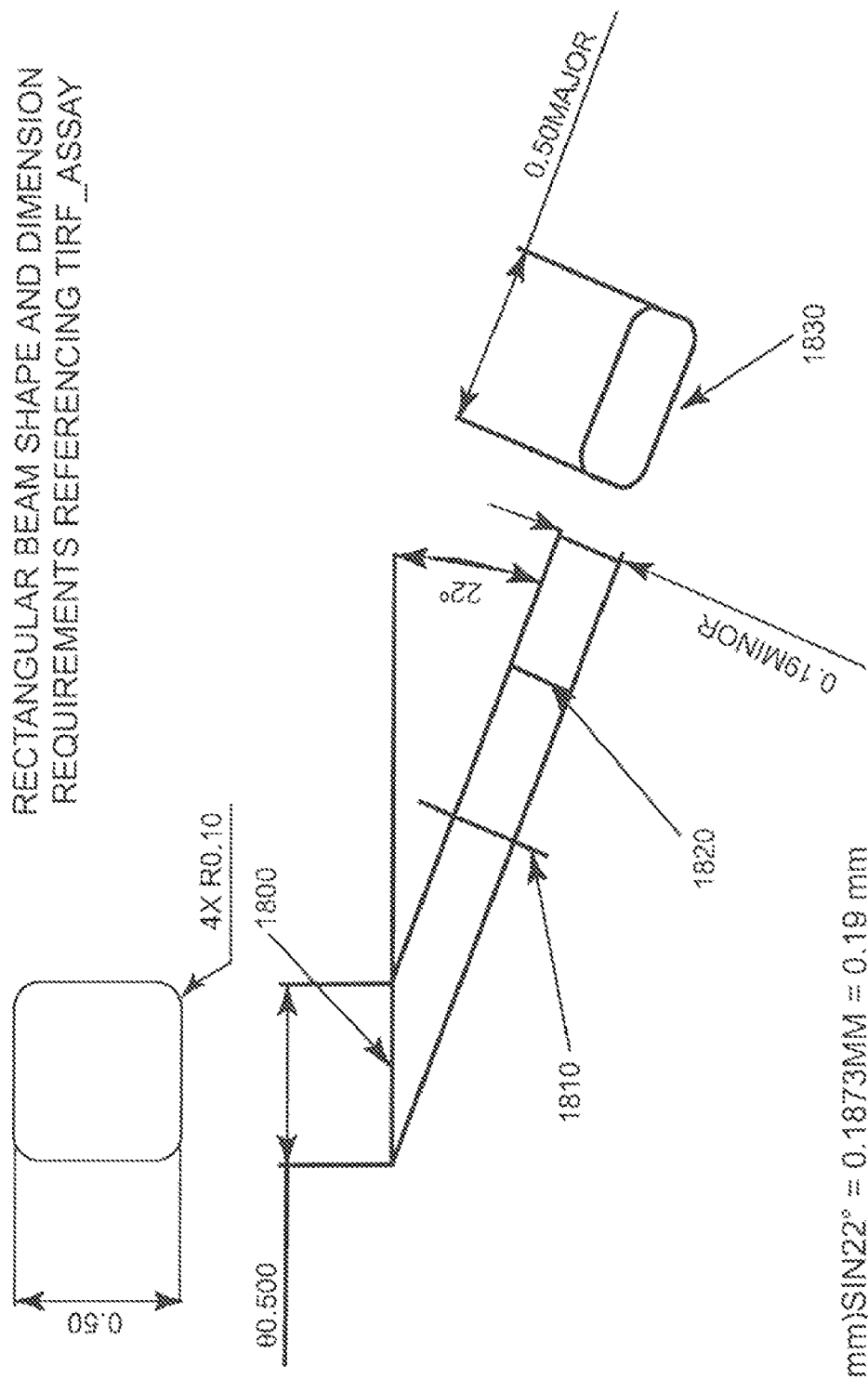
Figure 19:
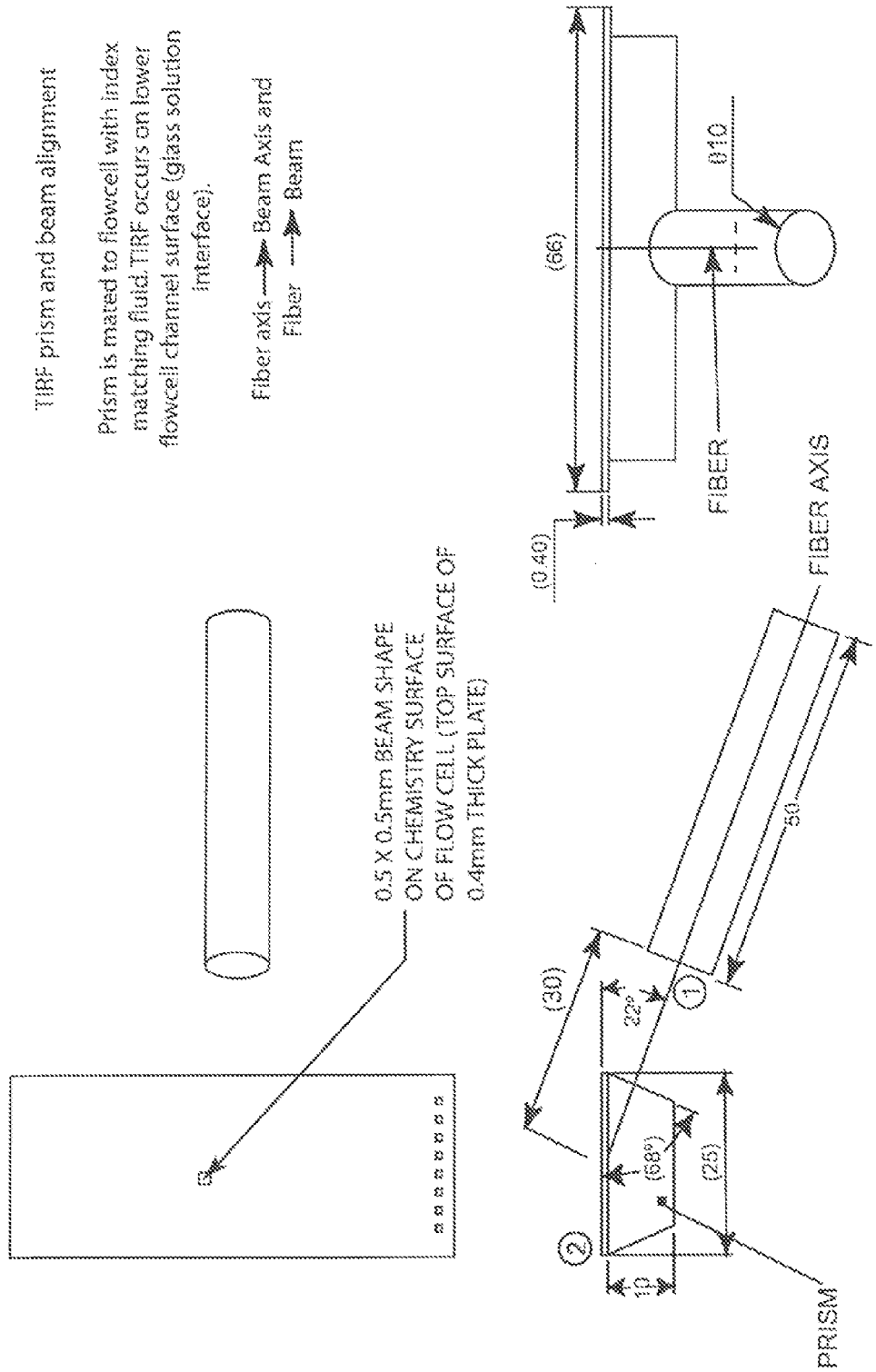
Figure 20:
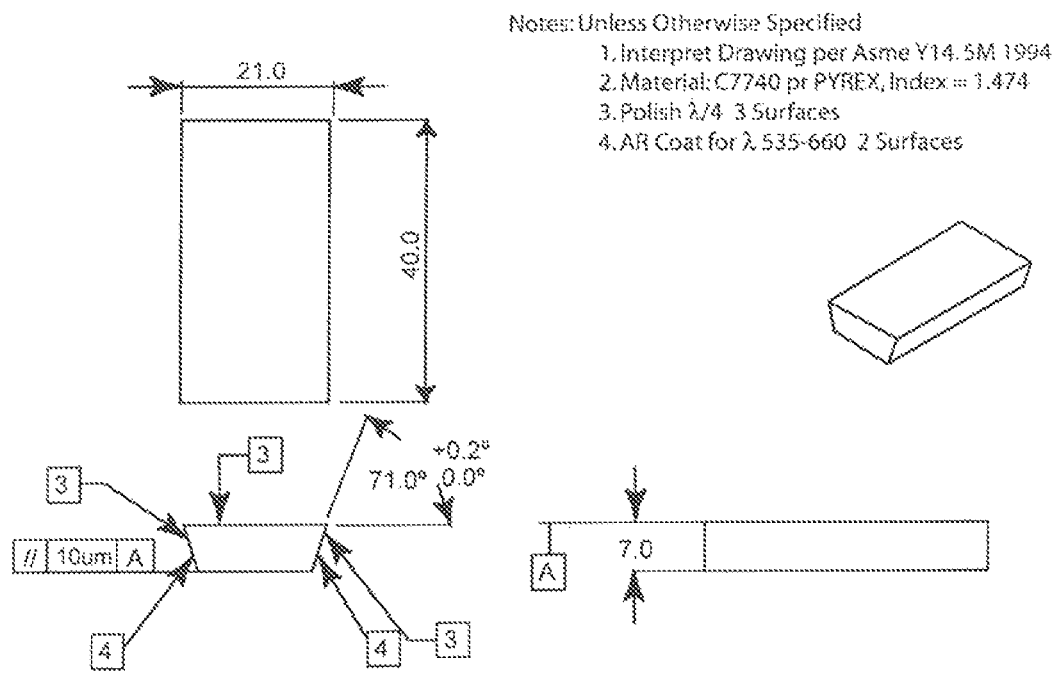
FIG. 20, displays an optional embodiment of a TIRF prism for use with the systems and devices herein.

FIGS. 17-19 show various schematics for beam shape and dimensions for TIRF assays carried out with use of the current systems herein, while FIG. 20 displays an optional embodiment of a TIRF prism for use with the systems herein. Thus it will be appreciated that the shape (e.g., round, square, etc.) of the laser beams and/or of the imaging areas illuminated by the laser beams can optionally vary between different embodiments. FIG. 17 shows the dimensions and geometries of the beam as it emerges from the fiber. In order to illuminate a circle on the substrate, the beam must be projected from the fiber as an ellipse since the beam hits the substrate surface at an angle to the normal. Edge view 1700 of circle projected by ellipse 1730 (e.g., an elliptical beam shape required at fiber exit (looking down fiber centerline at 22°). The prism face partial outline 1710 is not to scale and the edge view 1720 of ellipse 1730 is shown on the minor axis. Likewise in order to illuminate a square on the substrate, the beam must be projected onto the surface as a rectangle, as shown in FIG. 18. In FIG. 18, rectangle 1830 is shown. A rec-elliptical beam shape is required at fiber exit (looking down fiber centerline at 22°). Edge view 1800 of the square projected by rectangle 1830 is also indicated as is prism face partial outline 1830 (not to scale) and edge view 1820 of rec-ellipse 1830 (minor axis).

As shown in FIG. 19, the prism is designed to allow the imaging beam to hit the substrate surface at approximately 68° (relative to the normal) to achieve a total internal reflection and generate an evanescent beam that excites the fluorophores on the surface. To control the path of the beam through the prism, and therefore keep the illumination footprint directly over a stationary objective lens as the flowcell moves, the prism may have a geometry where the angle of the prism to the surface is also 68°, thereby ensuring that the light always hits the prism at 90°. The desired geometry of the prism is more fully described in application WO03062897. and the exemplary size and geometry is shown in FIG. 20, etc.

Figure 21:
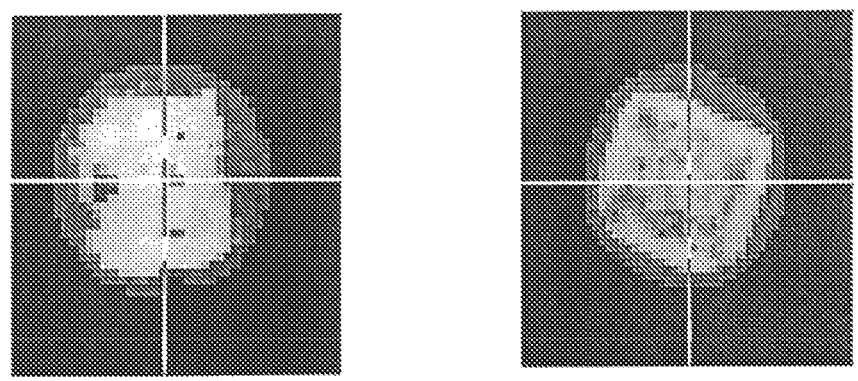
FIG. 21, illustrates creation of a square laser beam by polishing the end of a multimode fiber output.

Beam shape of the lasers herein is optionally controlled by polishing the multimode fiber output end in order to create, e.g., a square beam. See, e.g., FIG. 21. FIG. 21 shows imaged beam results from such polishing. In other embodiments, the beam is optionally round. In some instances, the beam properties may be a Gaussian profile with the following properties: a nominal image size of radius 0.17 mm, a maximal spot size of 0.25 mm radius, and 0.32 mm as the point after which there is effectively no laser intensity. In certain embodiments, the beam intensity is greater than 90% maximum intensity at all positions within the nominal image size; 80% maximum intensity at all positions within the maximal spot size, and no greater than 1% of maximal intensity outside of 0.32 radius. In various embodiments (in the absence of a dynamic mode scrambler), the intensity at any point does not vary by more than 5% RMS within the timescale of 1 s-1 h and the variation in the total (integrated) laser power is not more than 3% RMS measured over 24 hours.

Illumination Systems

A variety of illumination systems may be used in devices according to the present invention. The illumination systems can comprise lamps and/or lasers. The systems can contain one or more illumination lasers of different wavelengths. For example the systems herein may contain two lasers of 532 nm and 660 nm, although lasers with other wavelengths may also be used. Additionally, in various embodiments, the lasers in the systems herein are actively temperature controlled to 0.1 C, have TTL modulation for the 660 nm laser diode with rise time less than 100 ms; have integrated manual shutters for fast modulation of the 532 nm laser, have integrated beam shaping optics to ensure the optimum beam aspect ratio is maintained at the instrument interface to maximize signal to noise ratio, have integrated mode scrambler to reduce ripple on the output of the multi-mode fiber, and have minimal heat generation. The shutters and TTL modulation are used to ensure that the illumination is only on the sample surface whilst the camera is recording images. Illumination of fluorophores can cause photobleaching, and therefore exposure of substrates to the laser when not needed is generally minimized, especially before the images are recorded.

Figure 22A:
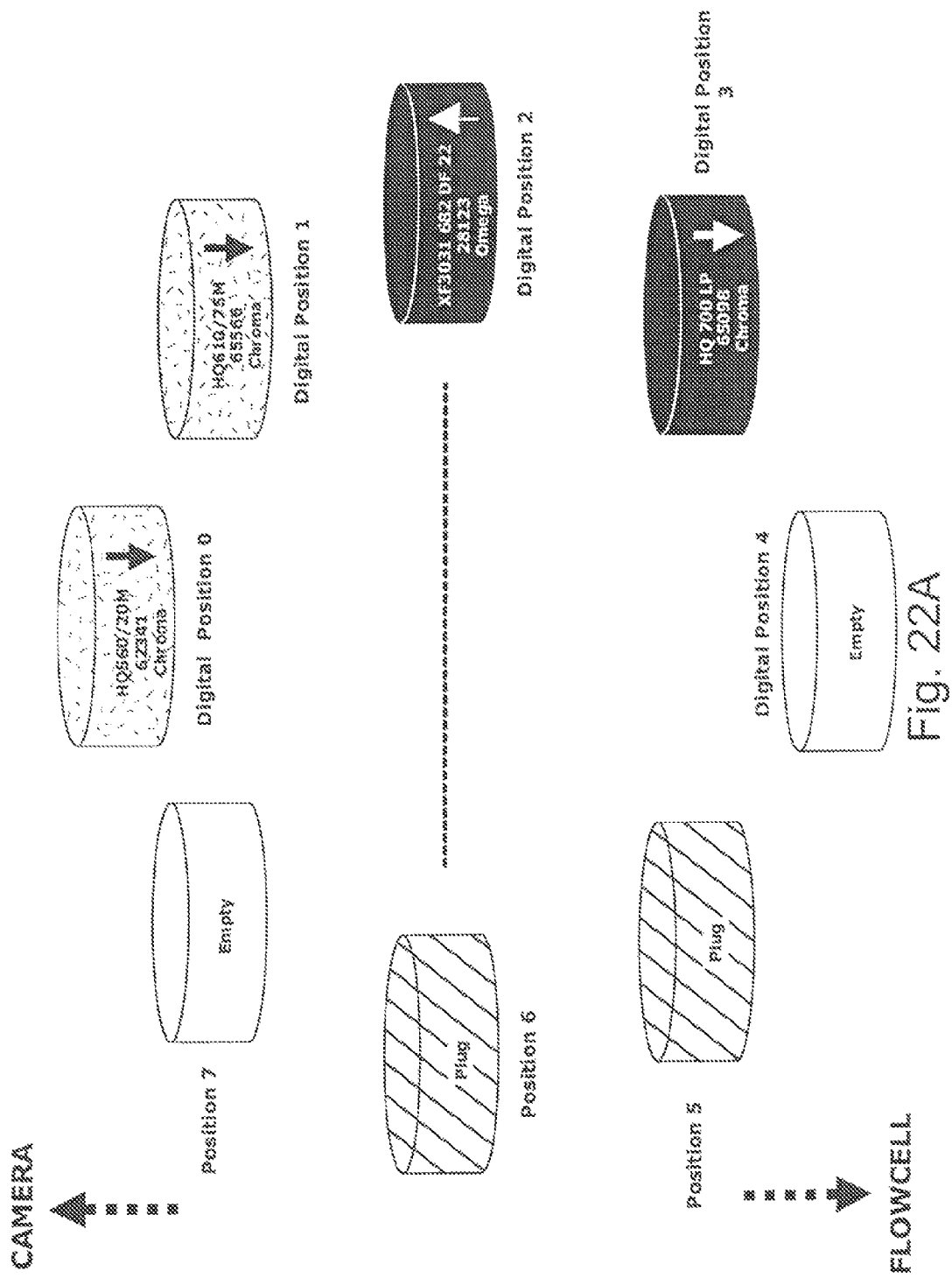
FIG. 22, Panels A and B, illustrate an exemplary filters and filter wheel configuration optionally within various embodiments herein (A), as well as the spectrum of those filters in relation to four exemplary fluorophores excited at the laser wavelengths (B).
Figure 22B:
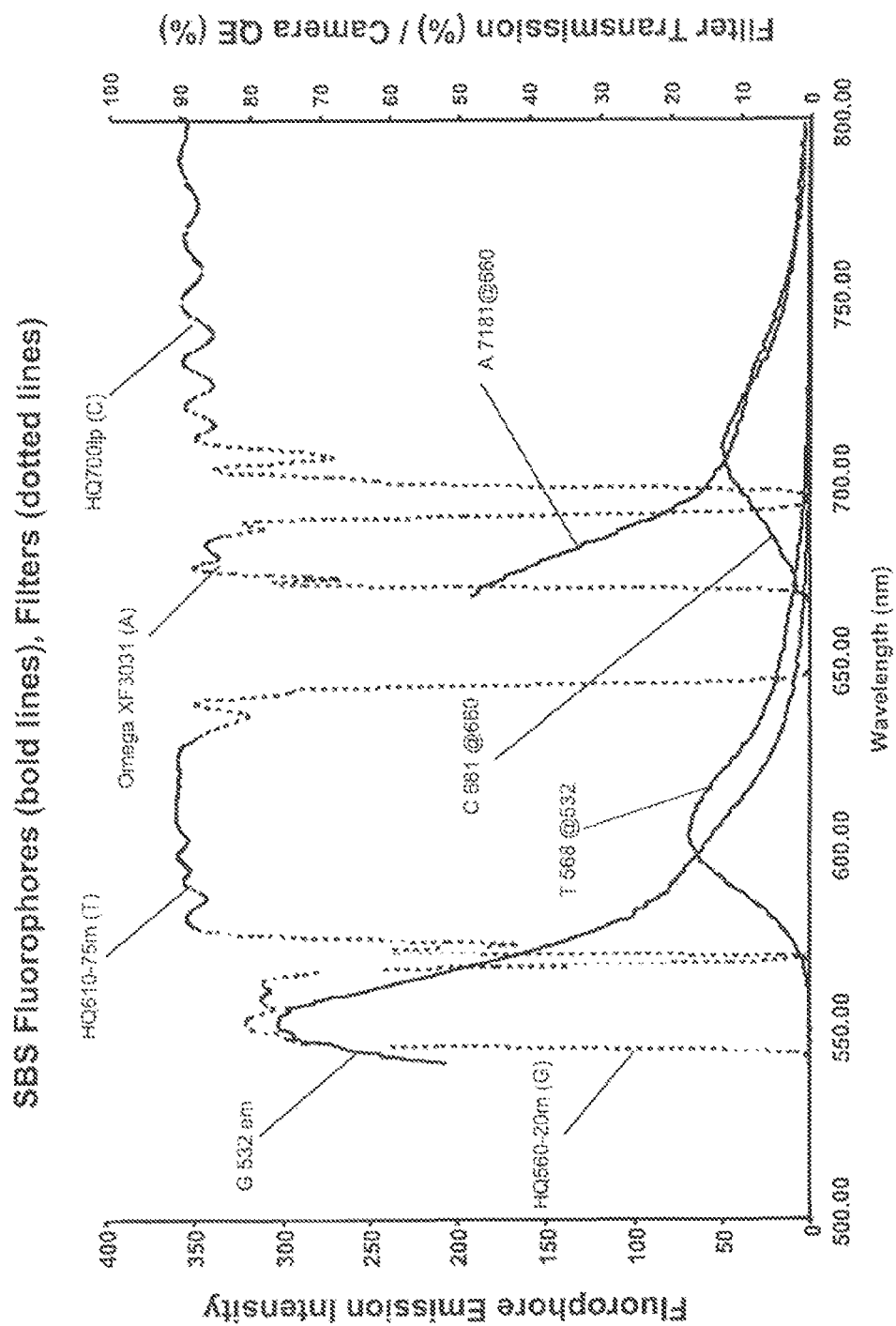

FIGS. 22A and B give various filter wheel arrangements of certain embodiments for use with various optic configurations. The use of a two laser excitation system to detect four fluorophores means that two of the fluorophores are excited away from their maximum absorbtion wavelength, as shown in FIG. 22B. If the emission filters used in all four channels were the same band width, then the two fluorophores nearest the 532 and 660 nm lasers would be significantly brighter than the two fluorophores excited further from the lasers. However, this factor can be negated by changing the bandwidth of the filters. For example, as shown in FIG. 22B, in the case of the 532 nm laser, dyes that absorb at for example 530 and 560 nm can both be excited by the 532 laser. The use of a narrow filter, close to the laser, for example a 560/20 that lets light through from 550-570 nm only allows the light from the 532 nm dye through. The use of a wider bandpass filter further away from the laser, for example a 610/75 that allows light through from 572 nm to 647 nm lets through the light from both fluorophores. The intensity of the 532 fluorophore through the 560/20 filter is similar to the intensity of the 560 fluorophore through the 610/75 filter. Thus the two fluorophores can be clearly distinguished using a single laser and two emission filters.

The effect is not wavelength specific, and can be performed using any excitation wavelength. The same effect can therefore be achieved using the red laser. Two fluorophores that absorb at 650 nm and 680 nm can be distinguished using a narrow filter close to the laser (for example a 682/22), and a broader filter further away, for example a 700 long pass. Again the intensities of the two dyes through their respective filters is similar, whilst the signal from the 680 dye in the 682/22 filter is much reduced. Both dyes emit into the 700 long pass channel, but the signals can clearly be determined due to the different level of emission in the narrow filter. The adaptation of laser wavelengths, fluorophore selections and filter bandwidths can be used to obtain a set of four fluorophores using any number of wavelengths, and the intensities of the emission through each channel can be normalized using the bandwidth of the filters to control how much light is transmitted.

Figure 23:
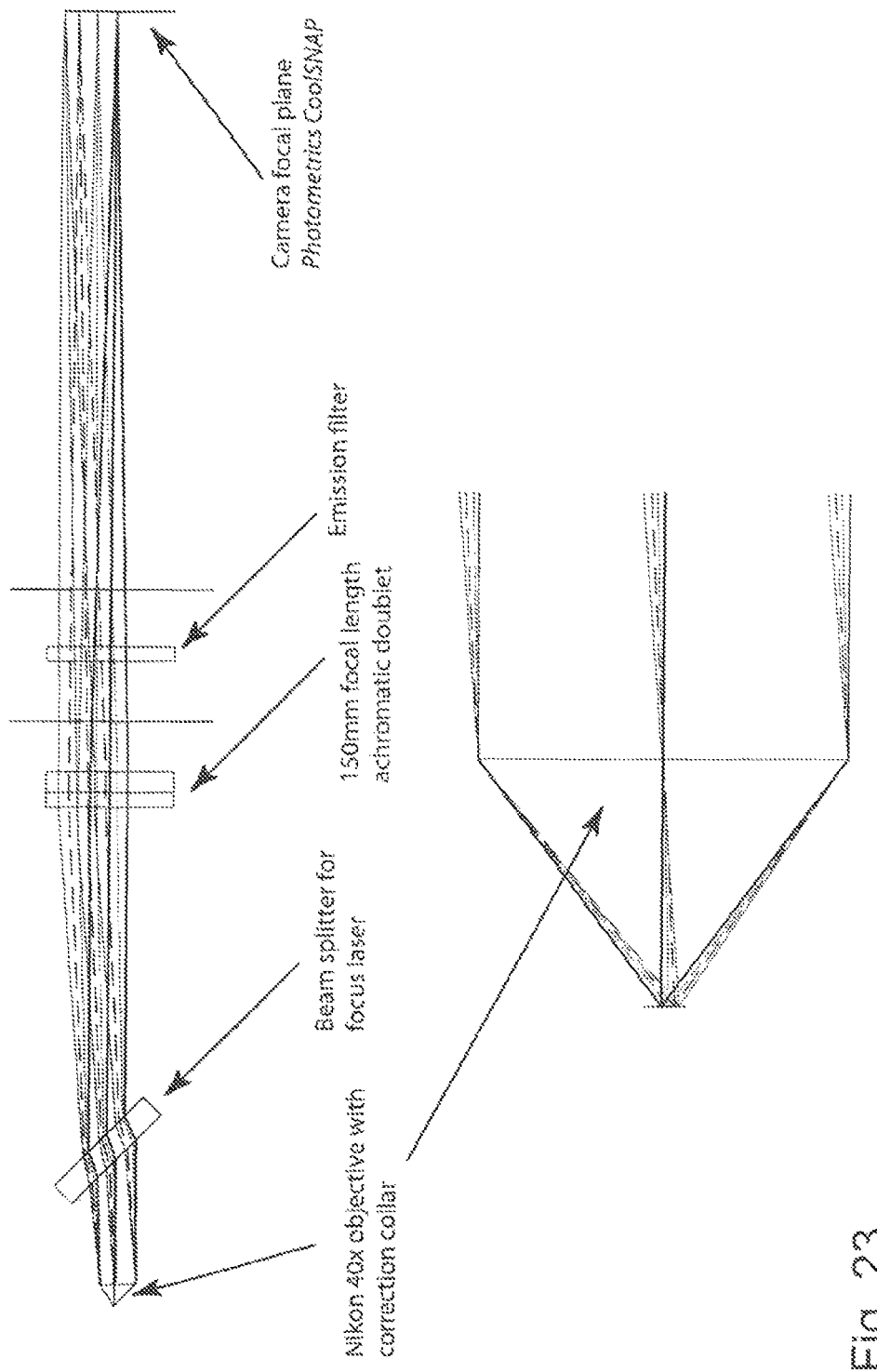
FIG. 23, illustrates an exemplary nominal 1G design, 30× K4 System Ray trace of the optic components of a system of the invention.
Figure 24:
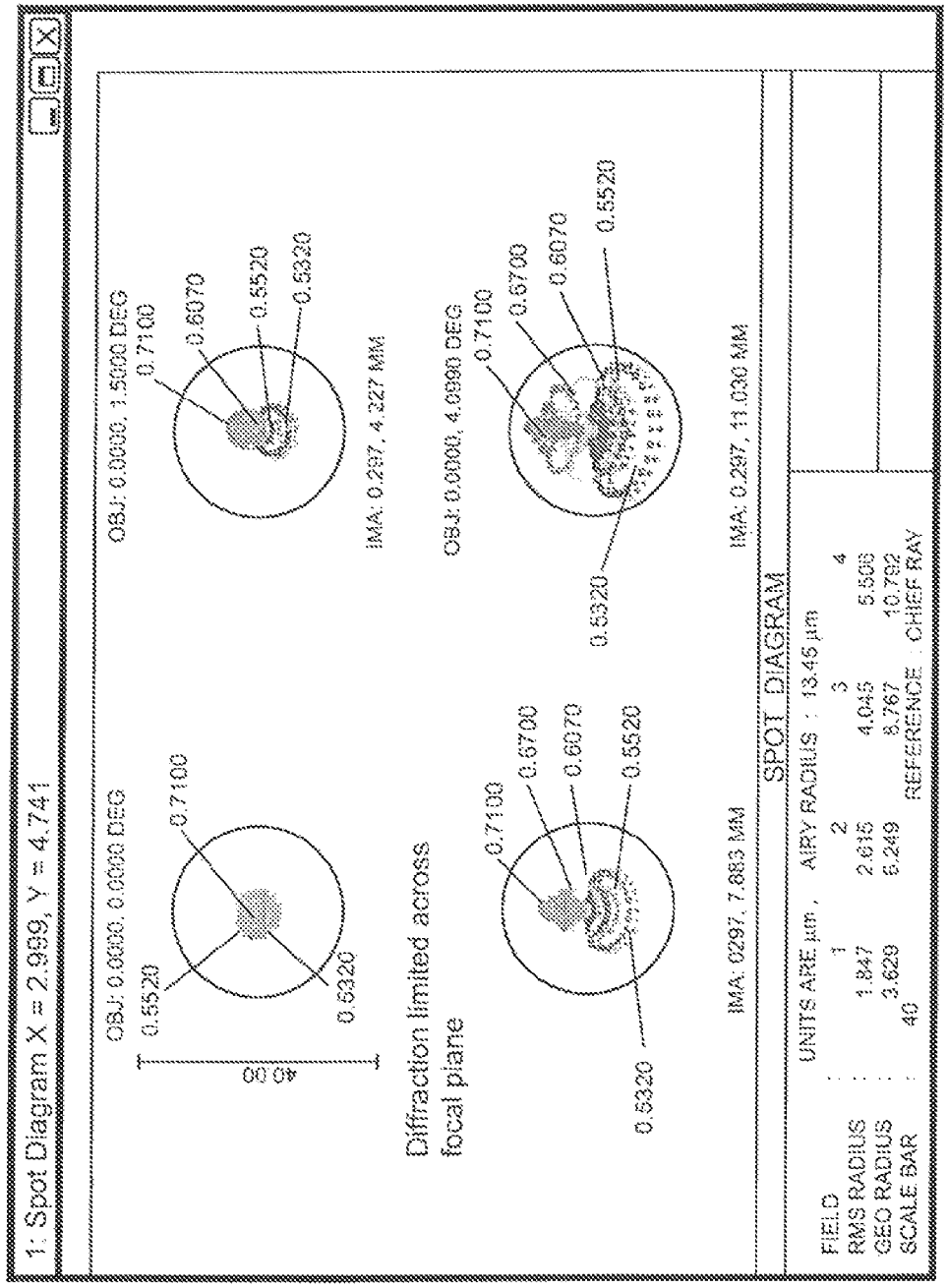
FIG. 24, shows the 30× K4 imaging performance of an exemplary system of the invention.

FIG. 23 shows a nominal design for an embodiment of the 30× system ray trace, while FIG. 24 shows the 30× imaging performance. The imaging performance of the system is dependent on the magnification of the objective lens, and the other lenses in the system. A smaller magnification will allow a larger area of the substrate to be imaged, but at a cost of resolution of closely packed clusters and the brightness of each cluster. A preferred magnification is optionally between 10×-40×, for example 20× or 30×. The objective can be custom designed to allow diffraction limited imaging to be retained when viewing fluorescence objects through a non-standard geometry (for example thicker glass substrates) and hence removing the otherwise present spherical aberration. The objective lens may be connected to the detector via a further tube lens.

Autofocus System

In particular embodiments, the systems herein can comprise components to aid in proper focusing of imaging clusters. In general, in particular embodiments herein, in an autofocus set up, an autofocus laser beam shines down to a sample through an objective lens, reflects from the flowcell surface, goes back to the lens and then to the camera, thus creating a spot on the image. When the objective is moved up/down with a fixed sample, the spot centroids align around a straight line on the image (calibration curve). Displacement "dr" along this calibration line is proportional to the change "d(z−zf)" in the distance between the objective and the focal plane. In many embodiments, before the run, the software establishes the orientation of the calibration line (its slope) and the "sensitivity": dz/dr (nm/pixel). This is accomplished by taking 21 images with the step of 1000 nm in z-direction around focus position which is established visually. The software also can require the x, y pixel coordinates of the spot when the sample is in focus: $x_f$, $y_f$, this is determined from the first (central) focus image from the set of the 21 calibration images. For example, the devices herein optionally comprise an auto focus function objective achieving 100 nm resolution mounted with up to 50 mm Z axis motion. The objective lens can optionally move vertically in relation to the substrate, and the illumination laser can be coupled to the Z axis motion such that the illumination inputs also move in relation to the substrate. For embodiments having autofocus capability, an auto focus beam is optionally sent along the edge of the microscope objective lens (optionally as far off-axis as possible in order to correspond to maximum sensitivity). The autofocus beam can come from the illumination lasers, or from a separate source that is optionally a different wavelength than the illumination laser, for example 488 nm, 630 nm or an infra-red laser of 700 nm or redder. The reflected beam is then optionally monitored by either a quad cell or by leakage through a dichroic beam splitter onto the fluorescence imaging camera. In such embodiments, the lens and camera are optionally the same as that used in the instrument (e.g., 20× lens). Similar autofocus systems which are optionally included within the current systems and devices have been previously described, for example in WO03060589.

Figure 26:
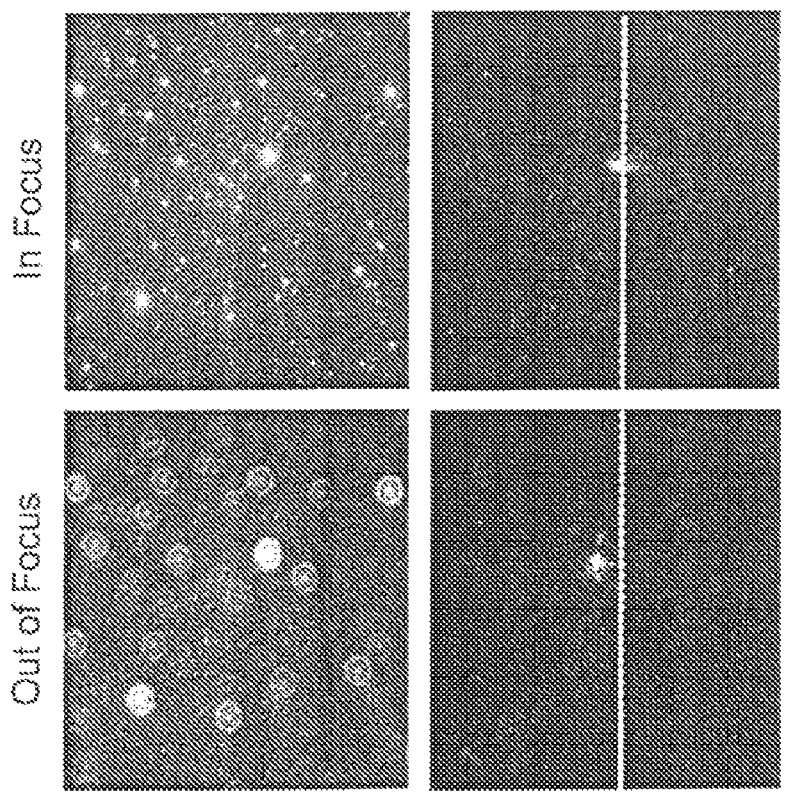
FIGS. 26-27, display photographs of focused and unfocused measurements made by various embodiments of the systems/devices herein.
Figure 25:
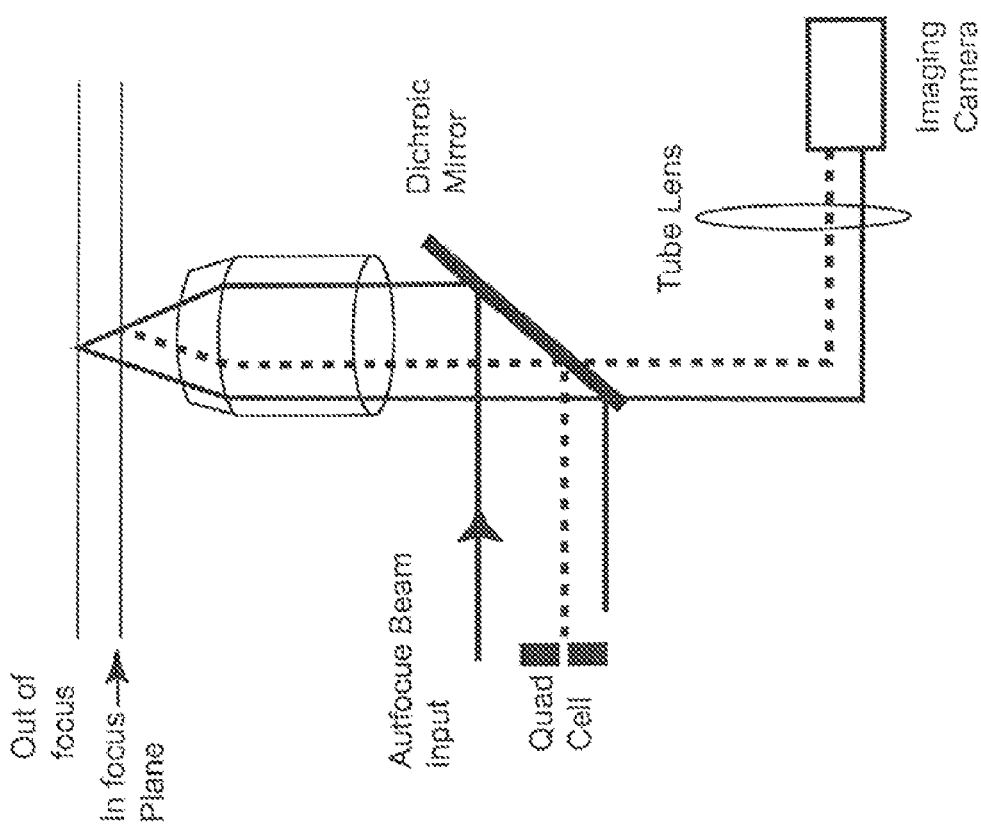
FIG. 25, presents a schematic diagram of an autofocusing feature of an exemplary system herein.
Figure 27:
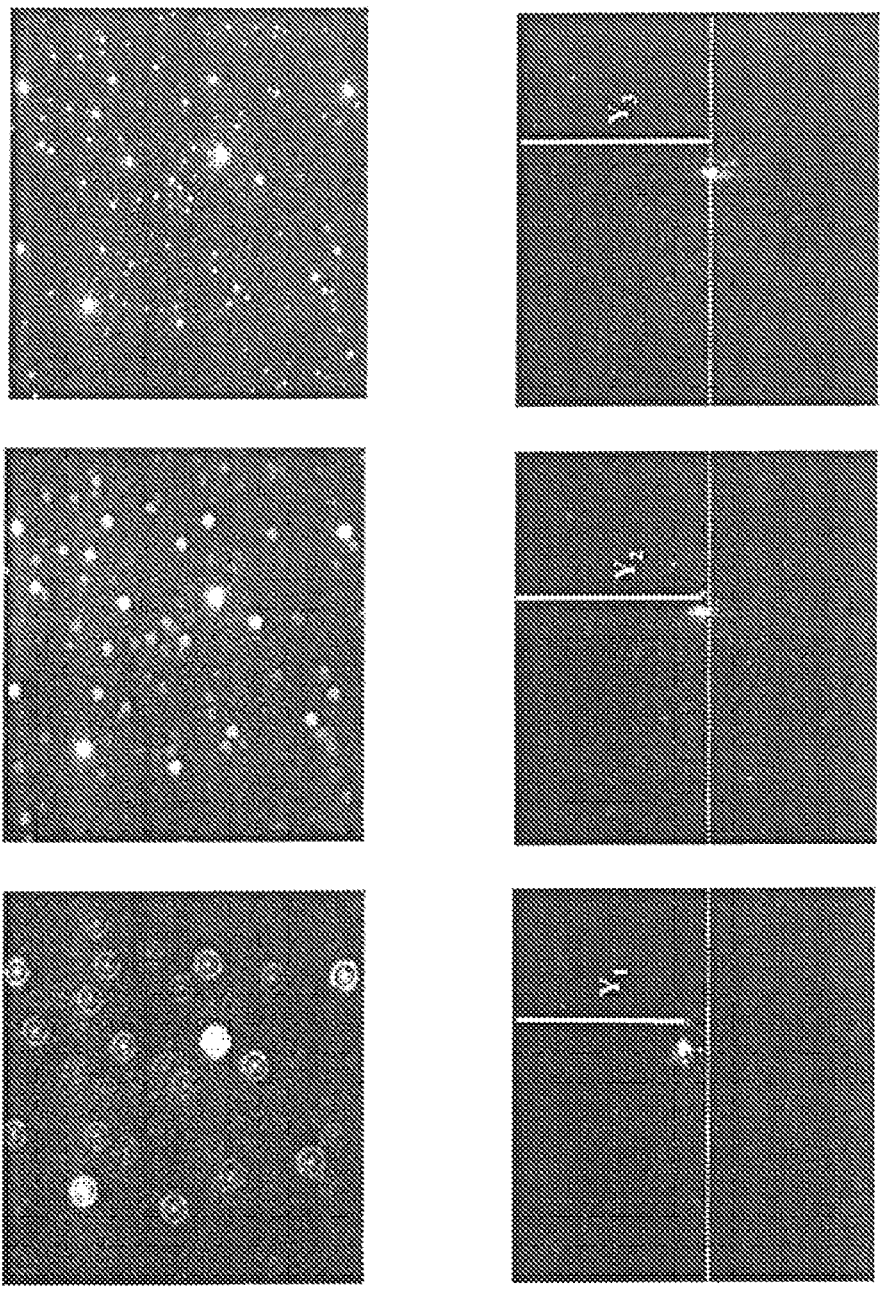

With particular autofocusing aspects herein, as the imaging plane moves with respect to the objective lens, the reflected monitoring beam also optionally moves laterally (i.e. dotted line is the in focus plane while the solid line represents an out of focus plane which gives rise to a lateral shift in the detected beam in FIG. 25). The dichroic mirror chosen in such embodiments is usually one that reflects the autofocus beam. The small leakage that is actually transmitted (c.a. <5%) is more than adequate to observe on a CCD camera with no emission filter in the emission path. FIG. 26 shows sample photographs of both out of focus and in focus images where the spot is seen on the imaging camera. The lower images show the detected autofocus spot on the imaging camera. The spot can also be seen on a separate detector, as shown in FIG. 27.

In embodiments comprising autofocus aspects, the computer component optionally comprises an autofocus algorithm. Such algorithms optionally aid in the determination of the correct focus (e.g., by monitoring the above measurements and adjusting accordingly). The autofocus spot can be made to move in a 1D manner e.g. in just the y-direction rather than x & y, thus simplifying the procedure. The focus position of the objective lens is assumed to move in the z-direction.

The first step in some embodiments of the autofocus analysis is a "Setup Response function" wherein positions of the autofocus spot $(y_1, y_2 \ldots y_n)$ are measured on the imaging camera for several positions of the objective lens $(z_1, z_2 \ldots z_n)$. Typically 5 positions are adequate. Shown in FIG. 27 is an analysis with just 3 positions. The movement of the reflected spot is shown as imaged on a fluorescence camera in the lower panels. For each Z plane there is an associated y-position of the reflected spot (centroid) on the camera. These five data points $(z_1, y_1), (z_2, y_2), (z_3, y_3), (z_4, y_4), (z_5, y_5)$ can be described by a line.

$$z = m y_0 + c \qquad \text{Equation 1}$$

The m and c values are given from the data points from least squares fits as:

$$c = \frac{\sum z \cdot \sum y^2 - \sum y \cdot \sum (yz)}{5 \sum y^2 - (\sum y)^2} \qquad \text{Equation 2}$$

$$m = \frac{5 \cdot \sum (yz) - \sum y \cdot \sum z}{5 \sum y^2 - (\sum y)^2} \qquad \text{Equation 3}$$

$$y_0 = -\frac{c}{m} \qquad \text{Equation 4}$$

Thus, from the 5 data points, the values of c, m and $y_0$ are determined giving a known response function.

The next step in such embodiments of the autofocus analysis comprises "Calculate newC (for out of focus position)" wherein for each position c is constant, i.e. doesn't change for an out of focus or in focus position. However, it does change for different positions. Hence as the stage moves to a new position NewC is calculated from the changed Z and y values as:

$$newC = Z_{measured} - m \cdot y_{measured} \qquad \text{Equation 5}$$

The third step in the process is to use newC to calculate required Z position (newZ) to get in focus y position ($y_0$). It is known that $$newC = newZ - m \cdot y_0 \qquad \text{Equation 6}$$

$$newZ = newC + m \cdot y_0 \qquad \text{Hence Equation 7}$$

m & $y_0$ are measured from step 1 (once per chip). newC is measured from step 2 (every position). Hence newZ can be calculated.

Figure 28:
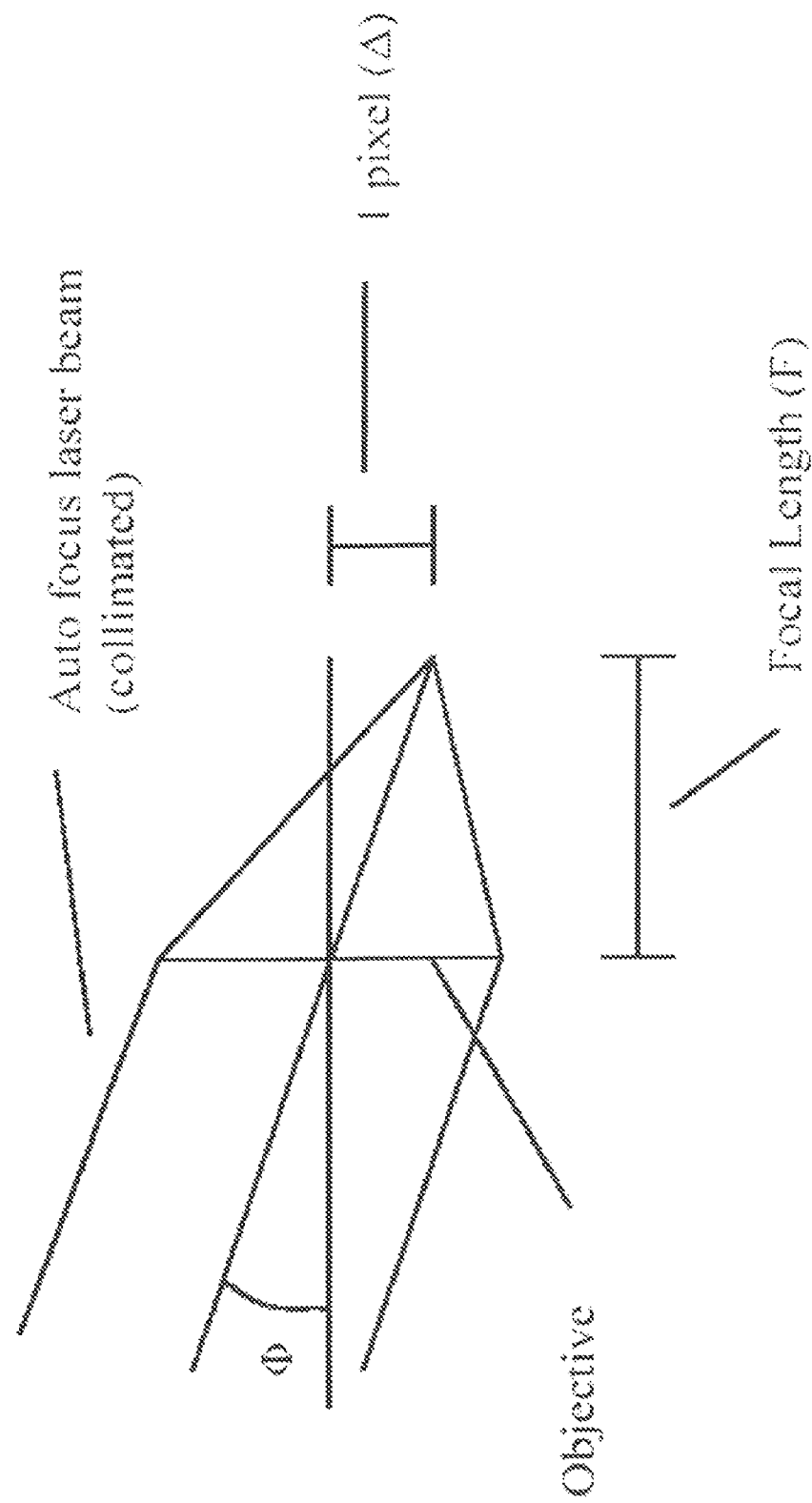
FIG. 28, presents a diagram of an auto focus laser beam.

Another aspect in auto focus components of the invention comprises laser pointing stability requirements. To assess how much pointer error can be tolerated in the auto focus laser, one can view the objective as a simple thin lens with the proper focal length as shown in the exaggerated drawing in FIG. 28.

Simple geometry y then yields that the angle Φ that would cause the auto focus laser beam to appear shifted by one pixel is simply at a (Δ/F) which is approximately Δ/F for small angles.

For a 20× objective (with the tube lens relay lens combination present in some embodiments) the pixel size is roughly 0.3 μm. The focal length of that lens is 10 mm. Hence the error angle that corresponds to 1 pixel is approximately 30 μrad. Some embodiments of the system have their auto focus set for a sensitivity of about 4 pixel shift of the auto focus laser spot per micron of z motion.

Assuming that 0.5 μm of focus error (corresponding to two pixels shift in the position of the laser spot) can be tolerated, it is seen that the biggest pointing change that can tolerate for the auto focus laser is 60 μrad.

To meet that sort of stability requirement over normal room temperature variations, it is highly recommendable to use a fiber optically coupled laser. Unless a solid state laser is very carefully temperature controlled, it will be difficult to maintain this sort of pointing accuracy within a reasonable ambient temperature spec range (e.g., 20-30 C.).

To provide additional information and theory in regard to focus tracking algorithms, a more detailed example of implementing the autofocus system is given below.

The first step in some embodiments of the focus tracking procedure is to obtain the image of the autofocus laser spot on an imaging device, which may be the imaging camera. Data from this primary spot is extracted in two passes—a first coarse pass that determines the approximate position and size of the spot, followed by a second fine pass that determines the spot boundaries correctly before determining the COL (Center of Light) and other spot features. The first pass analysis can be performed in 5 steps: (1) the 16-bit image is converted to an 8-bit image, with maximum of the image set to 255, minimum of image set to 0, and all other grayscale values linearly in between; (2) The Picture Quality of the image is computed. Picture quality is defined as the average of the normalized autocorrelation of the image with itself with shifts of unit pixel to the left and unit pixel down. If the image is noisy, then since noise does not correlate with itself, this measure will be low; (3) Next, this image is thresholded at 128. Anything above this value will be regarded as foreground, while anything below this level will be seen as background. Starting from the grayscale 255 (i.e. the hotspots), region-grow to find all 8-connected foreground components; (4) Of all these candidate foreground components, the component with the highest average brightness is chosen as "the" component specifying the position and approximate size of the primary spot; and (5) The bounding box of this component is computed.

The second (fine) pass analysis is performed in three steps: (1) The sub-image corresponding to twice the area of the bounding box is cut out from the 8-bit grayscale image. This makes the population of foreground and background pixels approximately equal, thereby making it easier for standard image histogram based thresholding techniques to work reliably; (2) The histogram of the subimage is computed and the "best" grayscale threshold that separates foreground from background is determined. The threshold used is called "Otsu's Threshold" (see *IEEE Trans. Systems, Man, and Cybernetics*, vol. 9, pp. 62-66, 1979, or *Computer and Robot Vision*, volume 1. Addison-Wesley. 1992.); and (3) The image is thresholded at the Otsu threshold and the 8-connected foreground component is determined. This is the primary spot blob on which every subsequent feature extraction is carried out.

An additional pass can be carried out to extract the position of the secondary spot. Four steps can be done to carry out such additional pass: (1) The 8-bit image (from the First Pass) is thresholded at a low threshold of 16; (2) It should be noted that at this lower threshold, the number of pixels (area) of the primary spot component increases. This area of the primary spot is recorded and is used to determine how tight or diffuse it is; (3) The component (of sufficient size) closest in distance to the primary spot component is identified as the secondary spot; (4) The geometric centroid of the secondary spot is recorded.

Center of Light Determination

To determine the Center of Light (COL) for autofocusing, $(\bar{x}, \bar{y})$ is denoted as the center of light of the primary spot. Then this is computed for the primary spot blob as:

$$\bar{x} = \frac{\sum g_i x_i}{\sum g_i}$$

and $$\bar{y} = \frac{\sum g_i y_i}{\sum g_i},$$

where the summation is taken over all pixels i in the blob having image based coordinates $(x_i, y_i)$ and grayscales $g_i$ (above threshold).

Other Spot Features

In addition to Picture Quality and the Center of Light, the list of features calculated for the primary spot blob includes Area which is a measure of how diffuse (non-tight) the primary blob is. This is set to the area (count in pixels) of the primary blob at the low threshold divided by its area at the Otsu threshold. Other features calculated include Volume (the average brightness, above threshold×Area of the primary blob); Average Brightness, which is the sum of the gray values of the pixels in the blob divided by its area; and Maximum Brightness: Maximum gray value.

The extracted data can then be used to calibrate the Z focus, and thereby determine how much, to move the objective in order for the image to be in focus. The overview of the calibration procedure is as follows: (1) Calibration for the Z focus is done (with user help) at the beginning of every run; (2) At the beginning of calibration the user makes sure that the image is in focus, i.e. at the focal plane. He/she thus sets the Z focus point $z_F$; (3) This embodiment of autofocus relies on user input and the coordinates of the autofocus laser spot on an image; (4) As z is changed during the Calibration process, the spot moves in linear proportion to the change of z along a line.

The calibration algorithmic procedure begins with a sequence of Center of Lights (x, y) extracted from the sequence of autofocus spot images acquired as z is changed.

Ideally these points when graphed should all fall perfectly on a straight line, shown below.

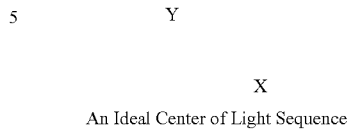

An Ideal Center of Light Sequence

Unfortunately, because of various noise sources, both physical and computational, the points are displaced from the ideal straight line, as shown:

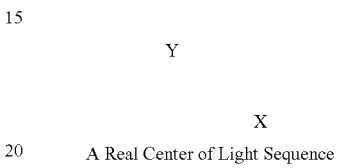

A Real Center of Light Sequence

Therefore an XY Principal Component Analysis (see e.g. I. T. Jolliffe, Principal Component Analysis, 2nd ed. Springer Series in Statistics, 2002.) based regression is performed between X and Y, leading to a new coordinates system R and Q as shown:

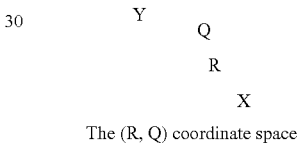

The (R, Q) coordinate space

It should be noted that: (1) Origin of the (R, Q) system is at the center of mass of the (x, y) points; (2) A best fitting (principal component) line defines the R axis; and (3) The orthogonal line to the R axis defines the Q axis. The model calls for high correlation between X and Y. The Q coordinate values can therefore be regarded as error "residuals" from the best fitting line—the idea is to get rid of these residuals and correct the observations.

Finally, since the model calls for a linear relationship between the spatial coordinates and the z values (as shown), a linear regression is performed between r and z to determine the coefficients of this line:

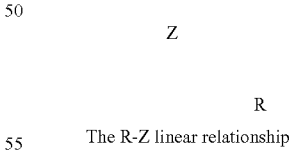

The R-Z linear relationship

Additionally autofocus tracking can involve various training of regression engines.

Training the XY PCA Regression Engine

| | |
|---|---|
| Input: | A sequence of Center of Lights (x, y) extracted from the sequence of autofocus spot images acquired as z is changed. |
| Output: | The PCA Regression Coefficients, i.e. transformation to the (R, Q) coordinate space. |

-continued

| | |
|---|---|
| Description: | Perform Principal Component Analysis and save the coefficients. Also, given the centroid position of the secondary spot, determine whether it is to the left or the right of the primary spot along the principal axis. |

Training the RZ Linear Regression Engine

| | |
|---|---|
| Input: | The r coordinates obtained from the PCA Regression, the corresponding z values, and the Z focus point $z_F$. |
| Output: | The Linear Regression Coefficients relating $(z - z_F)$ to r. |
| Description: | Perform Linear Regression Analysis and save the coefficients. |

Training the Outlier Detector

An outlier detection scheme is used to warn the presence of a bubble or to flag a filter wheel problem.

| | |
|---|---|
| Input: | The q coordinates obtained from the PCA Regression, along with the spot features for every spot in the calibration sequence are used to train a classifier to detect outlier spots. |
| Output: | Internal settings of the Outlier Detector. |
| Description: | For every feature $\phi$, the mean $\mu_\phi$ and standard deviation $\sigma_\phi$ is calculated from the spots used during calibration. The general idea is that a spot would be declared an outlier spot if the feature $\phi$ is outside the bounds of $\mu_\phi \pm 3\sigma_\phi$. However in the current implementation only the Volume and Area features are used in this way—in fact, only the upper bounds are currently used for these two features. Special bounds are set to override these values for both the picture quality and the q residue feature. For the picture quality, a lower bound is used. For the residue, an upper bound is used. |

Running the Autofocus System

A run starts from an image of the autofocus laser spot and uses the coefficients of the transformations learned during the calibration process to make the best estimate for the z displacement required to move to focus.

| | |
|---|---|
| Input: | An image of the autofocus laser spot. |
| Output: | $(z - z_F)$ to move to focus. Also provides recommendation of whether or not to move based upon outlier detection. |
| Description: | Derives best estimate of $(z - z_F)$ using: 1. The spot extraction algorithm. 2. The PCA based XY Regression coefficients. 3. The Linear RZ Regression coefficients. In one implementation, the outlier detection scheme allows a move only in the case of a large q residual. In case of low picture quality, high volume, or high area, it recommends non-movement. If during long periods of z non-movement, as may be triggered by large bubbles/contaminations in the flowcell. the surface of the flowcell drifts enough to make the secondary spot appear locally in all respects to the primary spot seen in calibration, such algorithm would latch onto such spot for the rest of the cycle even though the bubble/contamination ceased to exist inside the flowcell. In order to recover from such problem, the following steps can be taken: In case a move is recommended, a further check can be performed to see whether a secondary spot exists in the direction opposite to the one where training says it ought to be. If it does, then a move can be recommended to this spot using the PCA based XY Regression and the Linear RZ Regression coefficients. |

Computer

As noted above, the various components of the present system are coupled to an appropriately programmed processor or computer that functions to instruct the operation of these instruments in accordance with preprogrammed or user input instructions, receive data and information from these instruments, and interpret, manipulate and report this information to the user. As such, the computer is typically appropriately coupled to these instruments/components (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations (e.g., auto focusing, SBS sequencing, etc.). The software then converts these instructions to appropriate language for instructing the correct operation to carry out the desired operation (e.g., of fluid direction and transport, autofocusing, etc.).

For example, the computer is optionally used to direct a fluid flow component to control fluid flow, e.g., through a variety of tubing. The fluid flow component optionally directs the movement of the appropriate buffers, nucleotides, enzymes, etc., into and through the flowcell.

The computer also optionally receives the data from the one or more sensors/detectors included within the system, and interprets the data, either provides it in a user understood format, or uses that data to initiate further controller instructions, in accordance with the programming, e.g., such as in monitoring and control of flow rates, temperatures, and the like.

In the present invention, the computer typically includes software for the monitoring and control of materials in the flowcells. Additionally the software is optionally used to control excitation of the fluorescent labels and monitoring of the resulting emissions. The computer also typically provides instructions, e.g., to the heating/cooling component and autofocus system, etc.

Any controller or computer optionally includes a monitor, which is often a cathode ray tube ("CRT") display, a flat panel display (e.g., active matrix liquid crystal display, liquid crystal display), or the like. Data produced from the current systems. e.g., nucleic acid sequence results is optionally displayed in electronic form on the monitor. Additionally, the data, e.g., light emission profiles from the nucleic acid arrays, or other data, gathered from the system can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

Exemplary Use and Component Variation

The SBS systems herein, in many embodiments, comprise CCD/TIRF laser based excitation and imaging subsystems which can image millions of nucleic acid clusters per sample (typically within a flowcell) and which can detect each of four fluorescent dyes (one for each of the four bases). The SBS chemistry components, e.g., nucleotides. WO04018497, WO04018493 and U.S. Pat. No. 7,057,026, polymerases WO05024010 and WO06120433, surface attachment techniques. WO05065814, cluster preparation and sequencing, WO 9844151, WO06064199 and WO07010251, are compatible with the channeled flowcell components herein, etc. The computer or data analysis system aspects of the system are optionally capable of processing thousands of images per hour into sequence information As an overview, in particular examples of sequencing by SBS, genomic DNA is randomly fragmented, end capped with known sequences, and covalently attached to a substrate (such as the channel in a flowcell), e.g., by hybridization to a covalent primer. From such attached DNA, an array of nucleic acid clusters is created, as described in WO9844141 and WO07010251. SBS analysis (e.g., using the systems and devices herein) can generate a series of images of the clusters, which can then be processed to read the sequence of the nucleic acids in each cluster which can then be aligned against a reference sequence to determine sequence differences, a larger overall sequence, or the like. Algorithms for the alignment of short reads of nucleic acids are described in WO05068089.

Figure 30:
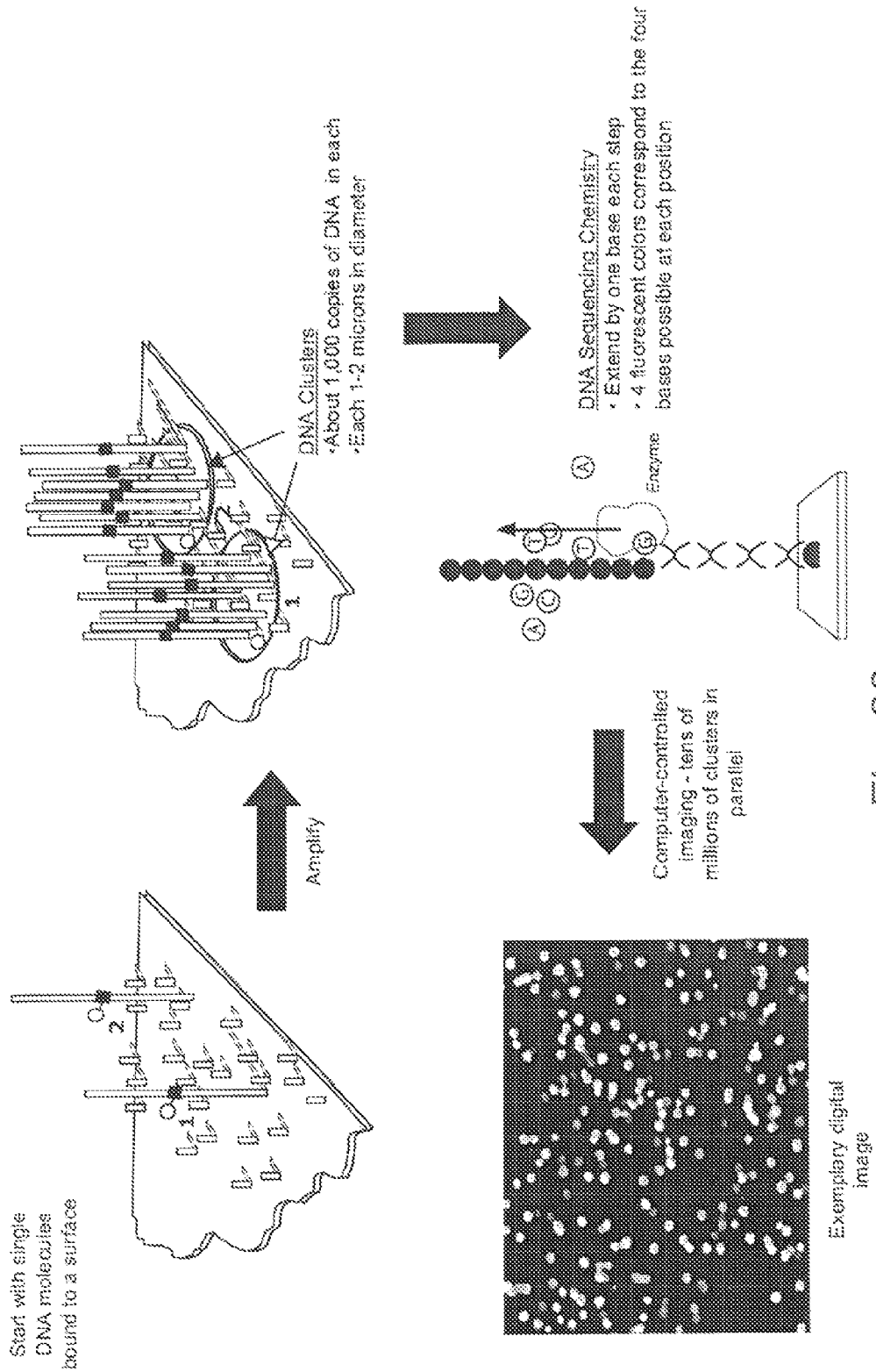
Figure 32:
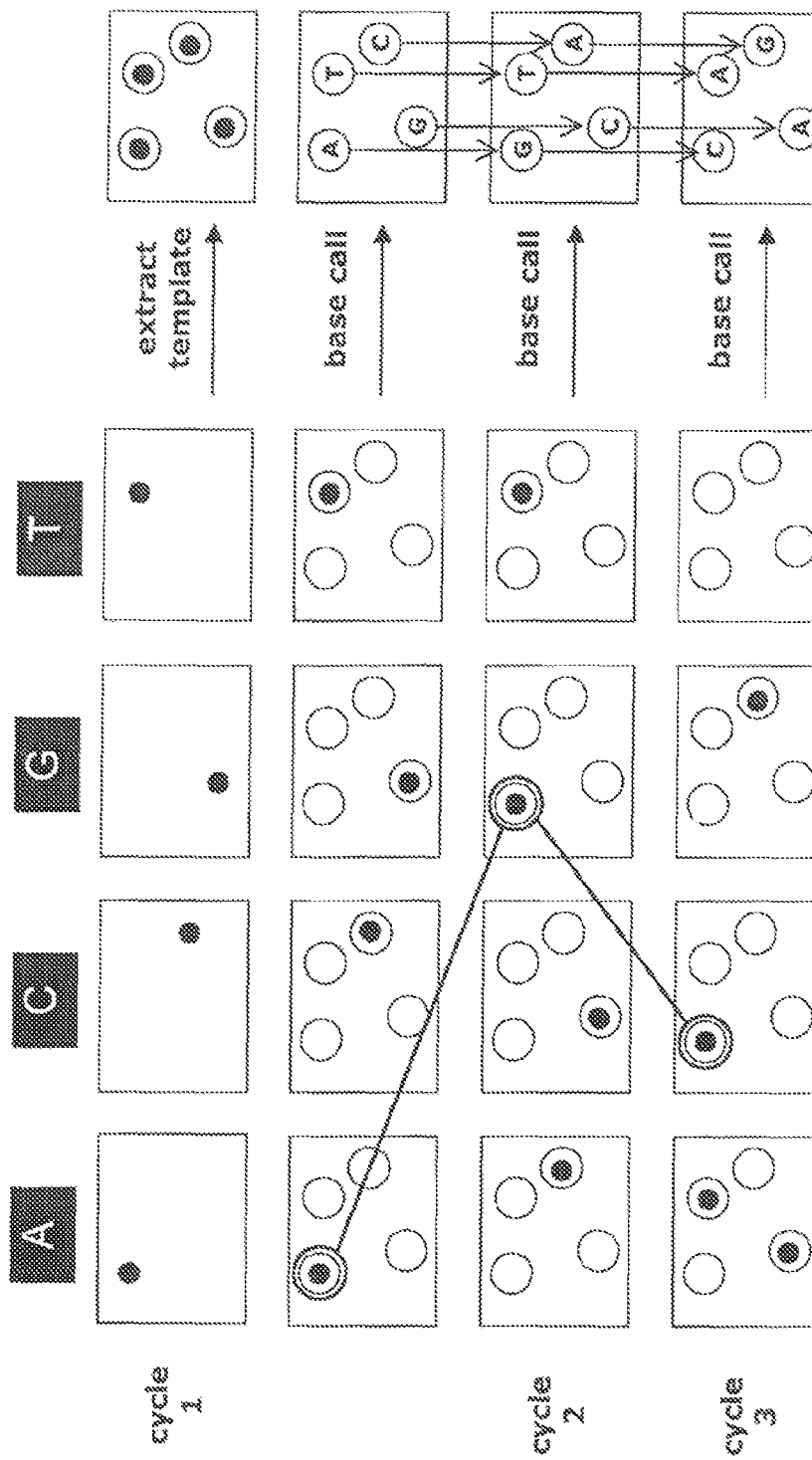
Figure 33B:
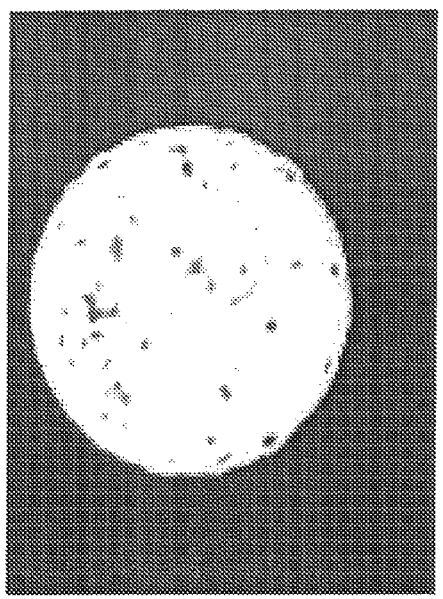
FIG. 33, Panels A-D show the effects of three different forms of physical deformation to a circular optical fiber on the beam emerging from the fiber. Vibrating or squeezing the fiber makes the light emerging from the fiber uniform over the integration time of the image.
Figure 33D:
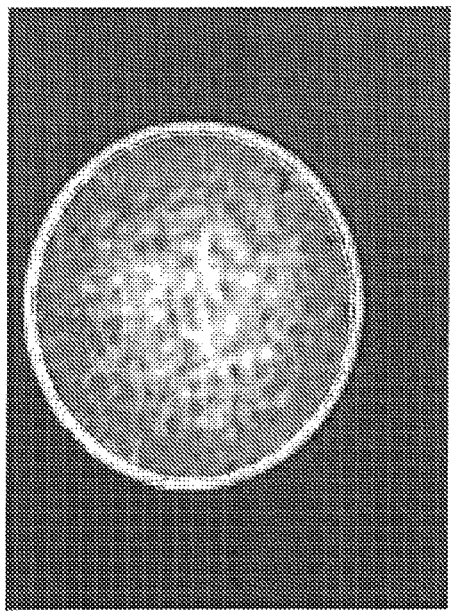
Figure 33A:
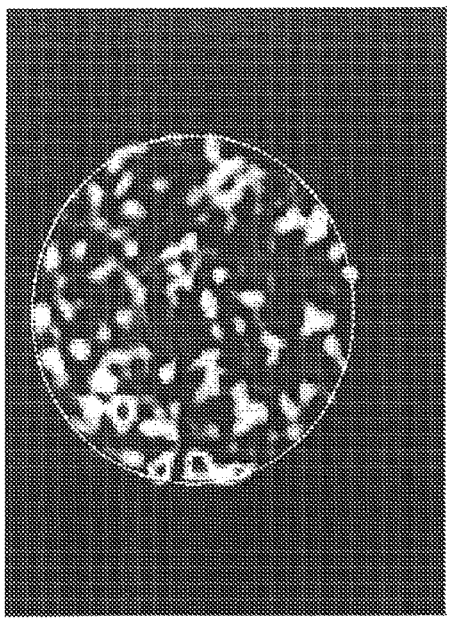
Figure 33C:
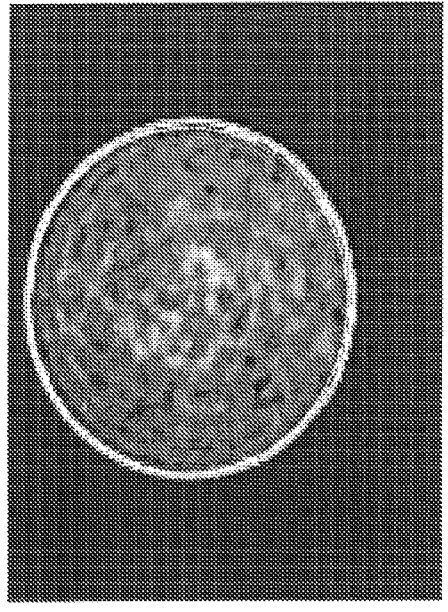
Figure 34B:
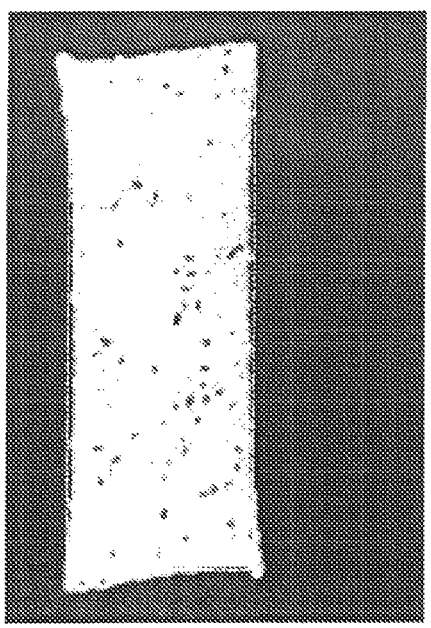
FIG. 34, Panels A-D show the effects of three different forms of physical deformation to a rectangular optical fiber on the beam emerging from the fiber. Vibrating or squeezing the fiber makes the light emerging from the fiber uniform over the integration time of the image.
Figure 34D:
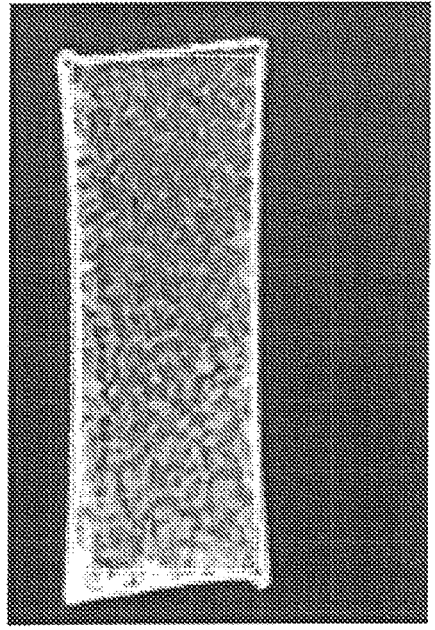
Figure 34A:
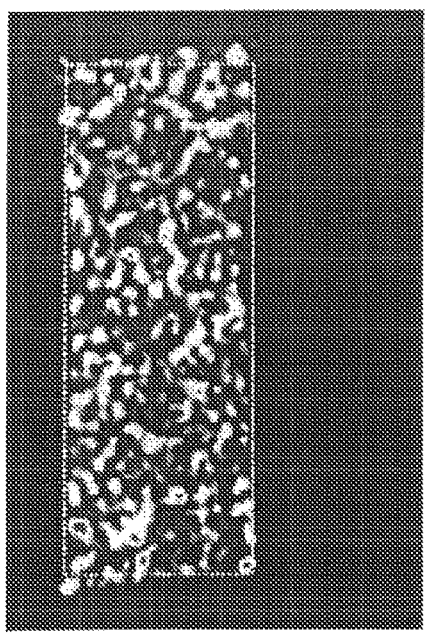
Figure 34C:
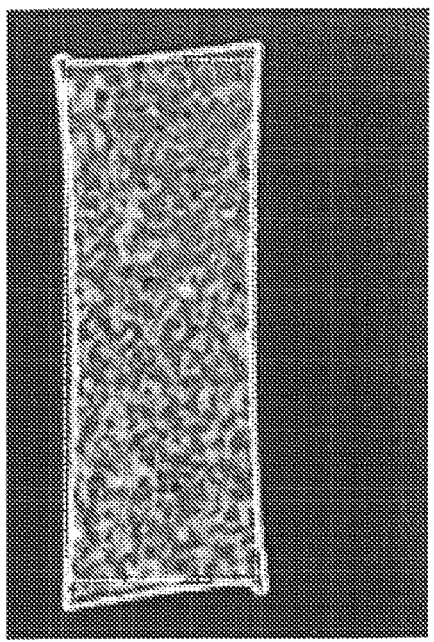

As described above, each sequencing cycle will include a round of incorporation onto the growing nucleic acid chain. Such cycle is typically done by an addition of all four dNTPs, each modified so that each base is identifiable by a unique fluorophore. Additionally, the triphosphates are modified at the 3' position so that extension is controlled and not more than a single base can be added to each molecule in each cycle. The generic concept of performing clusters amplified from a single template molecule on a random array, and the subsequent sequencing of said array is shown in FIGS. 30-32, which schematically illustrate various aspects of sequencing procedures and methods carried out by the systems herein. For example, the basic overview steps of formation of nucleic acid clusters, the cluster arrays produced (and a comparison of such cluster arrays against a more "traditional" array) and an outline of the sequencing methodology are all presented. FIG. 30 shows the basic outlines of nucleic acid cluster creation and sequencing while FIG. 31 compares nucleic acid density between an array (on left) and on a nucleic acid cluster substrate such as those capable of use with the systems/devices of the invention (on right). FIG. 32 gives a cartoon outlining the SBS sequencing procedure, e.g., as done by embodiments of the invention.

After the incorporation step wherein a fluorescently labeled nucleotide is bound to the nucleic acid of the members of the clusters through a cleavable linker, the channels of the flowcell are washed out by the fluid flow subsystem in order to remove any unincorporated nucleosides and enzyme.

Next, a read step is performed by the system, whereby the identity of the individual labels (read as a group in each cluster) incorporated in the incorporation step is recorded using optical microscopy and the corresponding base incorporated is noted. The sequencing system can read the four different fluorophores using two lasers at distinct wavelengths via total internal reflection microscopy (TIRF) and four distinct emission filters at different parts of the spectrum. The images are recorded onto a CCD camera and reported into the attached computer module.

After the specific incorporation is read, a deprotection step removes the labeling moiety and block from the surface bound DNA. The deprotection allows repetition of the above incorporation and reading steps until sufficient cycles of information are obtained to uniquely place the sequence of each nucleic acid cluster (present on the flowcell) in its genomic context. For example, in the case of the human genome this will be >16 cycles, e.g., about 25-50 cycles. The images can be stored off line, or processed in real time such that the individual bases are read during the sequencing process. Processing the images provides a database of a sequence read from every cluster, where each cluster is derived from a random position somewhere in entire sample (e.g., a genome). Thus during the course of the procedure, a database of millions of sequence reads covering every part of the genome is typically constructed. Such database can be, e.g., compared with a database of every sequence derived from a reference sequence, etc. In various embodiments, image analysis, sequence determination, and/or sequence alignment are optionally performed "off-line" after the fluorescent images are captured. Such procedures are also optionally performed by a computer separate from the one present in the current systems.

As mentioned throughout, the current invention can vary between embodiments (e.g., in number and type of components or subsystems). For example, in one embodiment of the invention (embodiment "b"), the components can comprise: illumination lasers (used to excite the fluorophores in the sequencing reactions) of 532 and 660 nm each with 75 mW power (or optionally greater) that project as 0.5 mm circle on the bottom of the channel in a flowcell; a TIR prism of glass (68 deg or 71 deg); a glass flowcell with channels of 1×61 mm area having 8 channels that are 100 μm deep (39×1 mm usable or accessible for viewing); an objective lens in the camera component comprising a Nikon Plan Apo 20×, 0.75NA (corrected for glass thickness); emission filters comprising Bandpass filters of 557±11 nm, 615±40 nm. 684±11 nm, and 740±50 nm (or optionally filters as shown, or similar to those shown, in FIG. 22); relay optics comprising a Navitar 1.33× adapter for a net magnification of about 23×, or an unmagnified tube lens; and a digital CCD camera comprising a Photometrics Cascade 1 Mpix or 1K camera, with a pixel size of 8 μm, and a readout rate of 10 MHz, and a microscope objective of 20× magnification with 0.75 NA (numerical aperture). The Cascade embodiment "b" can give a net performance of 0.35 mm field with approximately 0.8 μm optical resolution (somewhat larger than diffraction limit).

Such 1 Megapixel embodiments can illuminate a 0.5 mm circle and detect a 0.35 mm square inside it. The flowcell in such embodiments can have a total of 156 non-overlapping tiles in a channel or higher. The clusters can be on the order of 1 μm. The NA of the microscope can optionally give a PSF of approximately 0.6 μm at 700 nm. Thus, a "typical" cluster gets an apparent diameter of approximately 1.2 μm. In the image plane, 1 pixel represents approximately 0.35 μm, so a typical cluster would have about 3.5 pixels diameter. The area of a cluster is the about 9.25 pixels. Poisson distribution of 10 area pixel objects on 1 Mpixel CCD shows maximum of about 38,000 objects will be non-overlapping as shown in FIG. 29. FIG. 29 gives an example of information throughput from an exemplary configuration of a system of the invention. The number of detected clusters is a function of the total cluster number and the minimum cluster area.

For exemplary "b" embodiments, the resolution limit (using Rayleigh criterion) is about 0.6 μm and clusters are about 1 μm for an apparent size of about 1.2 μm. Pixels map to about 0.35 μm in image plane so a cluster is about 3.5 pixels across and about 10 pixels in area. For randomly distributed clusters, the maximum number of unconfused clusters in the 1 MPix camera will be about 38,000 in a 0.35 mm square tile. "b" flowcells accommodate 150 non-overlapping illumination tiles per channel for a total of 1200 tiles per flowcell. This is 45.6 M Bases per cycle and about 1 GBase in a 25 cycle run.

Overlapping the illumination and closely packing the tiles means that 200 tiles can be imaged per channel, and therefore 1600 per flowcell.

For the "b" illumination subsystem throughput, the laser wavelengths are: green laser wavelength 532 nm; green laser power optionally 75 mW; red laser wavelength 660 nm; red laser power optionally 75 mW; projected TIRF beam diameter 0.5 mm; and allowed variation across beam 20%.

In another embodiment, (embodiment "g"), the system of the invention can comprise: illumination lasers of 532 and 660 nm, each with 500 mW power (ideally projected as 0.5 mm square), a TIR prism of glass (68 deg); a glass flowcell having 8 channels 100 µm deep and of 1×61 mm in area with a 50 mm usable; an objective lens comprising a Nikon Plan Fluor 40×, 0.6 NA adjustable collar, or custom 40×, 0.75 NA corrected for an SBS flowcell; emission filters comprising Bandpass filters of 557±11 nm, 615±40 nm, 684±11 nm, and 740±50 nm; image optics comprising an 150 mm achromatic doublet for system magnification of 30×; and a digital CCD camera comprising a Photometrics CoolSNAP K4, 2048 by 2048 pixels, 4 Mpix camera, 7.4 µm pixel size, 20 MHz readout. Such embodiment can give a net performance of 0.5 mm field with less than 0.7 µm diffraction limit. It can comprise a relay lens of 0.75× for total 30× system magnification.

In some such "g" embodiments, it is desired that a 0.5 mm square is uniformly illuminated and that the same 0.5 mm square is detected (2048×7.4/30000). The clusters on the flowcells herein can be as small as 0.5 µm. PSF at 700 nm is approximately 0.7 µm. Clusters thus appear as 0.86 µm where 1 pixel represents 0.25 µm. A typical cluster therefore is 3.5 pixels and the area of a cluster is 9.25 pixels. 4 Mpixel CCD gives a maximum of about 135,000 detectable non-overlapping clusters per tile.

The illumination footprint is four times larger, meaning a 4 time increase in laser powers is needed to obtain the same level of signal in the same exposure time. To minimize exposure times, the laser power can be increased further. Such a system is therefore capable of generating 2 billion bases of sequence per experiment, if the following parameters are used: Objective with numerical aperture 0.8; 20× magnification; 4 Mpixel camera; 760 µm×760 µm illumination tiles; 1 imaging lane per flow channel; 48 tiles per lane; 8 channels per chip; clusters of average size 0.7 µm; and, read length of 40 bases. Therefore total throughput=8 channels×48 tiles× 135000 clusters/tile×40 cycles=2.07 billion bases (G).

Figure 43:
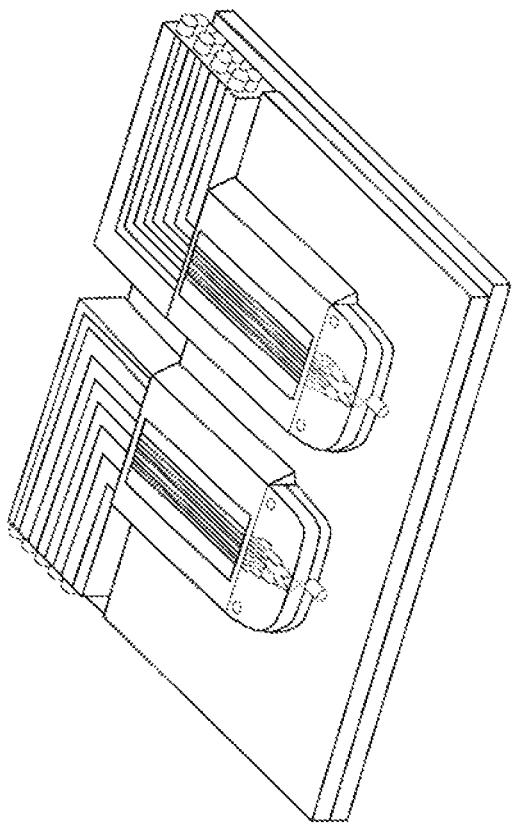
FIG. 43 shows a dual flowcell holder embodiment of the invention such that chemistry operations can be performed in parallel in order to maximize the scanning time of the instrument.

Increasing the size of the flowcell to increase the numbers of tiles imaged, the density of clusters, or the read length, will enable improvements in the number of bases generated per flowcell. Two or four cameras can be mounted in parallel to obtain a system with two or four times the throughput. A two camera configuration is shown in FIGS. 36 and 37. The scanning time can be decreased using techniques such as Time Delay Integration (TDI), meaning that the surface is continually scanned rather than imaged in discrete tiles. The instrument can be configured to perform multiple chemistry steps with multiple fluidics systems coupled to a single optical system. In the single chemistry system, the optical system is not imaging whilst the chemistry steps are occurring. If the chemistry and imaging parts of the cycle take similar lengths, then for 50% of the time, the instrument is not recording data. If the scanning part of the system is further speeded up, then an even higher percentage of the experimental run time is spent performing chemistry. This can be alleviated if the system is configured such that multiple flowcells are processed simultaneously, with one flowcell always undergoing imaging. Schematic representations of a dual flowcell holder are shown in FIG. 43.

Although the system as described is shown with the illumination from underneath, and the objective on top, the system as shown can be inverted to illuminate from the top, and have the detection system underneath. See above. The heating and illumination can be carried out from either face of the substrate, so that bottom side heating and top side illumination are also within the scope of the invention. The operation of systems within the scope of the inventions are further described in the following general methods.

Examples of Using the System in Sequencing

The following are examples of general techniques and the like (e.g., for nucleic acid cluster formation) which can optionally be applied in use with the systems of the invention. It will be appreciated that such descriptions and examples are not necessarily limiting upon the current systems and their use unless specifically stated to be so. The methods for forming and sequencing nucleic acid clusters are fully described in patent application WO07010251, the protocols of which are incorporated herein by reference in their entirety, but some elements of these protocols are summarized below.

Preparation of Substrates and Formation of Nucleic Acid Clusters

Acrylamide Coating of Glass Chips

The solid supports used for attachment of nucleic acid to be sequenced are optionally 8-channel glass chips such as those provided by Silex Microsystems (Sweden). However, the experimental conditions and procedures are readily applicable to other solid supports as well. In some embodiments chips were washed as follows: neat Decon for 30 min, milliQ H2O for 30 min, NaOH 1N for 15 min, milliQ H2O for 30 min, HCl 0.1N for 15 min, milliQ H2O for 30 min. The Polymer solution preparation entailed:

For 10 ml of 2% polymerization mix.

10 ml of 2% solution of acrylamide in milliQ H2O;

165 µl of a 100 mg/ml N-(5-bromoacetamidylpentyl)acrylamide (BRAPA) solution in DMF (23.5 mg in 235 µl DMF);

11.5 µl of TEMED; and,

100 µl of a 50 mg/ml solution of potassium persulfate in milliQ H2O (20 mg in 400 µl H2O).

In such embodiments, the 10 ml solution of acrylamide was first degassed with argon for 15 min. The solutions of BRAPA, TEMED and potassium persulfate were successively added to the acrylamide solution. The mixture was then quickly vortexed and immediately used. Polymerization was then carried out for 1 h 30 at RT. Afterwards the channels were washed with milliQ H2O for 30 min and filled with 0.1 M potassium phosphate buffer for storage until required.

Synthesis of
N-(5-bromoacetamidylpentyl)acrylamide (BRAPA)

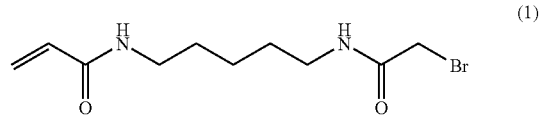
(1)

N-Boc-1,5-diaminopentane toluene sulfonic acid was obtained from Novabiochem. The bromoacetyl chloride and acryloyl chloride were obtained from Fluka. All other reagents were Aldrich products.

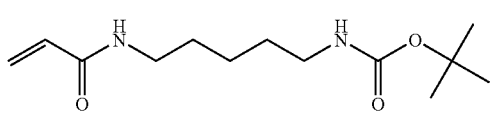

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml. 1 eq) through a pressure equalized dropping funnel over a one hour period. The reaction mixture was then stirred at room temperature and the progress of the reaction checked by TLC (petroleum ether:ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. 1H NMR (400 MHz, d6-DMSO): 1.20-1.22 (m, 2H, CH2), 1.29-1.43 (m, 13H, tBu, 2×CH2), 2.86 (q, 2H, J=6.8 Hz and 12.9 Hz, CH2), 3.07 (q, 2H, J=6.8 Hz and 12.9 Hz, CH2), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for C13H24N2O3 256, found 279 (256+Na+).

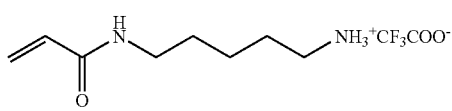

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). 1H NMR (400 MHz, D2O): 1.29-1.40 (m, 2H, CH2), 1.52 (quint., 2H, J=7.1 Hz, CH2), 1.61 (quint., 2H, J=7.7 Hz, CH2), 2.92 (t, 2H, J=7.6 Hz, CH2), 3.21 (t, 2H, J=6.8 Hz, CH2), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for C8H16N2O 156, found 179 (156+Na+).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at mom temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. 1H NMR (400 MHz, d6-DMSO): 1.21-1.30 (m, 2H, CH2), 1.34-1.48 (m, 4H, 2×CH2), 3.02-3.12 (m, 4H, 2×CH2), 3.81 (s, 2H, CH2), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for C10H17BrN2O2 276 or 278, found 279 (278+H+), 299 (276+Na+).

The Cluster Formation Process

Fluidics

For all fluidic steps during the cluster formation process, a peristaltic pump Ismatec IPC equipped with tubing Ismatec Ref 070534-051 (orange/yellow, 0.51 mm internal diameter) is optionally used. The pump is run in the forward direction (pulling fluids). A waste dish is installed to collect used solution at the outlet of the peristaltic pump tubing. During each step of the process, the different solutions used are dispensed into 8 tube microtube strips, using 1 tube per chip inlet tubing, in order to monitor the correct pumping of the solutions in each channel. The volume required per channel is specified for each step.

Thermal Control

To enable incubation at different temperatures during the cluster formation process, the Silex chip is mounted on top of an MJ-Research thermocycler. The chip sits on top of a custom made copper block, which is attached to the flat heating block of the thermocycler. The chip is covered with a small Perspex block and is held in place by adhesive tape. Both pump and thermocycler are controlled by computer run scripts, which prompt the user to change solutions between each step.

Grafting Primers Onto Surface of SFA Coated Chip

An SFA coated chip is placed onto a modified MJ-Research thermocycler and attached to a peristaltic pump as described above. Grafting mix consisting of 0.5 μM of a forward primer and 0.5 μM of a reverse primer in 10 mM phosphate buffer (pH 7.0) is pumped into the channels of the chip at a flow rate of 60 μl/min for 75 s at 20° C. The thermocycler is then heated up to 51.6° C., and the chip is incubated at this temperature for 1 hour. During this time, the grafting mix undergoes 18 cycles of pumping: grafting mix is pumped in at 15 μl/min for 20 s, then the solution is pumped back and forth (5 s forward at 15 μl/min, then 5 s backward at 15 μl/min) for 180 s. After 18 cycles of pumping, the chip is washed by pumping in 5×SSC/5 mM EDTA at 15 μl/min for 300 s at 51.6° C. The thermocycler is then cooled to 20° C.

Template DNA Hybridization

The DNA templates to be hybridized to the grafted chip are diluted to the required concentration (currently 0.5-2 pM) in 5×SSC/0.1% Tween. The diluted DNA is heated on a heating block at 100° C. for 5 min to denature the double stranded DNA into single strands suitable for hybridization. The DNA is then immediately snap-chilled in an ice/water bath for 3 min. The tubes containing the DNA are briefly spun in a centrifuge to collect any condensation, and then transferred to a pre-chilled 8-tube strip and used immediately.

The grafted chip from above is primed by pumping in 5×SSC/0.1% Tween at 60 μl/min for 75 s at 20° C. The thermocycler is then heated to 98.5° C., and the denatured DNA is pumped in at 15 μl/min for 300 s. An additional pump at 100 μl/min for 10 s is carried out to flush through bubbles formed by the heating of the hybridization mix. The temperature is then held at 98.5° C. for 30 s, before being cooled slowly to 40.2° C. over 19.5 min. The chip is then washed by pumping in 0.3×SSC/0.1% Tween at 15 μl/min for 300 s at 40.2° C. The script then runs straight to the next step.

Amplification

The hybridized template molecules are amplified by a bridging polymerase chain reaction using the grafted primers and a thermostable polymerase. Amplification buffer consisting of 10 mM Tris (pH 9.0), 50 mM KCl, 1.5 mM MgCl2, 1 M betaine and 1.3% DMSO is pumped into the chip at 15 µl/min for 200 s at 40.2° C. Then amplification mix of the above buffer supplemented with 200 µM dNTPs and 25 U/ml Taq polymerase is pumped in at 60 µl/min for 75 s at 40.2° C. The thermocycler is then heated to 74° C. and held at this temperature for 90 s. This step enables extension of the surface bound primers to which the DNA template strands are hybridized. The thermocycler then carries out 50 cycles of amplification by heating to 98.5° C. for 45 s (denaturation of bridged strands), 58° C. for 90 s (annealing of strands to surface primers) and 74° C. for 90 s (primer extension). At the end of each incubation at 98.5° C., fresh PCR mix is pumped into the channels of the chip at 15 µl/min for 10 s. As well as providing fresh reagents for each cycle of the PCR, this step also removes DNA strands and primers which have become detached from the surface and which could lead to contamination between clusters. At the end of thermocycling, the chip is cooled to 20° C. The chip is then washed by pumping in 0.3×SSC/0.1% Tween at 15 µl/min for 300 s at 74° C. The thermocycler is then cooled to 20° C.

Linearization

Linearization mix consisting of 0.1 M sodium periodate and 0.1 M ethanolamine is pumped into the chip at 15 µl/min for 1 hr at 20° C. The chip is then washed by pumping in water at 15 µl/min for 300 s at 20° C.

Blocking (Optional)

This step uses Terminal Transferase to incorporate a dideoxynucleotide onto the free 3' OH ends of DNA strands (both grafted primers and amplified cluster molecules).

Blocking buffer consisting of 50 mM potassium acetate, 20 mM Tris-acetate, 10 mM magnesium acetate, 1 mM dithiothreitol (pH 7.9) and 250 µM CoCl2 is pumped into the chip at 15 µl/min for 200 s at 20° C. Then Blocking Mix of the above buffer supplemented with 2.4 µM ddNTPs and 250 U/ml Terminal transferase is pumped in at 15 µl/min for 300 s at 37.7° C. The thermocycler is held at 37.7° C. for 30 min, during which time Blocking Mix is pumped into the chip at 15 µl/min for 20 s every 3 min. After blocking, the chip is then washed by pumping in 0.3×SSC/0.1% Tween at 15 µl/min for 300 s at 20° C.

Denaturation of Clusters and Hybridization of Sequencing Primer

This step uses NaOH to denature and wash away one of the strands of the amplified, linearized and blocked clusters. After a wash to remove the NaOH, the sequencing primer is then hybridized onto the single strands left on the surface.

After blocking, the double stranded DNA in the clusters is denatured by pumping in 0.1N NaOH at 15 µl/min for 300 s at 20° C. The chip is then washed by pumping in TE (10 mM Tris pH 8.0, 1 mM EDTA) at 15 µl/min for 300 s at 20° C. Sequencing primer is diluted to 0.5 µM in 5×SSC/0.1% Tween, and pumped into the channels at 15 µl/min for 300 s at 20° C. The thermocycler is then heated up to 60° C. and held at this temperature for 15 min. The thermocycler is then cooled to 40.2° C. and the chip is washed by pumping in 0.3×SSC/0.1% Tween at 15 µl/min for 300 s.

The clusters are now ready for 1st cycle sequencing enzymology, e.g., with the systems and devices of the current invention.

The DNA sequence used in this process was a single monotemplate sequence of 400 bases, with ends complimentary to the grafted primers. The duplex DNA was denatured as described above.

Grafting of Primers

The primers are typically 5'-phosphomthioate oligonucleotides incorporating any specific sequences or modifications required for cleavage. Their sequences and suppliers vary according to the experiment they are to be used for, and in this case were complementary to the 5'-ends of the template duplex.

Sequencing of Linearized Clusters

The amplified clusters contained a diol linkage in one of the grafted primers. Diol linkages can be introduced by including a suitable linkage into one of the primers used for solid-phase amplification.

Suitable primers including any desired template-specific sequence can be manufactured by standard automated DNA synthesis techniques using components available from commercial suppliers (e.g. Fidelity Systems Inc., ATD).

A cleavable diol-containing primer would typically have the following structure:

5'-phosphorothioate-arm 26-diol22A-sequence-3'OH.

Wherein "sequence" represents a sequence of nucleotides capable of hybridizing to the template to be amplified.

The structures of the arm26 and diol22A components (from Fidelity Systems Inc, MD, USA) are as follows:

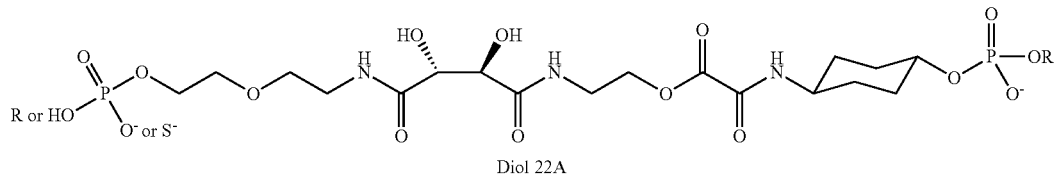

Diol 22A

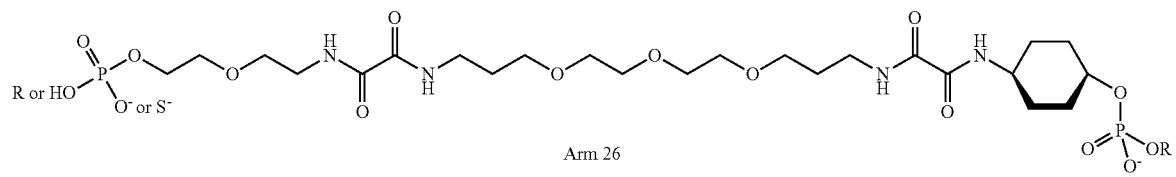

Arm 26

Products containing such diol linkages can be cleaved using periodate as described above, and the resulting single stranded polynucleotides hybridized as described above.

DNA Sequencing Cycles

Sequencing was carried out using modified nucleotides prepared as described in International patent application WO 2004/018493, and labeled with four different commercially available fluorophores (Molecular Probes. Inc.).

A mutant 9°N polymerase enzyme (an exo-variant including the triple mutation L408Y/Y409A/P410V and C223S) was used for the nucleotide incorporation steps.

Incorporation mix, Incorporation buffer (50 mM Tris-HCl pH 8.0, 6 mM MgSO4, 1 mM EDTA, 0.05% (v/v) Tween-20, 50 mM NaCl) plus 110 nM YAV exo-C223S, and 1 µM each of the four labeled modified nucleotides, was applied to the clustered templates, and heated to 45° C.

Templates were maintained at 45° C. for 30 min, cooled to 20° C. and washed with Incorporation buffer, then with 5×SSC/0.05% Tween 20. Templates were then exposed to Imaging buffer (100 mM Tris pH7.0, 30 mM NaCl, 0.05% Tween 20, 50 mM sodium ascorbate, freshly dissolved).

Templates were scanned in 4 colors at RT.

Templates were then exposed to sequencing cycles of Cleavage and Incorporation as follows:

Cleavage

Prime with Cleavage buffer (0.1M Tris pH 7.4, 0.1 M NaCl and 0.05% Tween 20). Heat to 60° C.

Treat the clusters with Cleavage mix (100 mM TCEP in Cleavage buffer).

Wait for a total of 15 min in addition to pumping fresh buffer every 4 min.

Cool to 20° C.

Wash with Enzymology buffer.

Wash with 5×SSC/0.05% Tween 20.

Prime with Imaging buffer.

Scan in 4 colors at RT.

Incorporation

Prime with Incorporation buffer Heat to 60° C.

Treat with Incorporation mix. Wait for a total of 15 min in addition to pumping fresh Incorporation mix every 4 min.

Cool to 20° C.

Wash with Incorporation buffer.

Wash with 5×SSC/0.05% Tween 20.

Prime with imaging buffer.

Scan in 4 colors at RT.

Repeat the process of Incorporation and Cleavage for as many cycles as required. Incorporated nucleotides were detected using the fluorescent imaging apparatus described above.

Alternatively, the flowcell can be sequenced in a fully automated way, with the first incorporation being performed on this instrument, as described below:

After setting the flowcell on the instrument manifold, the templates can be exposed to the sequencing cycles described below: first base incorporation, imaging then alternating cleavage, imaging and incorporation, imaging steps for as many sequencing cycles as required.

First Base Incorporation

Pump 1000 ul of incorporation buffer at RT
Set temperature at 55° C. and hold
Wait for 2 minutes
Pump 600 ul of incorporation mix
Wait for 4 minutes
Pump 200 ul of incorporation mix
Wait for 4 minutes
Pump 200 ul of incorporation mix
Wait for 4 minutes
Set temperature at 22° C.
Wait for 2 minutes
Pump 600 ul of incorporation buffer
Pump 600 ul of high salt buffer
Pump 800 ul of scanning mix
Stop active cooling
Imaging Step
  Cleavage
Pump 1000 ul of cleavage buffer at RT
Set temperature at 55° C. and hold
Wait for 2 minutes
Pump 600 ul of cleavage mix
Wait for 4 minutes
Pump 200 ul of cleavage mix
Wait for 4 minutes
Pump 200 ul of cleavage mix
Wait for 4 minutes
Set temperature at 22° C. and hold
Wait for 2 minutes
Pump 600 ul of incorporation buffer
Pump 600 ul of high salt buffer
Pump 800 ul of scanning mix
Stop active cooling
Imaging Step
  Incorporation
Pump 1000 ul of incorporation buffer at RT
Set temperature at 55° C. and hold
Wait for 2 minutes
Pump 600 ul of incorporation mix
Wait for 4 minutes
Pump 200 ul of incorporation mix
Wait for 4 minutes
Pump 200 ul of incorporation mix
Wait for 4 minutes
Set temperature at 22° C. and hold
Wait for 2 minutes
Pump 600 ul of incorporation buffer
Pump 600 ul of high salt buffer
Pump 800 ul of scanning mix
Stop active cooling.

Each tile of each the chip for the non-fully automated process above was recorded in each of the four colors corresponding to the labeled nucleotides. The images were analyzed to pick the brightest color for each cluster, and this image intensity analysis was used to call the base for each cluster at each cycle. Images from each cycle were co-localized to obtain the sequence corresponding to each cluster. As the sequence of each cluster was known; and was the same for every cluster in the above experiment, the error rates (i.e. clusters not called as the correct sequence) could be analyzed for each cycle of nucleotide incorporation. The error rates were less than 1% for the first 20 cycles of the experiment, meaning the known sequence of the monotemplate was correctly called.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A system for detecting fluorescence emitted from nucleic acids, wherein the nucleic acids comprise fluorescent labels, the system comprising:
   a) a stage configured to hold a solid substrate having the nucleic acids;
   b) a fluid direction system for controllably moving one or more reagents into contact with the nucleic acids;
   c) an illumination system for exciting the fluorescent labels via total internal reflection (TIR), the illumination system comprising a mode scrambler and a multimode optical fiber that provides a fluorescent-excitation illumination beam having multiple propagating modes, the mode scrambler scrambling the modes of the illumination beam to provide a substantially uniform illumination footprint to excite the fluorescent labels, wherein the illumination beam is directed to be incident on the solid substrate so that the footprint excites the fluorescent labels through TIR; and
   d) a detector component for detecting fluorescence produced from excitation of the fluorescent labels by the footprint.

2. The system of claim 1, further comprising the solid substrate, the solid substrate comprising a flowcell having at least one fluidic channel.

3. The system of claim 2, wherein the flowcell comprises a channel layer and a cover layer that is overlaid upon the channel layer, the channel layer including the fluidic channel, the cover layer having a through-hole that provides access to the fluidic channel.

4. The system of claim 2, wherein the fluidic channel has one or more inlet ports at a first end of the channel and one or more outlet ports at a second end of the channel, the inlet and outlet ports being located with respect to each other to facilitate maintaining a uniform flow of a liquid through the fluidic channel.

5. The system of claim 2 wherein the fluid direction system comprises a pump placed after the flowcell to pull reagents through the flowcell.

6. The system according to claim 1, further comprising the solid substrate, the solid substrate comprising an array of beads.

7. The system of claim 1, further comprising the nucleic acids and the reagents, the nucleic acids including polynucleotides, the reagents comprising components to extend a second sequence complementary to the one or more polynucleotides.

8. The system according to claim 7, wherein said reagents are fluorescently labeled nucleoside triphosphates.

9. The system according to claim 7, wherein said reagents are fluorescently labeled oligonucleotides.

10. The system of claim 7, wherein the reagents include four different reagents having respective fluorescent labels, the detector component further comprising four optic filters appropriate for filtering emissions of the four fluorescently labeled reagents and light from the illumination beam.

11. The system of claim 1, wherein the illumination system comprises at least one excitation laser coupled through the multimode fiber.

12. The system according to claim 11, further comprising a computer component that is operably coupled to the mode scrambler, the computer component controlling the mode scrambler to physically engage the multimode fiber to change an index of refraction of the multimode fiber a plurality of times to scramble the modes.

13. The system according to claim 12, wherein the computer component controls the mode scrambler to squeeze or compress the multimode fiber.

14. A system according to claim 13, wherein the computer component controls the mode scrambler to change an intensity of the squeezing or compressing over time to dynamically scramble the modes.

15. The system according to claim 12, wherein the computer component controls the mode scrambler to vibrate the multimode fiber.

16. The system of claim 11, wherein said multimode fiber includes a core having a substantially rectangular cross-sectional shape.

17. The system of claim 1, wherein the detector component comprises a CCD camera.

18. The system of claim 1, wherein said detector component comprises at least two CCD cameras.

19. The system of claim 1, wherein the detector component further comprises one or more optic filters appropriate to filter fluorescence emissions from the nucleic acids and light from the illumination beam.

20. The system of claim 1, wherein the fluid direction system includes two fluidics stations for operating on two flowcells simultaneously.

21. The system of claim 1, wherein the illumination system comprises two excitation lasers coupled through a fiberoptic device, wherein the excitation lasers illuminate at least part of the footprint.

22. The system of claim 1, further comprising:
   a temperature control system for regulating the temperature of at least one of the solid substrate and the reagents, and;
   a computer component operably coupled to the detector component, wherein the computer component comprises an instruction set for acquiring fluorescence images from the detector component;
   wherein the nucleic acids comprise DNA clusters and the reagents comprise bases having the fluorescent labels, each DNA cluster including a plurality of single-stranded DNA fragments having a common sequence; and
   wherein the fluid direction system, the temperature control system, the illumination system, the detector component, and the computer component cooperate with one another to perform a DNA sequencing cycle including the steps of:
   (i) incorporating at least one base onto the DNA fragments of the DNA clusters;
   (ii) illuminating the DNA clusters to excite the fluorescent labels of the bases;
   (iii) capturing an image of emitted fluorescence from the DNA clusters;
   (iii) identifying the base incorporated onto the DNA fragments of the DNA clusters based upon the emitted fluorescence from the DNA clusters; and
   (iv) removing the fluorescent labels from the bases.

23. The system of claim 22, wherein the base is one of four types of bases, the bases of each type having a unique fluorescent label.

24. The system of claim 22, wherein the computer component is configured to repeat steps (i)-(iv) to determine the sequences of the DNA fragments.

25. The system of claim 22 wherein the detector component is a CCD camera and a density of DNA clusters recorded on the CCD camera is about 5,000 to 50,000 clusters per million pixels.

26. The system of claim 1, wherein the reagents include four different bases in which each base has a different fluorescent label, the illumination system including first and second lasers, each of the first and second lasers exciting two of the four fluorescent labels so that the four fluorescent labels are excited by the first and second lasers.

27. The system of claim 26 further comprising four different optical filters for selecting the fluorescence emission wherein two of the four filters have a narrower bandwidth than the other two of the four filters.

28. A system according to claim 1, further comprising a computer component that is operably coupled to the mode scrambler, the computer component configured to control the mode scrambler to change an index of refraction along the multimode fiber to scramble the modes and provide the substantially uniform illumination footprint.

29. A system according to claim 28, wherein the computer component controls the mode scrambler to dynamically change the index of refraction such that the index of refraction is changed by a first degree and subsequently changed by a second degree, wherein the first and second degrees are different amounts.

30. A system according to claim 28, wherein the computer component controls the mode scrambler to change the index of refraction along the multimode fiber a plurality of times within a predetermined image capture time period.

31. A system according to claim 28, wherein the computer component controls the mode scrambler to change the index of refraction at a plurality of nodes along the multimode fiber.

32. A system according to claim 1, wherein the mode scrambler includes a waveplate, the illumination beam propagating through the waveplate before illuminating the footprint.

33. A system according to claim 32, wherein the waveplate is rotating when the illumination beam propagates therethrough.

34. A system according to claim 1, wherein the footprint is sized to excite at least twenty thousand clusters of DNA that are separate from each other.

35. A system according to claim 1, wherein the footprint is sized to be at least 0.25 $mm^2$.

36. A system for detecting fluorescence emitted from a sample, the system comprising:
  a) a stage configured to hold a solid substrate having the sample;
  b) a fluid direction system for controllably moving one or more reagents into contact with the sample;
  c) an illumination system for exciting fluorescent labels in the sample via total internal reflection (TIR), the illumination system comprising a mode scrambler and a multimode optical fiber that provides a fluorescent-excitation illumination beam having multiple propagating modes, the mode scrambler scrambling the modes of the illumination beam to provide a substantially uniform illumination footprint to excite the fluorescent labels, wherein the illumination beam is directed to be incident on the solid substrate so that the footprint excites the fluorescent labels through TIR; and
  d) a detector component for detecting fluorescence produced from excitation of the fluorescent labels by the footprint thereby providing fluorescent data;
  e) a computer component comprising an instruction set to process the fluorescent data and determine sequence information for nucleic acids in the sample.

37. The system of claim 36, further comprising the solid substrate, the solid substrate comprising a flowcell having at least one fluidic channel.

38. The system of claim 36, further comprising the reagents and the sample having the nucleic acids, the nucleic acids including polynucleotides, the reagents comprising components to extend a second sequence complementary to the one or more polynucleotides.

39. The system according to claim 38, wherein said reagents are fluorescently labeled nucleoside triphosphates.

40. The system of claim 38, wherein the reagents include four different reagents having respective fluorescent labels, the detector component further comprising four optic filters appropriate for filtering emissions of the four fluorescently labeled reagents and light from the illumination beam.

41. The system of claim 36, wherein the illumination system comprises at least one excitation laser coupled through the multimode fiber.

42. The system according to claim 41, wherein the computer component is operably coupled to the mode scrambler, the computer component controlling the mode scrambler to physically engage the multimode fiber to change an index of refraction of the multimode fiber a plurality of times to scramble the modes.

43. The system of claim 41, wherein said multimode fiber includes a core having a substantially rectangular cross-sectional shape.

44. The system of claim 36, wherein said detector component comprises at least two CCD cameras.

45. The system of claim 36, wherein the fluid direction system includes two fluidics stations for operating on two flowcells simultaneously.

46. The system of claim 36, wherein the illumination system comprises two excitation lasers coupled through a fiberoptic device, wherein the excitation lasers illuminate at least part of the footprint.

47. The system of claim 36, further comprising:
  a temperature control system for regulating the temperature of at least one of the substrate and the reagents;
  wherein the computer component is operably coupled to the detector component, wherein the computer component comprises an instruction set for acquiring fluorescence images from the detector component;
  wherein the nucleic acids comprise DNA clusters and the reagents comprise bases having the fluorescent labels, each DNA cluster including a plurality of single-stranded DNA fragments having a common sequence; and
  wherein the fluid direction system, the temperature control system, the illumination system, the detector component, and the computer component cooperate with one another to perform a DNA sequencing cycle including the steps of:
  (i) incorporating at least one base onto the DNA fragments of the DNA clusters;
  (ii) illuminating the DNA clusters to excite the fluorescent labels of the bases;
  (iii) capturing an image of emitted fluorescence from the DNA clusters;
  (iii) identifying the base incorporated onto the DNA fragments of the DNA clusters based upon the emitted fluorescence from the DNA clusters; and
  (iv) removing the fluorescent labels from the bases.

48. A system according to claim 36, wherein the computer component is operably coupled to the mode scrambler, the computer component configured to control the mode scrambler to change an index of refraction along the multimode fiber to scramble the modes and provide the substantially uniform illumination footprint.

49. A system according to claim 48, wherein the computer component controls the mode scrambler to dynamically change the index of refraction such that the index of refraction is changed by a first degree and subsequently changed by a second degree, wherein the first and second degrees are different amounts.

50. A system according to claim 48, wherein the computer component controls the mode scrambler to change the index of refraction along the multimode fiber a plurality of times within a predetermined image capture time period.

51. A system according to claim 48, wherein the computer component controls the mode scrambler to change the index of refraction at a plurality of nodes along the multimode fiber.

52. A system according to claim 36, wherein the mode scrambler includes a waveplate, the illumination beam propagating through the waveplate before illuminating the footprint.

53. A system according to claim 36, wherein the footprint is sized to excite at least twenty thousand clusters of DNA that are separate from each other.

54. A system according to claim 36, wherein the footprint is sized to be at least 0.25 mm$^2$.

* * * * *

UNITED STATES PATENT AND TRADEMARK OFFICE
CERTIFICATE OF CORRECTION

Page 1 of 1

PATENT NO. : 8,241,573 B2
APPLICATION NO. : 12/295337
DATED : August 14, 2012
INVENTOR(S) : Saibal Banerjee et al.

It is certified that error appears in the above-identified patent and that said Letters Patent is hereby corrected as shown below:

Column 48, Line 54: Delete "(iii)" and insert --(iv)--, therefor.

Column 48, Line 57: Delete "(iv)" and insert --(v)--, therefor.

Column 50, Line 58: Delete "(iii)" and insert --(iv)--, therefor.

Column 50, Line 61: Delete "(iv)" and insert --(v)--, therefor.

Signed and Sealed this
Twenty-third Day of October, 2012

David J. Kappos
*Director of the United States Patent and Trademark Office*